United States Patent [19]

Ehret et al.

[11] Patent Number: 5,006,985
[45] Date of Patent: Apr. 9, 1991

[54] COMPUTER SYSTEM FOR MINIMIZING BODY DYSFUNCTIONS INDUCED BY JET TRAVEL OR SHIFT WORK

[75] Inventors: Charles F. Ehret, Hinsdale, Ill.; William T. Ashton, Jr., Woodside, Calif.

[73] Assignee: Kinetic Software, Inc., Woodside, Calif.

[21] Appl. No.: 219,590

[22] Filed: Jul. 15, 1988

[51] Int. Cl.$^5$ ................. G06F 15/21; G06F 15/42
[52] U.S. Cl. ......................... 364/413.01; 364/401
[58] Field of Search ... 364/400, 401, 407, 200 MS File, 364/900 MS File, 413.01; 368/21, 28, 41, 10

[56] References Cited

U.S. PATENT DOCUMENTS

| | | | |
|---|---|---|---|
| 4,600,723 | 7/1986 | Short et al. | 514/416 |
| 4,665,086 | 5/1987 | Short et al. | 514/416 |
| 4,893,291 | 1/1990 | Bick et al. | 368/10 |

OTHER PUBLICATIONS

Wever, *The Circadian System of Man: Results of Experiments Under Temporal Isolation*, New York, Springer-Verlag 1979, pp. 135-140.

Ehret et al., *Overcoming Jet Lag*, New York, Berkley, 1983, pp. 1-160.
Oguma, *Patent Abstracts of Japan*, vol. 11, No. 42, Abstract No. 61-211760, Sep. 1986.
Keller, Expert System Technology: Development and Application, New Jersey, Prentice-Hall, 1987, pp. 76-109.
Belden, "A Program to do Away with Jet Lag", *Philadelphia Inquirer*, Business Section, 7/10/89.
Editors L. E. Scheving and F. Halberg, Sijthoff and Noordhoff, Alphen aan den Rijn, "Chronolobiology—Principals and Applications to Shifts in Schedules", Netherlands, 1980, pp. 417-431 and pp. 353-369.

Primary Examiner—Jerry Smith
Assistant Examiner—David Huntley
Attorney, Agent, or Firm—Townsend and Townsend

[57] ABSTRACT

A computer system incorporates an expanded and integrated theory of Chronobiology and Circadian Regulatory Biology to provide consistent recommendations for the reduction of the effects of jet lag. The system provides consistent recommendations in response to a traveler's itinerary, meeting schedule, and personal preferences. The system can also be used to minimize the effects of changes in work and sleep schedules caused by shift work.

26 Claims, 43 Drawing Sheets

Fig. 1a

Personal Data – Page 1

| | |
|---|---|
| Name: | James Cook |
| Company: | Kinetic Software Inc. |
| Street: | 1406 Burlingame Ave., Suite 31 |
| City: | Burlingame |
| State: | CA |
| Zip Code: | 94010 |
| Country: | USA |
| Telephone: | 415-342-3338 |

Cook SFO-MIL.Trip.JET-READY

File  Personal  Planning  Analysis  Times

[Page 2] [Page 3] [Cancel] [Page 1 OK]

File Personal Planning Analysis Times

Personal Data – Page 3

Passport #:    — 200

Person to notify in an emergency:    — 205

Blood Type:    — 210

Immunization:    — 220

Allergies:    — 230

Foods allergic to or can't take:    — 235

Page 1 — 250    Page 2 — 260    Cancel — 270    Page 3 OK — 280

Fig. 3

| Leg # | Flight Codes | Time Zone of Departure | Arrival | Time Change | Nights at Destination |
|---|---|---|---|---|---|
| 1: | A3APHSFOMILOR | 4 | 13 | +10 | 12 |
| 2: | A16APMMILSFOMR | 13 | 4 | −9 | END |
| 3: | | | | | |
| 4: | | | | | |
| 5: | | | | | |
| 6: | | | | | |
| 7: | | | | | |
| 8: | | | | | |
| 9: | | | | | |

Menu: File  Personal  Planning  Analysis  Times

Itinerary

Buttons: OK  Cancel

Labels: 300, 301, 302, 305, 310, 320, 330

POTENTIAL SCHEDULING PROBLEMS

| ARRIVAL DATE | EVENT LOCATION | ON DATES | IN TIME ZONE | SHIFT CLOCK (HRS) | SHIFT TO NEW TIME ZONE ON DATE | PREFERRED DAY OF CLOCK NO LATER THAN DATE | DAYS BEFORE EVENT |
|---|---|---|---|---|---|---|---|
| 4/04 | MILAN, ITALY | 4/06-4/10 | 13 | +10 | 4/04 | 4/03 FRIDAY | 3 |
| 4/16 | SAN FRANCISCO | | 4 | -9 | 4/16 | | |

DATES IN BOLD TYPE INDICATE MEETINGS SCHEDULED TOO CLOSE TO OVERCOME JET LAG.

\* USING THE ANTI-JET LAG MEASURES

MINIMUM EXTRA DAYS RECOMMENDED TO ADAPT TO TIME ZONE CHANGES.
USING THE JET LAG MEASURES = 3 DAYS
NOT USING THE JET LAG MEASURES = 8 DAYS

| SUNDAY | MONDAY | TUESDAY | TRIP CALENDAR<br>WEDNESDAY |
|---|---|---|---|
| 3/29<br>ON SAN FRANCISCO TIME | 3/30 | 3/31 FEAST | 4/1 FAST |
| 4/5 | 4/6<br>APPT 9:00AM | 4/7<br>APPT 9:00AM | 4/8<br>APPT 9:00AM |
| 4/12 | 4/13 | 4/14 | 4/15 FEAST |

|  THURSDAY | FRIDAY | SATURDAY |
|---|---|---|
| 4/2  ⌈ ̄FEAST ̄⌉<br>      ⌊_ _ _ _⌋<br>700 | 4/3   FAST<br>705<br>⌈SAN FRANCISCO⌉<br>⌊TO<br> MILAN⌋ | 4/4  ⌈ ̄FEAST ̄ ̄ ̄ ̄ ̄⌉<br>⌈BREAK-THE-FAST⌉<br>⌊WITH BREAKFAST⌋<br>⌊ON MILAN TIME⌋<br>⌈SAN FRANCISCO⌉<br>⌊TO<br> MILAN⌋ 720<br>710 |
| 4/9      730<br>⌈APPT 9:00AM⌉<br>⌊_ _ _ _ _ _⌋ | 4/10<br>APPT 9:00AM<br>725 | 4/11 |
| 4/16 ⌈ ̄FAST ̄ ̄ ̄⌉<br>⌈BREAK-THE-FAST⌉<br>⌊WITH BREAKFAST⌋<br>⌊ON SAN FRANCISCO TIME⌋<br>MILAN<br>TO<br>SAN FRANCISCO | 4/17<br>⌈_ _ _ _ _ _ _⌉<br>⌊_ _ _ _ _ _ _⌋ | 4/18 |

FIG. 7B

FLIGHT ITINERARY

JAMES COOK, SAN FRANCISCO TO MILAN
KINETIC SOFTWARE INC.
1406 BURLINGAME AVE., SUITE 31
BURLINGAME, CA 94010 USA

| | DEPARTING | TIME ZONE | DATE | TIME | ARRIVING | TIME ZONE | DATE | TIME | AIRLINE | FLIGHT# |
|---|---|---|---|---|---|---|---|---|---|---|
| 1 | SAN FRANCISCO | 4 | 4/3 | 9:04AM | CHICAGO, IL | 6 | 4/3 | 2:59PM | UNITED | 126 |
|  | CHICAGO, IL | 6 | 4/3 | 4:20PM | MILAN, ITALY | 13 | 4/4 | 8:50AM | ALITALIA | 617 |
| 2 | MILAN, ITALY | 13 | 4/16 | 1:55PM | CHICAGO, IL | 6 | 4/16 | 4:15PM | ALITALIA | 616 |
|  | CHICAGO, IL | 6 | 4/16 | 5:45PM | SAN FRANCISCO | 4 | 4/16 | 8:15PM | UNITED | 203 |

| FAST DAY - SAMPLE MENU | CALORIES | PROTEIN | FAT | CARBOHYDRATES |
|---|---|---|---|---|
| BREAKFAST | | | | |
| 1 EGG, ANY STYLE | 82 | 6 | 6 | 1 |
| 1/2 CUP LOW-FAT COTTAGE CHEESE | 86 | 14 | 1 | 3 |
| 1/2 CUP OF ORANGE JUICE | 60 | 0 | 0 | 10 |
| MEAL TOTALS: | 228 | 20 | 7 | 14 |
| LUNCH | | | | |
| 1/2 CUP WATER-PACKED TUNA | 170 | 15 | 11 | 0 |
| 1 PIECE OF BREAD, LIGHTLY BUTTERED | 60 | 2 | 1 | 12 |
| A FEW SLICES OF TOMATO AND LETTUCE | 25 | 2 | 0 | 5 |
| 1/4 CUP LOW-FAT OR SKIM MILK | 30 | 2 | 1 | 3 |
| MEAL TOTALS: | 285 | 21 | 13 | 20 |
| SUPPER | | | | |
| MEDIUM-SIZE PLATE OF SALAD | 64 | 3 | 1 | 14 |
| 1 TB. SALAD DRESSING | 60 | 0 | 6 | 2 |
| 1 PIECE OF BREAD, LIGHTLY BUTTERED | 60 | 2 | 1 | 12 |
| 1 ALCOHOLIC BEVERAGE (OPTIONAL) | 100 | 0 | 0 | 0 |
| 1 APPLE OR PEAR | 70 | 0 | 0 | 18 |
| MEAL TOTALS: | 354 | 5 | 8 | 46 |
| DAY TOTALS: | 867 | 46 | 28 | 80 |

RECOMMENDED TOTAL CALORIES ON A FAST DAY = 800

FIG. 8A

| FEAST DAY - SAMPLE MENU | CALORIES | PROTEIN | FAT | CARBOHYDRATES |
|---|---|---|---|---|
| BREAKFAST | | | | |
| STEAK AND EGGS | 320 | 36 | 19 | 1 |
| MILK | 118 | 8 | 2 | 12 |
| 1/2 CUP OF ORANGE JUICE | 60 | 0 | 0 | 10 |
| 1 PIECE OF BREAD | 60 | 2 | 1 | 12 |
| MEAL TOTALS: | 558 | 46 | 22 | 35 |
| LUNCH | | | | |
| LOTS OF ASSORTED COLD CUTS | 200 | 32 | 10 | 0 |
| ASSORTED CHEESES | 114 | 7 | 10 | 1 |
| MILK | 118 | 8 | 2 | 12 |
| 1 PIECE OF BREAD | 60 | 2 | 1 | 12 |
| 1 CUP VEGETABLES | 64 | 3 | 0 | 13 |
| MEAL TOTALS: | 556 | 52 | 23 | 38 |
| SUPPER | | | | |
| PASTA WITH MEATLESS TOMATO SAUCE | 320 | 36 | 19 | 1 |
| BREAD, LIGHTLY BUTTERED | 60 | 2 | 1 | 12 |
| FRUIT SALAD, AS MUCH AS WANTED | 60 | 0 | 0 | 10 |
| CAKE, COOKIES | 150 | 2 | 4 | 30 |
| ONE ALCOHOLIC BEVERAGE | 100 | 0 | 0 | 0 |
| MEAL TOTALS: | 690 | 40 | 24 | 53 |
| DAY TOTALS: | 1804 | 138 | 69 | 126 |

© COPYRIGHT 1987 KINETIC SOFTWARE INC. ALL RIGHTS RESERVED.

FIG. 8B

RECOMMENDED HOURS OF ACTIVITY (IN THIS 24 HOUR CLOCK "00" IS MIDNIGHT AND "12" IS NOON.)

THE HOURS APPEARING IN "BOLD" TYPE BELOW ARE THE RECOMMENDED PERIODS OF ACTIVITY IN EACH OF THE CITIES WHERE A STOPOVER OCCURS. TO MAXIMIZE THE BENEFITS OF YOUR JET-READY INSTRUCTIONS, YOU SHOULD SCHEDULE ACTIVITIES AND EVENTS IN EACH REFERENCED CITY DURING THE HOURS IN "BOLD" TYPE. THE CHART MAY ALSO BE USED TO DETERMINE WHAT TIME IT IS IN A DIFFERENT TIME ZONE AND TO DECIDE, FOR EXAMPLE, WHEN, TO CALL HOME.

SAN FRANCISCO
15 16 17 18 19 20 21 22 23 00 01 02 03 04 05 06 [07 08 09 10 11 12 13 14 15 16 17 18 19 20 21 22] 23 00

...CHANGE TO MILAN, ITALY TIME PER AGENDA INSTRUCTIONS...  900

MILAN, ITALY (+10 HOURS)
01 02 03 04 05 06 [07 08 09 10 11 12 13 14 15 16 17 18 19 20 21 22] 23 00

© COPYRIGHT 1987  KINETIC SOFTWARE INC.  ALL RIGHTS RESERVED
NO PART OF THESE MATERIALS MAY BE REPRODUCED, STORED IN A RETRIEVAL SYSTEM, OR TRANSMITTED IN ANY FORM OR BY ANY MEANS, ELECTRONIC, MECHANICAL OR OTHERWISE, WITHOUT THE PRIOR WRITTEN PERMISSION OF KINETIC SOFTWARE INC.

DAILY AGENDAS - DAYS BEFORE SCHEDULED DEPARTURE

TRIP LEG #1: SAN FRANCISCO, CA TO MILAN, ITALY
JAMIE COOK, SAN FRANCISCO TO MILAN TRIP

| STARTING ON DEPARTURE TIME (PST*) | 4/1/1987 WEDNESDAY FAST DAY | 4/2/1987 THURSDAY FEAST DAY |
|---|---|---|
| 7AM-9AM(PST*) | LIGHT BREAKFAST NO CAFFEINE, DECAFF OK | BIG HIGH-PROTEIN BREAKFAST NO CAFFEINE, DECAFF OK |
| 11AM-1PM(PST*) | LIGHT LUNCH NO CAFFEINE, DECAFF OK | BIG HIGH-PROTEIN LUNCH NO CAFFEINE, DECAFF OK |
| 3PM-4PM(PST*) | CAFFEINE OK | CAFFEINE OK |
| 5PM-7PM(PST*) | LIGHT SUPPER NO CAFFEINE, DECAFF OK | BIG LOW-PROTEIN, HIGH-CARBOHYDRATE SUPPER NO CAFFEINE, DECAFF OK |
| 9PM-11PM(PST*) | NO SNACKS NORMAL BEDTIME | LIGHT SNACKS OK EARLY TO BED |

* PST - PACIFIC STANDARD TIME

910

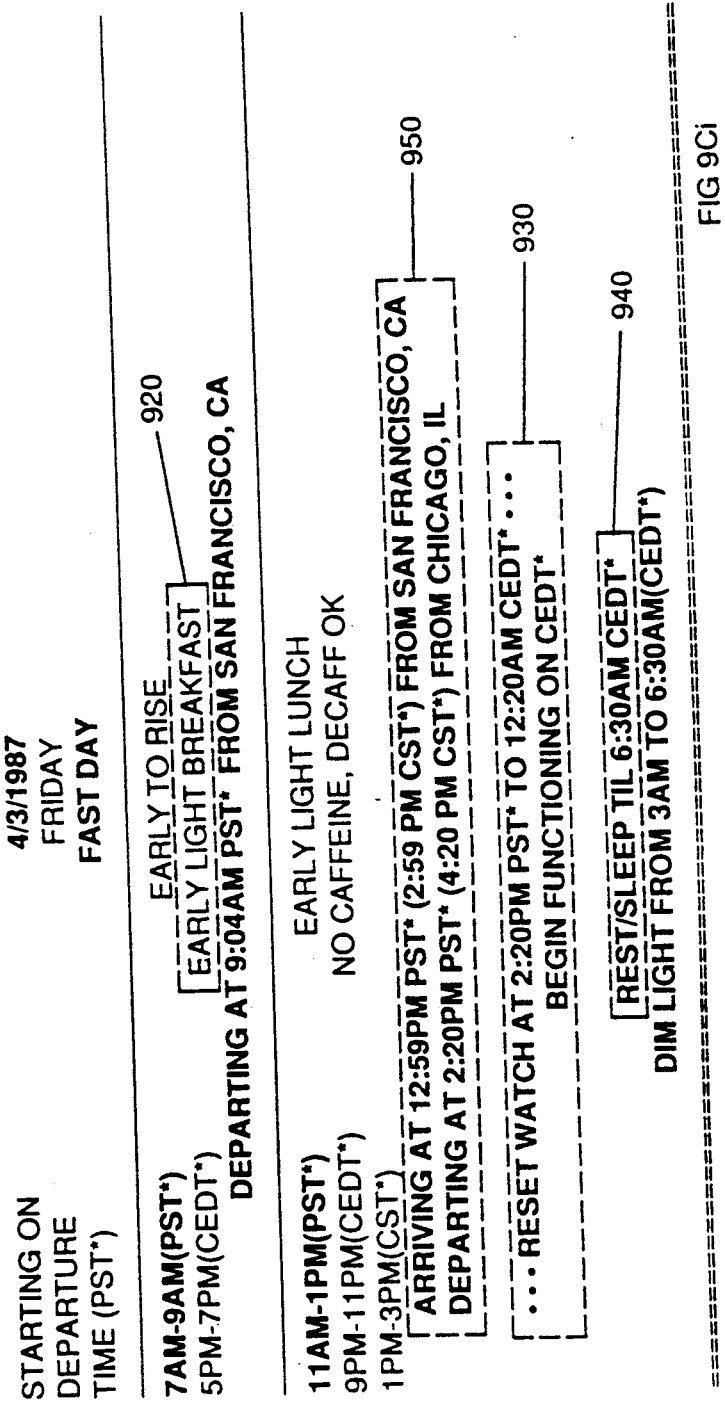

4/4/1987
SATURDAY
FEAST DAY

STARTING ON
DESTINATION
TIME (CEDT*)

**7AM-9AM (CEDT*)**
9PM-11PM (PST*)

[ 1/2 HOUR MENTAL & PHYSICAL EXERCISE BEFORE BREAKFAST ]—945
BIG HIGH-PROTEIN BREAKFAST
[ 2-3 CUPS COFFEE OR OTHER CAFFEINATED BEVERAGE ]—925
[ BRIGHT LIGHT FROM 7AM TO 12 NOON (CEDT*) ]—955
ARRIVING AT 8:50AM CEDT* IN MILAN, ITALY

**11AM-1PM (CEDT*)**
1AM-3AM (PST*)

BIG HIGH-PROTEIN LUNCH
NO CAFFEINE, DECAFF OK
[ DIM LIGHT FROM 2PM TO 10PM (CEDT*) ]—960

**3PM-4PM (CEDT*)**
5AM-6AM (PST*)

NO CAFFEINE, DECAFF OK

**5PM-7PM (CEDT*)**
7AM-9AM (PST*)

BIG LOW-PROTEIN, HIGH-
CARBOHYDRATE SUPPER
NO CAFFEINE, DECAFF OK

**9PM-11PM (CEDT*)**
11AM-1PM (PST*)

NO SNACKS—930
[ EARLY TO BED ]

* PST - PACIFIC STANDARD TIME   * CEDT - CENTRAL EUROPEAN DAYLIGHT TIME
* CST - CENTRAL STANDARD TIME
© COPYRIGHT 1987  KINETIC SOFTWARE INC.   ALL RIGHTS RESERVED

FIG. 9Cii

COMPUTER SYSTEM FOR MINIMIZING BODY DYSFUNCTIONS INDUCED BY JET TRAVEL OR SHIFT WORK

BACKGROUND OF THE INVENTION

The present invention relates to the fields of chronobiology, circadian regulatory biology, and computer systems, and, more specifically, to a computer system for reducing the effects of physical and mental dysfunction associated with phase changes caused by shift work or travel from one time zone to another, commonly known as "jet-lag".

The symptoms referred to as "jet lag" are due not to fatigue, as is commonly believed by laypersons, but to a lack of synchronization between certain organs acting as "body clocks" and external stimulus from the environment. Particularly, jet-lag symptoms can result from either shift work, where an individual is changing his normal working hours, or from travel from one time zone to another. The fields of Chronobiology and Circadian Regulatory Biology focus on the nature of "body clocks" and the biochemistry and anatomy of circadian clocks in higher organisms, including man. Learning how to "reset" these clocks has been a central aim of research in this field, as discussed in *Overcoming Jet Lag*, Ehret, C. F. and Scanlon, L. W., Berkley Publishing, New York, 1983; *The Effects of Jet Lag on Sports Performance*, Sasaki, Takashi, p.417–432 (Japanese/Soviet Volleyball Performance Study) in *Chronobiology—Principals and Applications to Shifts in Schedules*, Editors L. E. Scheving & F. Halberg, Sijthoff & Noordhoff, Alphen aan den Rijn, Netherlands, 1980; and "*Recent Studies Relative to the Airlifting of Military Units Across Time Zones*", Graeber, R. Curtis, (Rapid Deployment Force Jet Lag Study), p.353–370 in *Chronobiology—Principals and Applications to Shifts in Schedules*, Editors L. E. Scheving & F. Halberg, Sijthoff & Noordhoff, Alphen aan den Rijn, Netherlands, 1980.

This research relates to resetting the body's clocks with the help of several selected "zeitgebers" (from the German for 'time givers'). These zeitgebers regulate or shift the phase of a circadian rhythm, and can, as their name implies, act as "time givers". For example, the application of the prescription drug alpha-methyl-paratyrosine (A.M.T.) clearly and predictably resets the circadian systems. Numerous other zeitgebers have also been shown to affect circadian rhythms. These zeitgebers include, for example, light, exercise, food, and such commonly used non-prescription drugs as caffeine, theophylline, and theobromine (found in coffee, tea, and cocoa). The type of food and the times that these foods are ingested are critical in determining how to properly stimulate certain "body clocks". The proper introduction of external stimuli such as light, physical and mental activity, the ingestion of natural chemicals such as caffeine, and a feast-fast meal cycle, can be effectively used to correct the disturbance of body rhythms.

The techniques described in *Overcoming Jet Lag* require the use of multiple zeitgebers and take advantage of the naturally occurring "circadian oscillations in energy reserves". In the pre-flight days, the techniques focus on alternately building up and depleting glycogen energy reserves by the use of a special diet which prepares the body's clocks for resetting. During a four day pre-flight program, the traveler feasts one day, fasts the next day (indicated by day*), feasts again, and fasts again on the final day (indicated by day**) before phase shifting to a new time zone. The traveler then breaks the final fast with breakfast time at his destination (B.T.F.W.B.D.T.). In the unusual case of anticipated extraordinary caloric demands on either of these days (such as by an athlete during training on day*, or even more unlikely on day**), then the "fast day" may be designed to look almost like a "feast-day" for one not-in-training, since the aim at the end of each respective "fast day" is to nearly, but not completely, deplete the available glycogen reserves for that day, to be restored either with "Feast" after day*, or with B.T.F.W.B.D.T. after day**.

However, one difficulty with the practical application of present Chronobiology theory is that no integrated, reliable, and automatic mechanism has been developed for dealing with rule conflicts, compromises or impossibilities, such as when a recommended sleep phase is interrupted by a flight departure or arrival.

For an individual seeking a consistent and integrated schedule of activities for a particular trip, these prior art publications are usually not adequate. There is a practical limit to how many examples can be given in a book, understood by the reader, and extrapolated to other situations. Even when an example is pertinent, the recommendations are often ambiguous or even in conflict with the traveler's schedule or personal preferences. Most individuals have personal preferences for meeting times, meal times, and sleep times which are not addressed by the examples or the general techniques of the prior art.

One solution might be to consult with an expert. It is, however, costly and difficult, even for the chronobio-technically astute expert to rigorously apply the general and often complex theory to formulate and recommend a correct schedule of activity for a particular trip. This is especially true for multiple destination flights involving several stops through multiple time zones, flights that do not have the preferred departure and arrival times, or for travel across the International Date Line.

What is needed is a system for formulating, in response to any specific input of travel plans and personal preferences, a consistent and integrated schedule of activities and countermeasures applicable to the conditions of modern transmeridional jet travel to reduce the effects of jet lag. It is desirable that this system be compatible with an airline reservation system that is capable of recommending specific flights at the time of booking.

SUMMARY OF THE INVENTION

The present invention incorporates an expanded and integrated theory of Chronobiology and Circadian Regulatory Biology into a rule-based computer system. The computer system provides consistent recommendations in response to a traveler's itinerary, work schedule, and personal preferences for sleep times and meal times, despite the interrupted environment of trans-time zone jet travel, with stops, layovers, plane changes, etc. The preferred embodiment of the present invention includes a programmed general purpose computer, an input keyboard, a cursor positioning input device, an output display terminal and printer, and databases of time zone, daylight savings information, and flight information. Although the preferred embodiment is adapted for providing recommendations for minimizing body dysfunctions induced by jet travel, the invention is also applicable to minimizing body dysfunctions induced by shift work.

BRIEF DESCRIPTION OF THE DRAWINGS

FIGS. 1a, 1b, and 1c are illustrations of personal data input display screens generated by the preferred embodiment of the present invention.

FIG. 3 is an illustration of an Itinerary input display screen generated by the preferred embodiment of the present invention.

FIG. 6 illustrates a Potential Scheduling Problems output display screen generated by the system in accordance with the preferred embodiment of the present invention.

FIGS. 7A, 7B and 7C are an illustration of The Trip Calendar as output to printer or screen.

FIG. 8A and 8B are an illustration of the "Feast" and "Fast" sample menus as output to printer or screen.

FIG. 9a is an illustration of a Recommended Hours of Activity Display as output to printer or screen.

FIGS. 9B, 9C; and 9C;; illustrations of the Daily Agendas for the days before scheduled departure and for the day of departure as output to printer or screen.

DETAILED DESCRIPTION OF THE PREFERRED EMBODIMENT

The preferred embodiment of the present invention has been developed using the Pascal computer language on a system including a Macintosh computer, manufactured by Apple Computer, Inc., a hard disc drive for the storage of databases, a keyboard and mouse for input of personalized and trip specific data, and an output screen and printer for providing specific outputs describing recommendations for the traveler's activities.

Referring to FIGS. 1 thru 10 the major display screens of the preferred embodiment are shown and will now be described.

Figure 1B:
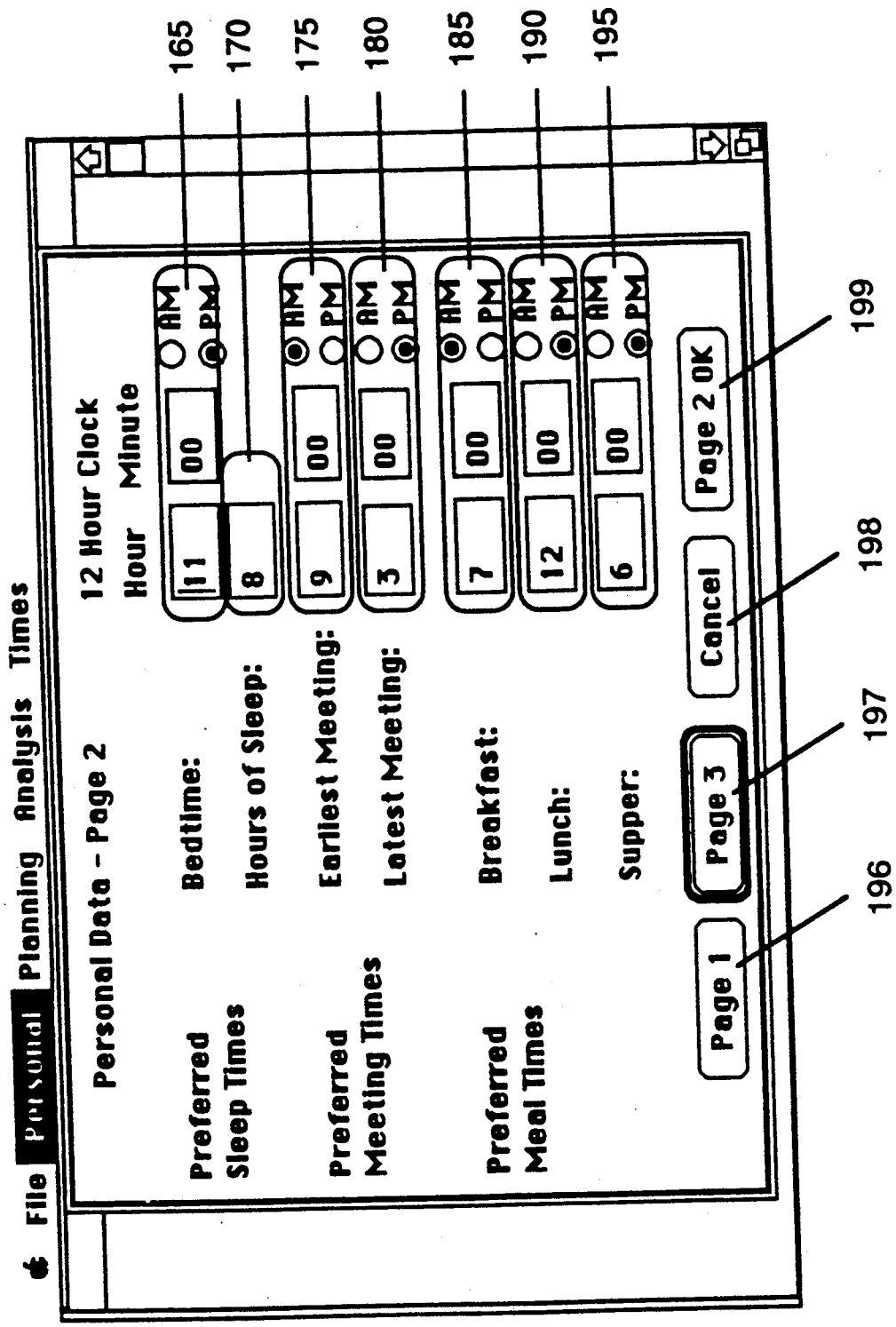

FIGS. 1a, 1b, and 1c are illustrations of personal data input display screens pages 1, 2, and 3, respectively, generated by the preferred embodiment of the present invention. Referring to FIG. 1a, an operator is prompted to enter a passenger's name, company, address, and telephone number. This data is entered into name display area 105, company display area 110, street display area 115, city display area 120, state display area 125, zip code display area 130, country display area 135, and telephone display area 140. In response to clicking button 145 the system accepts changes and displays the second page of the personal data input display screen illustrated in FIG. 1b. Alternatively, the operator can accept changes and select page 3 with button 150, cancel any changes to this screen with button 155, or accept changes and return to the main program with button 160.

Referring to FIG. 1b, the operator is prompted to enter the traveler's preferences for bedtime, hours of sleep, earliest time for meetings, latest time for meetings, time for breakfast, time for lunch, and time for supper. The traveler's preference for bedtime is entered in display area 165, hours of sleep in display area 170, earliest time for meetings in display area 175, latest time for meetings in display area 180, time for breakfast in display area 185, time for lunch in display area 190, and time for supper in display area 195. In response to clicking button 196 the system accepts changes and displays the first page of the personal data input display screen illustrated in FIG. 1a. Alternatively, the operator can accept changes and select page 3 with button 197, cancel any changes to this screen with button 198, or accept changes and return to the main program with button 199.

Input of traveler preferences is optional. If no information is provided by the operator the program will use standard default values which are displayed when FIG. 1b is first called up for a new traveler. However, the provisions for adapting to personal preferences and characteristics is a major advantage of the present invention and the availability of these personal preferences, especially when they differ from standard default values, will affect the effectiveness of the personal recommendations for jet-lag countermeasures. In an alternative embodiment this personal preference data could be stored in a frequent flyer database under the traveler's name for use in future bookings.

Referring to FIG. 1c, the operator is prompted to enter optional information including but not limited to the traveler's passport number, person to notify in case of emergency, blood type, immunization, allergies and foods which the traveler is allergic to or can't take. The traveler's passport number is entered into display area 200, the person to notify in case of emergency is entered in display area 205, blood type is entered into display area 210, immunization is entered into display area 220, allergies are entered into display area 230, and foods which the traveler is allergic to or can't take are entered into display area 235. In response to clicking button 250 the system accepts changes and displays the first page of the personal data input display screen illustrated in FIG. 1a. Alternatively, the operator can accept changes and select page 2 with button 260, cancel any changes to this screen with button 270, or accept changes and return to the main program with button 280.

Figure 2:
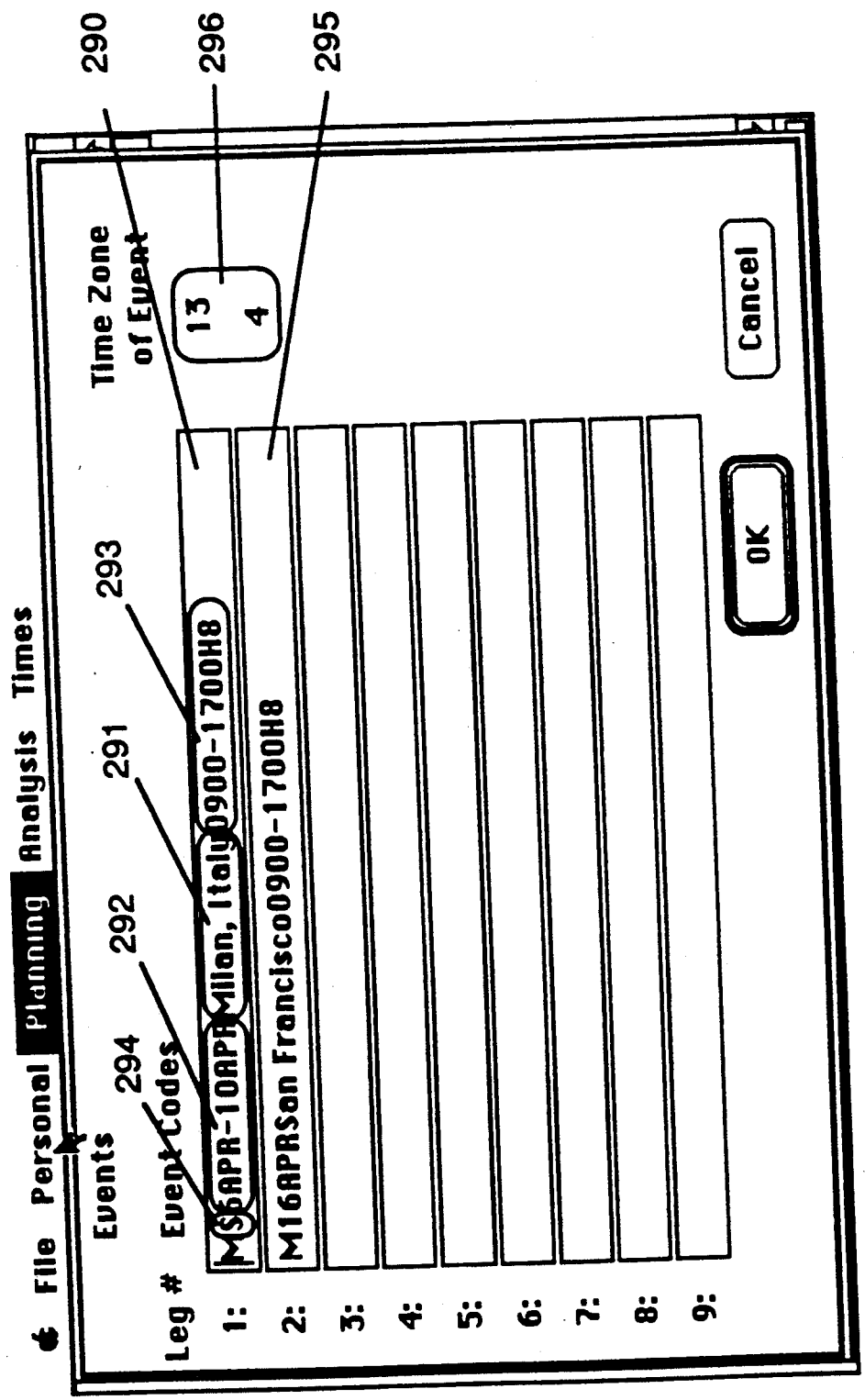
FIG. 2 is an illustration of an Event Codes input display screen generated by the preferred embodiment of the present invention.

FIG. 2 is an illustration of an Event Code input display screen generated by the preferred embodiment of the present invention. In response to prompts, the operator enters the locations, times and duration of scheduled events. For example, an important five day meeting in Milan, Italy is scheduled to start April 6 at 9:00 A.M. This data is entered in an abbreviated form in display area 290. The location, (Milan, Italy), is illustrated in display area 291. The first and last dates of the event are illustrated in display area 292. Eight hours of meeting time ("H8") are required between the times of 9 am (0900) and 5 pm (1700), as illustrated in display area 293. The fact that the event is considered a key or special event is indicated by an "S" illustrated in display area 294. The "key event" designation indicates that this is an event that the traveler desires to be especially well prepared for (e.g., business meetings or sporting event). In response to this designation, the program will give priority to minimizing the effects of phase change for each key event.

As illustrated in FIG. 2, a second event is also scheduled in San Francisco for April 16 and the information for that event has been entered by the operator and is illustrated in display area 295.

A database of time zone information is referenced for each event location and provided by the system. For example, in Time Zone Display 296 the system has referenced the Time Zone Database and provided the designator "13", indicating the Standard Time Zone IDL of Milan and the designator "4" indicating the Standard Time Zone IDL of San Francisco. Standard Time Zones IDL reference the International Date Line ("IDL") and are numbered 1-24 west-to-east from the IDL.

FIG. 3 is an illustration of an Itinerary input display screen generated by the preferred embodiment of the present invention. In response to prompts, the operator defines the legs of the trip in an abbreviated form. Specifically, the departure location for the first leg of the trip, "SFO" has been entered by the operator in display area 300. The date of the flight "3APR" has been entered in display area 301. The recommended time of the flight "9A" (for 9 am) is calculated by the system and is illustrated in display area 302. (After specific flight information has been entered in Step 4, this will be changed to reflect the actual flight time.) The destination city "MIL" (the international airport code) is entered in display area 305. The program calculates the difference in time zones for each leg ("Time Change") and displays that information in display area 310. In the preferred embodiment, the time change information is corrected for any daylight savings scheduled at any arrival or departure location by referencing a database of daylight savings information indexed to both the location and the times and dates of arrival and departure. The number of nights at each intermediate destination is calculated from the actual flight data and displayed in display area 320. The operator enters "END" in the "Nights at Destination" box to indicate the last leg of the trip, as the operator has done in display area 330.

Figure 4:
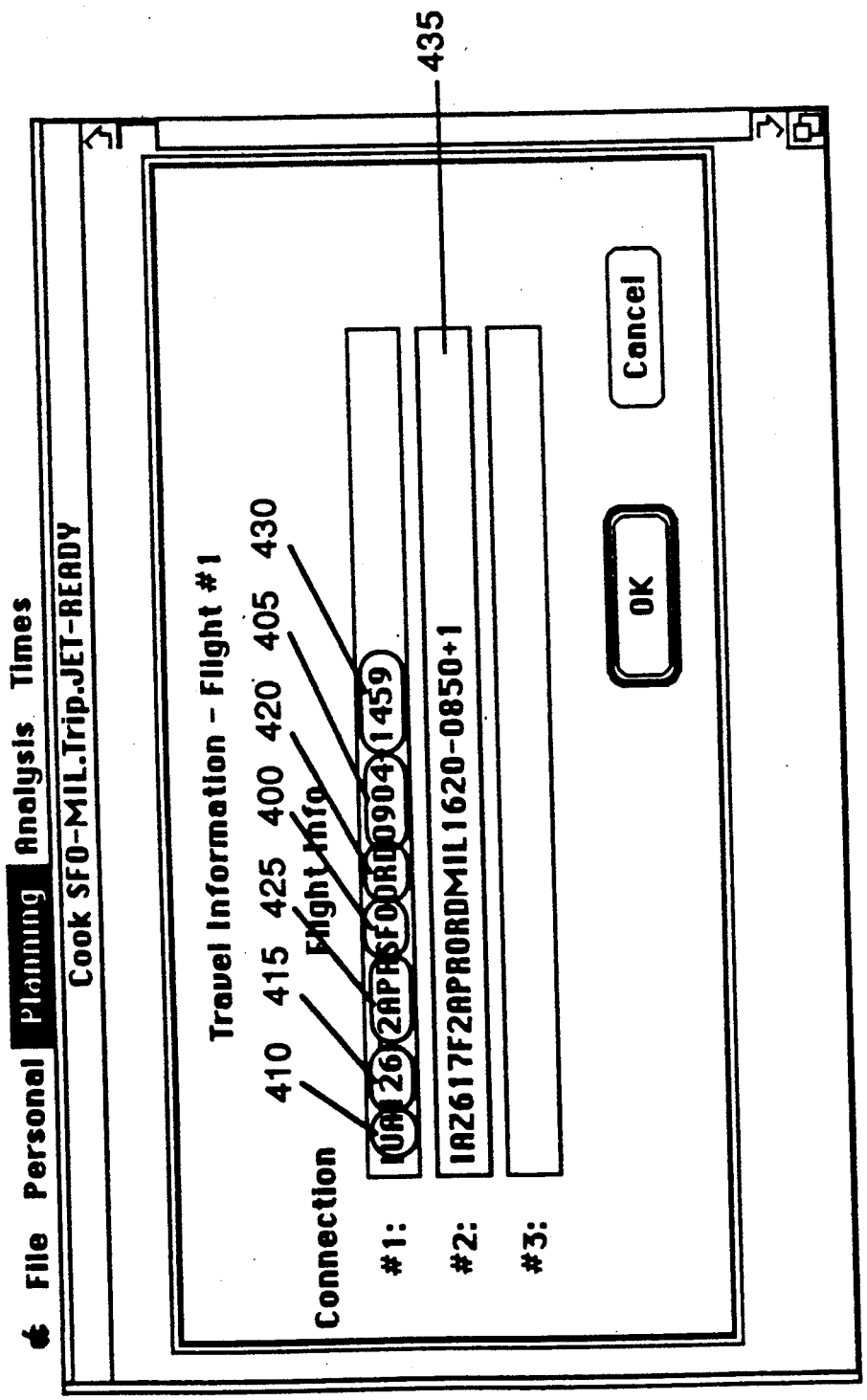
FIG. 4 is an illustration of a Travel Information input display screen generated by the preferred embodiment of the present invention.

FIG. 4 is an illustration of a Travel Information input display screen. This screen is used for the input, modification and display of specific flight data. Choosing one trip leg at a time, the operator inputs the specific flight data consistent with the Itinerary using actual flight data from an OAG database. For example, in FIG. 4 the departure location (SFO) already provided by the operator in Step 2 is displayed in display area 400. The exact time of departure is entered in display area 405. The airline identification "UA" is entered in display area 410, the flight number "126" in display area 415, the destination "ORD" in display area 420, the date of departure is entered in display area 425, and the time of arrival "1459" in display area 430. Specific flight information for additional connecting flights are input in sequential display areas such as display area 435. All connecting flights are entered so that the system can account for interruptions in sleep, such as would be caused by the need to change flights. This information is provided manually in the preferred embodiment, however in an alternative embodiment the information could be provided electronically from an electronic database of flight information. In this alternative embodiment the system could be adapted so as to recommend specific available flights based on chronobiology rules and the key event data.

Once the operator and traveler are satisfied with the input data and proposed flight itinerary the flight data, event data, and personal preferences data are processed in accordance with the system databases and with the Chronobiology Rules defined below.

Figure 5:
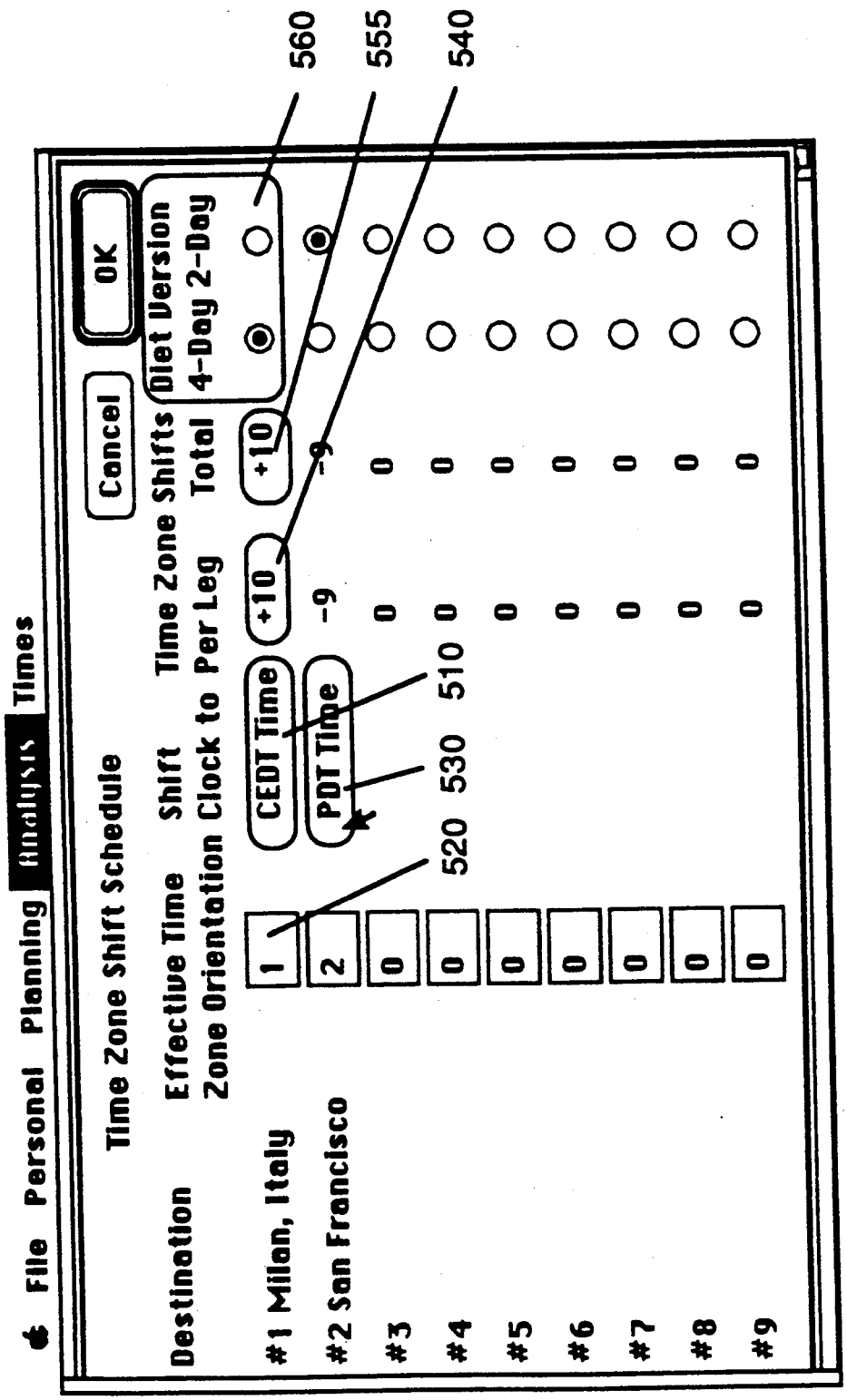
FIG. 5 illustrates a recommended Time Zone Shift Schedule output screen generated by the system.

FIG. 5 illustrates a recommended Time Zone Shift Schedule display generated by the system in response to the input data provided in steps 1-4. Each leg of the trip is represented, and recommendations are given for the time zone that a traveler should live on while at each destination, the "Effective Time Zone orientation". In some circumstances, the system will recommend that the traveler "live" on a time zone other than the local time zone being visited. In such a case the number in display area 520 would correspond to the leg number whose destination reflects the effective time zone orientation. Referring to FIG. 5, the system recommends that the traveler live on CEDT Time while in Milan as shown in display area 510. The "1" in display area 520 refers to the time zone of the first destination (Milan, Italy). The traveler is recommended to change to PDT time while in San Francisco as indicated in display area 530. (The specific method for determining the appropriate date to phase shift is illustrated in FIGS. 32 to 35.) The time zone shift per leg is displayed in display area 540 and the total time zone shift is displayed in display area 555. The recommendations for 4 or 2 day diet is provided in display area 560. A traveler may override the recommendation, and choose, for example, a two day diet rather than a four day diet, if he desires.

FIG. 6 is the Potential Scheduling Problems display screen. This screen shows the event schedule and indicates if insufficient time has been allowed to overcome the phase change effects. For example, the system recommends that the traveler shift to the new time zone no later than three (3) days before the event in Milan as illustrated in display area 605. This corresponds to the date "4/03" illustrated in display area 610. This date is illustrated in bold to indicate that insufficient time has been scheduled to fully adapt to the shift in time zones prior to the event in Milan and the traveler should expect to experience some effects of jet lag at that event.

A number of specific output recommendations and output formats are provided by the system including a Trip Calendar, which indicates travel days, basic dietary recommendations, time zone shifts, and scheduled appointments; a Prime-Time Activity Chart for each leg of the trip; and Daily Agendas for the days surrounding the time shift for each trip leg requiring a time shift.

The Trip Calendar is illustrated in FIG. 7. The Trip Calendar provides specific information for scheduled trip events in a boxed calendar format. Specifically, the trip calendar illustrates each day in a box and indicates whether meals should comply with the "Feast" or the "Fast" menu illustrated in FIG. 8. For example, display area 700 corresponds to March 31 on the calendar, and is designated as a "FEAST" day. Accordingly, it is recommended that the traveler eat in accordance with the "Feast Day - Sample menu" on that day. The Trip Calendar also indicates travel days, such as designated by the names of the departure and destination cities in display areas 705 and 710. Time zone shifts are indicated, by "break the fast" breakfasts such as seen on dates 4/4 and 4/16 and illustrated in display areas 720 and 725. Scheduled appointments are also indicated as, for example, on date 4/6 in display area 730. A flight itinerary summary is also illustrated in display area 740.

A set of sample feast and fast meals is provided for the traveler as illustrated in FIG. 8. This recommends calories and proportions of protein, fat, and carbohydrates for the meals recommended by the method.

A Recommended Hours of Activity display is provided for the effective time zone of the trip as illustrated in FIG. 9a. This chart recommends periods of activity in each of the cities where a stopover occurs. The hours indicated in bold type, such as in area 900, are the times recommended for meetings, key events or other important activities at each location.

As illustrated in FIG. 9b and 9c, Daily Agendas for the days before scheduled departure, such as illustrated in display area 910, and for the day of departure are provided. The Daily Agendas specify the time and type of each meal, such as illustrated in display area 920, when coffee should be consumed, such as illustrated in display area 925, bedtime, such as illustrated in display area 930, the time to reset the traveler's wristwatch, such as illustrated in display area 935, times for inactivity, such as illustrated in display area 940, times for activity, such as illustrated in display area 945, departure and arrival times and locations, such as illustrated in display area 950, and times for bright and dim light, such as illustrated in display areas 955 and 960 respectively.

Figure 10A:
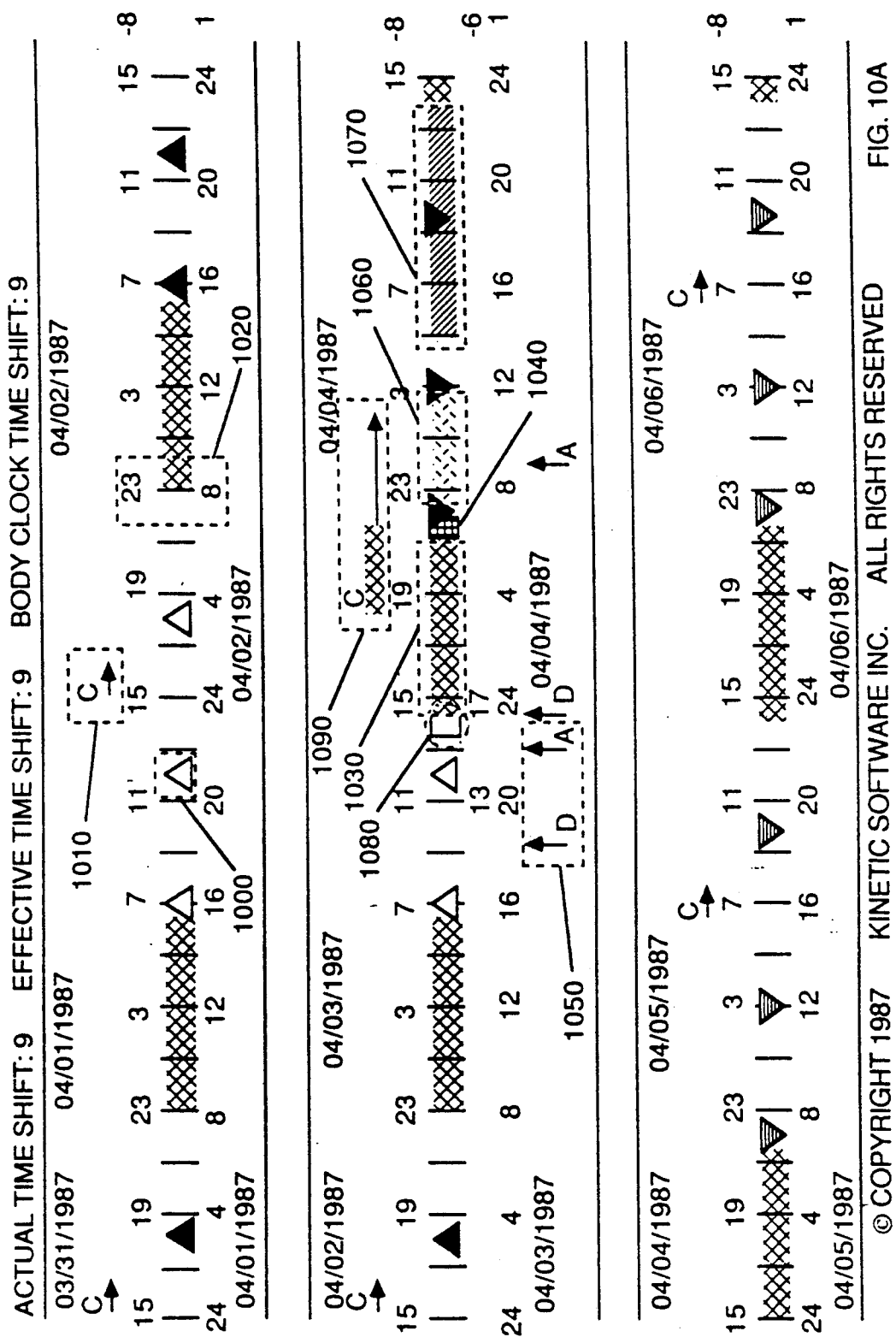
FIGS. 10A and 10B are an illustration of Slide Rule as output to printer or screen.
Figure 10B:
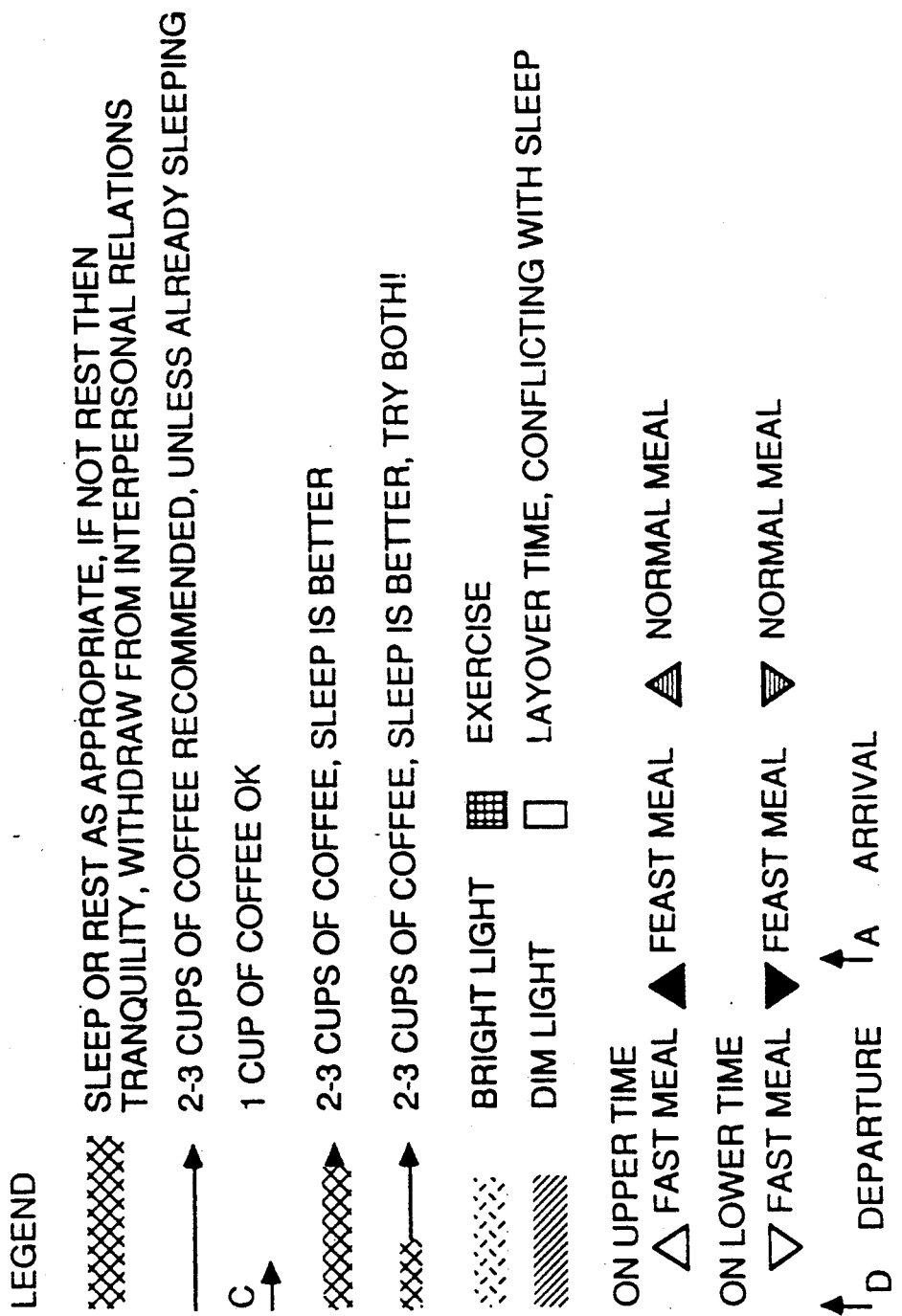

FIG. 10 is an illustration of the Slide Rule output display screen. This format provides a unique visualization of the interrelated factors present in a traveler's schedule in a time line format. The Slide Rule specifies the time and type of each meal, such as illustrated in display area 1000, when coffee should be consumed, such as illustrated in display area 1010, bedtime, such as illustrated in display area 1020, times for inactivity, such as illustrated in display area 1030, times for activity, such as illustrated in display area 1040, departure and arrival times, such as illustrated in display area 1050, and times for bright and dim light, such as illustrated in display areas 1060 and 1070 respectively. This format is particularly useful in the visualization of certain conflict situations, such as layover times conflicting with sleep, as illustrated in display area 1080, and conflicts between drinking coffee and sleep, such as illustrated in display area 1090.

Before describing the internal operation of the computer program of the preferred embodiment, some standard Pascal definitions will be given to explain the use of various constructs in the computer language and thus illuminate the discussion of data types and variables that follows. The following definitions are from the book *Pascal User Manual and Report*, by Kathleen Jensen and Nicklaus Wirth, 1974, published by Springer-Verlag, which is the standard definition of the language.

The order in which the compiler expects to find definitions will be used as a structure for description of the types and variables. A "constant definition" introduces an identifier as a synonym for a constant. The use of constant identifiers generally makes a program more readable and acts as a convenient documentation aid. A data type in Pascal may either be directly described in the variable declaration or referenced by a "type identifier". Several standard type identifiers are included, along with a mechanism, the "type definition", for creating new types. Every variable occurring in a statement must be declared in a "variable declaration" which must precede the use of the variable. A variable declaration associates an identifier and a data type with a new variable by simply listing the identifier followed by its type. A "record" is a structure consisting of a fixed number of components, called fields. Components need not be of identical types and cannot be directly indexed. A "type definition" specifies for each component its type and an identifier, the "field identifier", to denote it. The scope of a field identifier is the innermost record in which it is defined. A field may be defined as a previously defined record type. In the following descriptions, a definition of each data type or variable will be given followed by a description of the type or variable.

The important data structures developed for the program will now be described. These data structures allow the representation of the problem in a format solvable by a computer which is consequently accessible to a much larger range of people than would be possible by individual consultation with an expert. The data types allow the appropriate manipulation of information as found in a typical traveler's itinerary information relative to jet lag countermeasures.

Figure 11:
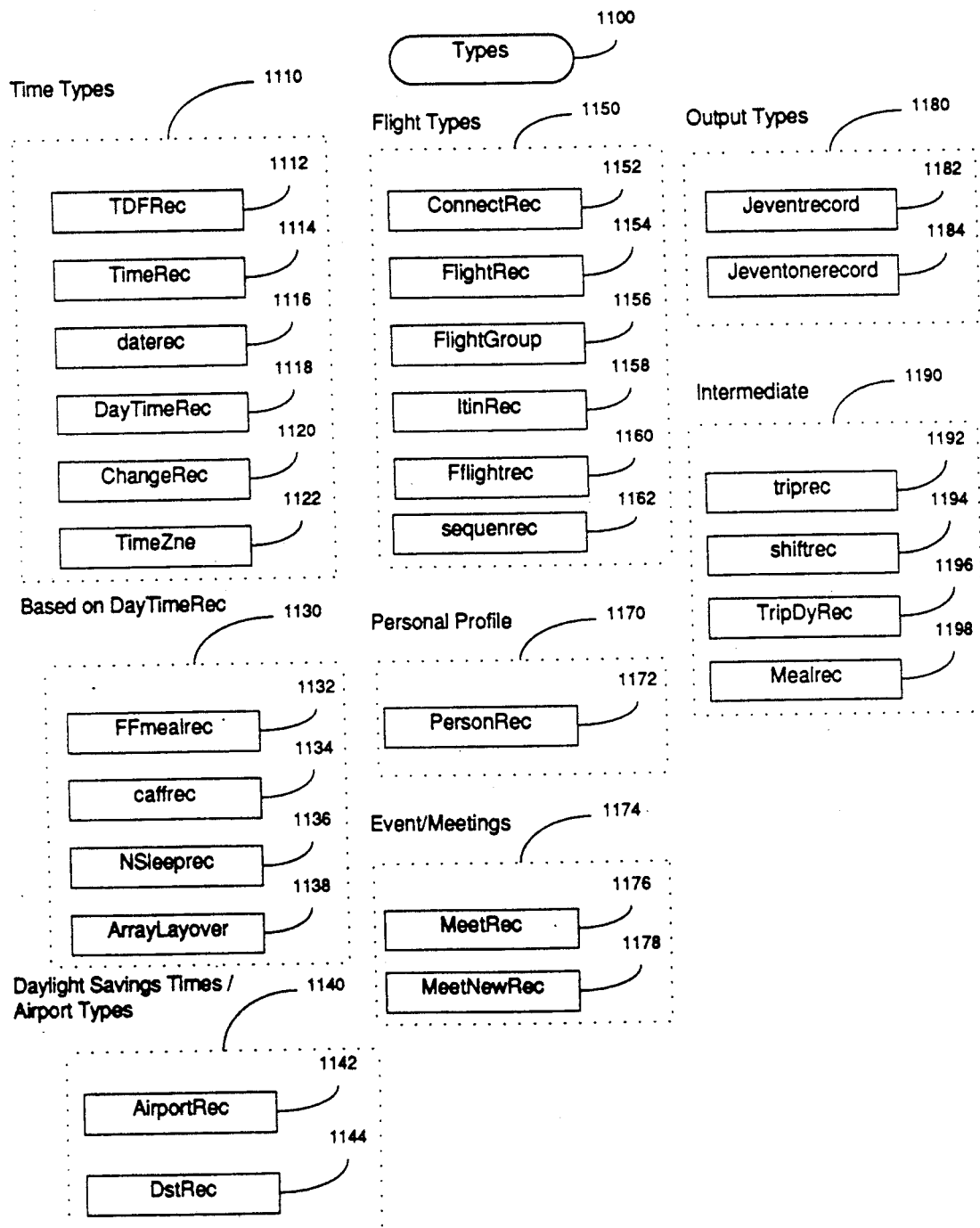
FIG. 11 is an illustration of data type structures in the program.

An overview of the major data types groupings is shown in FIG. 11. The Time Types 1110 related to time and the Time Differential Factor (TDF), are used to relate the local time at one location to the local time at any other location in the world. Data type DayTimeRec 1130 will form the basis of pinning the location of events in a continual time line relative to any time zone in the world. The DST data types 1140 are used for accessing daylight savings time. Flight types 1150 are used to store a description of flight information types. Personal profile type 1170 expands upon the typical airline profile by keeping information on preferred sleeping, meal, and meeting times. Event/meeting type 1174 is used to store the information for important events or meetings. Output types 1180 are used for converting information into the daily agenda. Various intermediate calculation values are stored in intermediate types 1190.

The Time Type data structures include TDFRec, TimeRec, daterec, DayTimeRec, ChangeRec, and TimeZne, which will now be described.

```
TDFRec = RECORD
    TDFHour: integer;
    TDFquarter: integer;
END;
```

The TDFRec 1112 is able to hold not only the time differential factor from Greenwich Mean Time in hours (TDFHour), but is also able to break out quarter hours in TDFquarter as found at some locations in the world.

```
TimeRec = RECORD
    Hour: integer;
    Minute: integer;
    TDF: TDFRec;
END;
```

The TimeRec 1114 holds the time in hours and minutes as well as the TDF for the location.

```
daterec = RECORD
    day: integer;
    month: integer;
    year: integer;
    dateJulian: longint;
END;
```

The daterec 1116 holds the date in separate day, month, and year integers, as well as in the Julian Date in a variable called dateJulian. The Julian Date is useful in allowing dates to be added and subtracted.

```
DayTimeRec = RECORD
    time: TimeRec;
    JulianDate: LongInt;
END;
```

The DayTimeRec 1118 holds the time of an event in the previously described TimeRec format, but also includes the Julian Date so the time can also fit into a continual time line.

```
ChangeRec = RECORD
    ShiftOnLeg: BOOLEAN;
    LegShift: TDFRec;
    TargetLeg: integer;
    TargetShift: TDFRec;
    BaseLeg: integer;
    BaseShift: TDFRec;
    LongDiet: BOOLEAN;
    nites: integer;
    daysIn: integer;
    datepre3,datepre2,datepre1,dateleave,
        datearrive: daterec;
END;
```

The ChangeRec 1120 keeps track of information needed for any trip, but especially those with more than one stop. ShiftOnLeg is a flag which says whether a time shift is to take place on that particular leg. LegShift holds the TDF difference from the previous leg. TargetLeg holds the nubmer of the leg indicating the effective time zone the traveler should be living on. TargetShift holds the TDF of the TargetLeg. BaseLeg holds the number of the leg holding the TDF the traveler last lived on. BaseShift holds the TDF difference between the TDF of the BaseLeg and the TDF of the TargetLeg. LongDiet is a flat indicating whether the short (2-day) or long (4-day) preparatory dietary regimen should be followed. DaysIn holds the number of days into the traip while datepre3, datepre2, datepre1, dateleave, and datearrive hold the days surrounding the time change.

```
TimeZne = RECORD
    ZnStdIDL: integer;   (*International Date
                           Line*)
    ZnStdGMT: integer;   (*Greenwich Mean
                           Time*)
END;
```

The TimeZne record 1122 includes ZnStdIDL which holds a time zone as measured from the International Date Line, and ZnStdGMT, which holds a time zone as measured from Greenwich Mean Time.

The DayTimeRec record types 1130 include FFmealrec, caffrec, NSleeprec, and ArrayLayover, which will now be described.

```
FFmealrec = RECORD
    fastfeast: integer;
    meal: ARRAY[1..3] OF Daytimerec;
END;
```

The FFmealRec 1132 holds information about the meal types in the days surrounding the time change. Fastfeast indicates whether the meals on that day are feast, fast, or normal meals. Finally, meal holds the times of the meals in the previously defined DayTimeRec format.

```
caffrec = RECORD
    hourstart: DayTimeRec;
    hourend: DayTimeRec;
END;
```

The caffrec 1134 holds information about caffeine times. Hourstart and hourend hold the times to start having caffeine and stop having caffeine, respectively, in the previously defined DayTimeRec format.

```
NSleeprec = RECORD
    hourstart: DayTimeRec;
    hourend: DayTimeRec;
END;
```

The NSleeprec 1136 holds information about sleep times. Hourstart and hourend hold the times to start sleep and end sleep, respectively, in the previously defined DayTimeRec format.

```
ArrayLayover = ARRAY[1..MAXCONNECT] OF
                 NSleeprec;
```

The ArrayLayover 1138 holds information about sleep times and potential conflicts with sleep and the required activities during flight layover times. MAXCONNECT is set to the value of 2.

The Daylight Savings Time/Airport types 1140 will now be described.

```
POINTERS = ↑ AirportRec;
AirportRec = record
   INFO: string40;
   AirCode: string04;
   ZoneNumber: integer;
   DSTNumber: integer;
   NEXT: POINTERS;
END;
```

AirportRec 1142 holds a linked list data type of airport information. INFO holds a description of the airport, while AirCode holds the airport letter code. ZoneNumber indicates the number of time zones from the International Date Line. DSTNumber holds the location in the Daylight Savings Time database of the country/portion of a country where this airport can be found.

```
DstPOINTERS = ↑ DstRec;
DstRec = record
   INFO: string40;
   ZoneNumber: integer;
   TDF: TDFRec;
   TDFdst: TDFRec;
   DSTStart: daterec;
   DSTEnd: daterec;
   count: integer;
   NEXT: DstPOINTERS;
END;
```

DstRec 1144 holds a linked list data type of daylight saving time information. TDF holds in a TDFRec format the time differential factor from Greenwich Mean Time during the standard time portion of the year. TDFdst holds in a TDFRec format the time differential factor from Greenwich Mean Time during the daylight savings time portion of the year. DSTStart and DSTEnd hold the starting and ending dates of daylight savings time in the previously defined daterec format.

Flight types 1150 includes ConnectRec, FlightRec, FlightGroup, ItinRec, Fflightrec, and sequenrec, which will now be described.

```
ConnectRec = RECORD
   NumOfConnection: integer;
   TotalConnection: integer;
END;
```

The ConnectRec 1152 keeps track of the number of connections in a flight and the total connections in a non-direct flight; 1 of 1 indicates direct flight, 1 of 2 indicates connections involved.

```
FlightRec = RECORD
```

```
   LocLeave,LocArrive: str40;
   AirCodeLeave,AirCodeArrive: str4;
   ZoneLeave,ZoneArrive: integer;
   dateleave,datearrive: daterec;
   TimeLeave,TimeArrive: TimeRec;
   FlyTime: integer; (* in minutes *)
   TimeChange: TDFRec;
   Airline: str40;
   AirlineCode,Airflight: str4;
   InfoConnect: ConnectRec;
END;
```

The FlightRec 1154 stores flight data. LocLeave and LocArrive hold the description of the departure and arrival locations, respectively, for the flight. AirCodeLeave and AirCodeArrive hold the airport codes for the departure and arrival locations, respectively, for the flight. ZoneLeave and ZoneArrive hold the time zones as measured from the International Date Line for the departure and arrival locations, respectively, for the flight. TimeLeave and TimeArrive hold the departure and arrival times, respectively, for the flight. FlyTime holds the flight time in minutes for the flight. TimeChange holds the TDF change between the departure and arrival locations, respectively, for the flight. Airline holds the airline name, AirlineCode holds the airline letter code, and Airflight holds the flight number for the flight. InfoConnect holds the information concerning to which connected leg of the flight the leg pertains.

```
FlightGroup = ARRAY [1..MaxConnect] OF
                FlightRec;
```

FlightGroup (1156) is an array that holds the connecting flights associated with a given departure to arrival flight.

```
ItinRec = RECORD
   Connection: FlightGroup;
   NumOfConnect: integer;
   LocLeave,LocArrive: str40;
   AirCodeLeave,AirCodeArrive: str4;
   ZoneLeave,ZoneArrive: integer;
   FlyTime: integer; (* in minutes *)
   TimeChange: TDFRec;
   NitesAt: integer;
   Important: BOOLEAN;
END;
```

The ItinRec 1158 stores itinerary data. Connection holds any flights associated with the flight from the original departure location to the ultimate arrival location. NumOfConnect holds the number of connections associated with the flight from the original departure location to the ultimate arrival location. LocLeave and LocArrive hold the description of the original departure and ultimate arrival locations, respectively, for the flight. AirCodeLeave and AirCodeArrive hold the airport letter codes for the original departure and ultimate arrival locations, respectively, for the flight. ZoneLeave and ZoneArrive hold the time zones as measured from the International Date Line, for the original departure and ultimate arrival locations, respectively, for the flight. FlyTime holds the total flight time, in minutes, for the flight, including layover time. TimeChange holds the TDF change between the original departure and ultimate arrival locations, respectively, for the flight. NitesAt indicates the number of nights at the given arrival destination. Important indicates an important event or meeting is to occur at the destination.

```
Fflightrec = RECORD
        codedepart : string04;
        timedepart : Daytimerec;
        codearrive : string04;
        timearrive : Daytimerec;
END;
```

The Fflightrec 1160 holds flight information for an individual flight using the DayTimeRec format for date and time information. Codedepart holds the airport letter code for the departure airport. Timedepart holds the departure time in the previously defined DayTimeRec format. Codearrive holds the airport letter code for the arrival airport. Timearrive holds the arrival time in the previously defined DayTimeRec format.

```
sequenrec = RECORD
        flightname : string06;
        numofflights : integer;
        flightinfo : ARRAY[1..MAXFLIGHTS] OF
                    Fflightrec;
END;
```

The sequenrec 1162 holds flight information for the connecting flights going from the original departure to the ultimate arrival location. Numofflights holds the number of connecting flights in the flight sequence, and flightinfo holds an array of flight information in the previously defined Fflightrec format. MAXFLIGHTS is set to the value of 3.

```
PersonRec = RECORD
        Name: string[40];
        Company: string[40];
        StAddress: string[40];
        City: string[40];
        State: string[20];
        ZIP: string[10];
        Country: string[20];
        Telephone: string[20];
        PrefBed: TimeRec;
        PrefSleep: TimeRec;
        PrefFstMeet: TimeRec;
        PrefLstMeet: TimeRec;
        PrefBreakfast: TimeRec;
        PrefLunch: TimeRec;
        PrefSupper: TimeRec;
        SocialSecurity: string[20];
        Passport: string[20];
        Visa No: string[20];
        NotifyPerson: string[40];
        BloodType: string[10];
        Immunization: string[50];
        Allergies: string[100];
        FoodAllergies: string[100];
END;
```

The PersonRec 1172 holds the individual traveler profile. The ability to define time preferences for activities for the individual traveler then base recommendations for any traveler's anti-jet lag regimen distinguishes this program from any prior art. Specifically, in the previously described TimeRec format, the following data is held for a traveler. PrefBed holds the preferred bedtime. PrefSleep holds the preferred number of hours of sleep. PrefFstMeet holds the preferred earliest time to have a meeting. PrefLstMeet holds the preferred latest time to have a meeting. PrefBreakfast holds the preferred time to have breakfast. PrefLunch holds the preferred time to have lunch. PrefSupper holds the preferred time to have supper.

Event/meetings types 1174 include MeetRec and MeetNewRec, which will now be described.

```
MeetRec = RECORD
        Location: str255;
        zone: integer;
        date: daterec;
        time: TimeRec; (*TimeOfDay;*)
        duration: integer; (* in days *)
        Important: BOOLEAN;
END;
```

The MeetRec 1176 stores meeting and/or important event data. Location hold the name of the meeting place. Zone holds the time zone of the meeting as measured from the International Date Line. Date holds the date the meeting is to start. Time holds the time of day the meeting is to start. Duration holds the number of days needed for meetings. Important holds a flag indicating that the meetings requires peak performance from the individual.

```
MeetNewRec = RECORD
        daysIn: integer;
        leg: integer;
        FirstMeet,LastMeet,MeetDuration,
                NumOfDays: integer;
        END;
```

The MeetNewRec 1178 holds meeting information derived from MeetRec, above. DaysIn holds the number of days into the trip leg that first meeting starts (A full nights sleep is required to count as a day). Leg holds the number of the trip leg this meeting is found in. Finally FirstMeet holds the hour of first meeting, LastMeet holds the last available hour to finish meetings on any day, MeetDuration holds the hours in one day needed for meetings, and NumOfDays holds the number of meeting days with these requirements.

Output types 1180 include Jeventrecord and Jeventonerecord, which are used to translate the information for the days surrounding the time shift into a hour-by-hour daily agenda format.

```
JeventPtr = ↑ Jeventrecord;
Jeventrecord = RECORD
        Start : DayTimeRec;
        Finish : DayTimeRec;
        TimeInt : integer;
        DayNum : integer
        IDLZone : integer
        DstOn : integer
        ActualTDF : TDFRec
        Code : str4;
        Airport : str4;
        Last, Next : JEventPtr;
END;
Jeventonerecord = RECORD
        Start : DayTimeRec;
        Finish : DayTimeRec;
        TimeInt : integer;
        DayNum : integer
        IDLZone : integer
        DstOn : integer
        ActualTDF : TDFRec
        Code : str4;
        Airport : str4;
END;
```

The type Jeventrecord 1182 holds a linked list with information regarding events (usually zeitgebgers or flights) that must be scheduled for a travelers anti-jet lag regimen. Start and Finish hold the starting and finishing times in the previously described DayTimeRec format. TimeInt holds the time interval of the day in which the event is located. DayNum holds the number of the day surrounding the time change. IDLZone holds the international date line time zone. DstOn indicates whether daylight savings time is on or off. ActualTdf holds the TDF that the event occurs at. Code holds the type of event occurring, and when appropriate, Airport holds the airport letter code for the location. Last and Next hold pointers to the previous and next Jeventrecords in computer memory. The type Jeventonerecord 1184 holds the same information as Jeventrecord but without any pointers.

Intermediate type 1190 include triprec, shiftrec, Trip-DyRec, and Mealrec, which will now be described.

```
triprec = RECORD
            depart : DayTimeRec;
            arrive : DayTimeRec;
         END;
```

The triprec 1192 holds the time of departure and arrival in the previously described DayTimeRec format.

```
shiftrec = RECORD
             TDF: TDFRec;
             nites: integer;
             daysIn: integer;
             Important: boolean;
           END;
```

The shiftrec 1194 is used for calculating time changes for each leg. TDF holds the time change from the previous leg. Nites holds the number of nights at this leg. DaysIn holds the number of days into the total trip upon which this leg starts. And Important designates that an important event is to happen on this leg.

```
TripDyRec = RECORD
              preday3, preday2, preday1, leaveday,
                  arriveday : longint;
              datepre3, datepre2, datepre1, dateleave,
                  datearrive : daterec;
              Spreday3, Spreday2, Spreday1, Sleaveday,
                  Sarriveday : str10;
            END;
```

The TripDyRec 1196 holds the dates surrounding the time change. Preday3, preday2, preday1, leaveday, and arriveday hold the days surrounding the time shift day, in Julian Date format. Datepre3, datepre2, dateprel, dateleave, and datearrive hold the days surrounding the time shift day in the previously defined date format. Spreday3, Spreday2, Spredayl, Sleaveday, and Sarriveday hold the names of the days surrounding the time shift day.

```
Mealrec = RECORD
            mealpre3, mealpre2, mealpre1, mealshift,
                mealpostshift: integer;
          END;
```

The Mealrec 1198 holds meal types (Feast, Fast, or Normal) for the days surrounding the time shift.

Figure 12A:
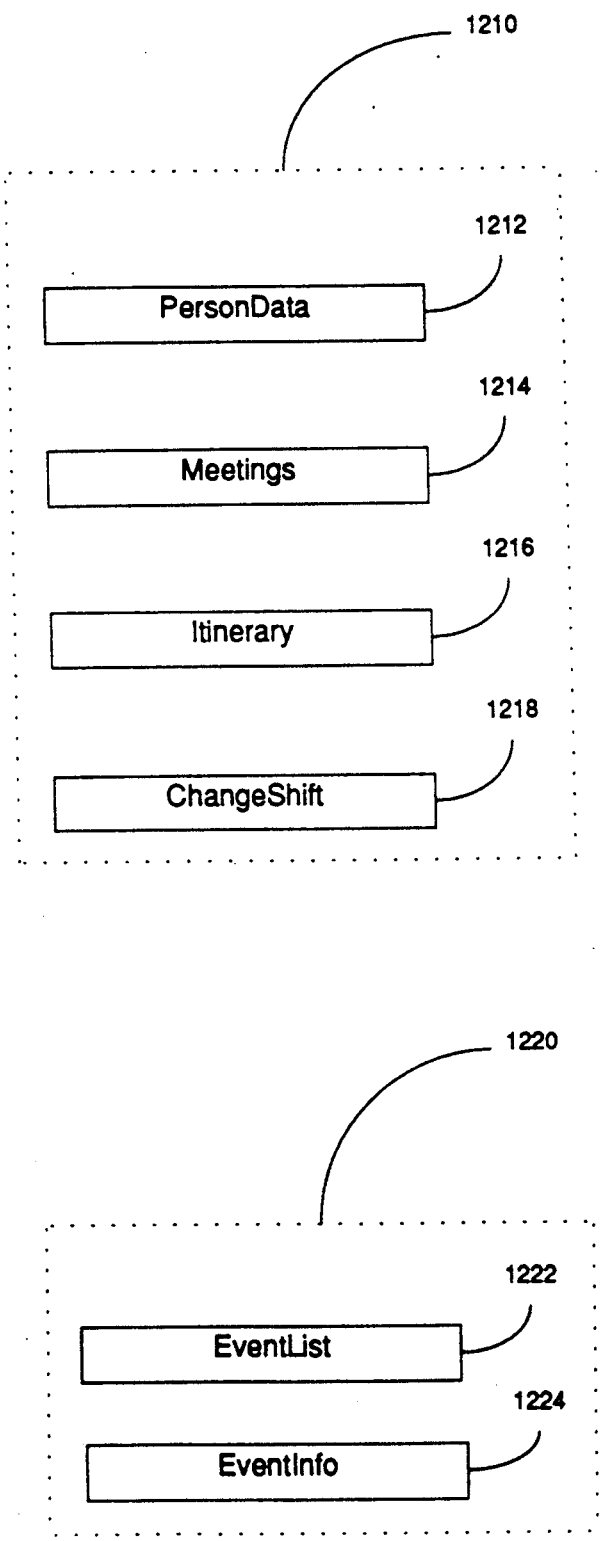
FIGs. 12a and 12b are illustrations of variables used in the program.

As described above, the program variables are defined using the above defined types. Referring to FIG. 12a, the key input variables will be described. Input variables 1210 include PersonData, Meetings, Itinerary, and ChangeShift.

PersonData: PersonRec;

This PersonData 1212 input information is initially entered from the input screens shown in FIGS. 1a, 1b, and 1c hereinabove. It is the information from FIG. 1b (preferred times) that gives the program the ability to adjust the output recommendations for the individual traveler. These values are initially set for an average person, but after modification they can be saved to a passenger profile disk file for future access.

Meetings: ARRAY [1..MAX_MEETINGS] OF MeetRec;

The Meetings variable 1214 holds events and/or meetings which can be classified by importance. MAX_MEETINGS is set to a value of 9. The entry screen for this information is shown in FIG. 2. This information is saved as part of a given trip.

Itinerary: ARRAY [1..MAX_LEGS] OF ItinRec;

The Itinerary input variable 1216 holds the flights for the given trip. MAX_LEGS is set to a value of 9. The entry screen for the legs of the trip is shown in FIG. 3. The entry screen for the actual flight times, flight numbers, and any connecting flights for a leg is shown in FIG. 4. This information is saved as part of a given trip.

ChangeShift: ARRAY [1..MAX LEGS] OF ChangeRec;

The ChangeShift variable 1218 holds the recommendations for the appropriate times to shift to a new time zone on a given, multiple destination trip. Although calculated according to the rules of the system, an editing screen for the information is shown in FIG. 5. This allows the traveler, if necessary, to override the number of days to be used for the preparatory diet and for the actual shifting legs.

EventList : JeventPtr;

EventInfo : Jeventonerecord;

Referring to FIG. 12a, major output variables 1220 are shown, including EventList and EventInfo. EventList 1222 is used to hold a list of the important activities related to jet lag countermeasures which are output as shown on the daily agenda illustrated in FIG. 9c. It allows these activities to be grouped by the period of the day in which they are found. They are sorted chronologically to give the traveler a list of appropriate measures to overcome jet lag. EventInfo 1224 holds the information for an individual event or activity.

Figure 12B:
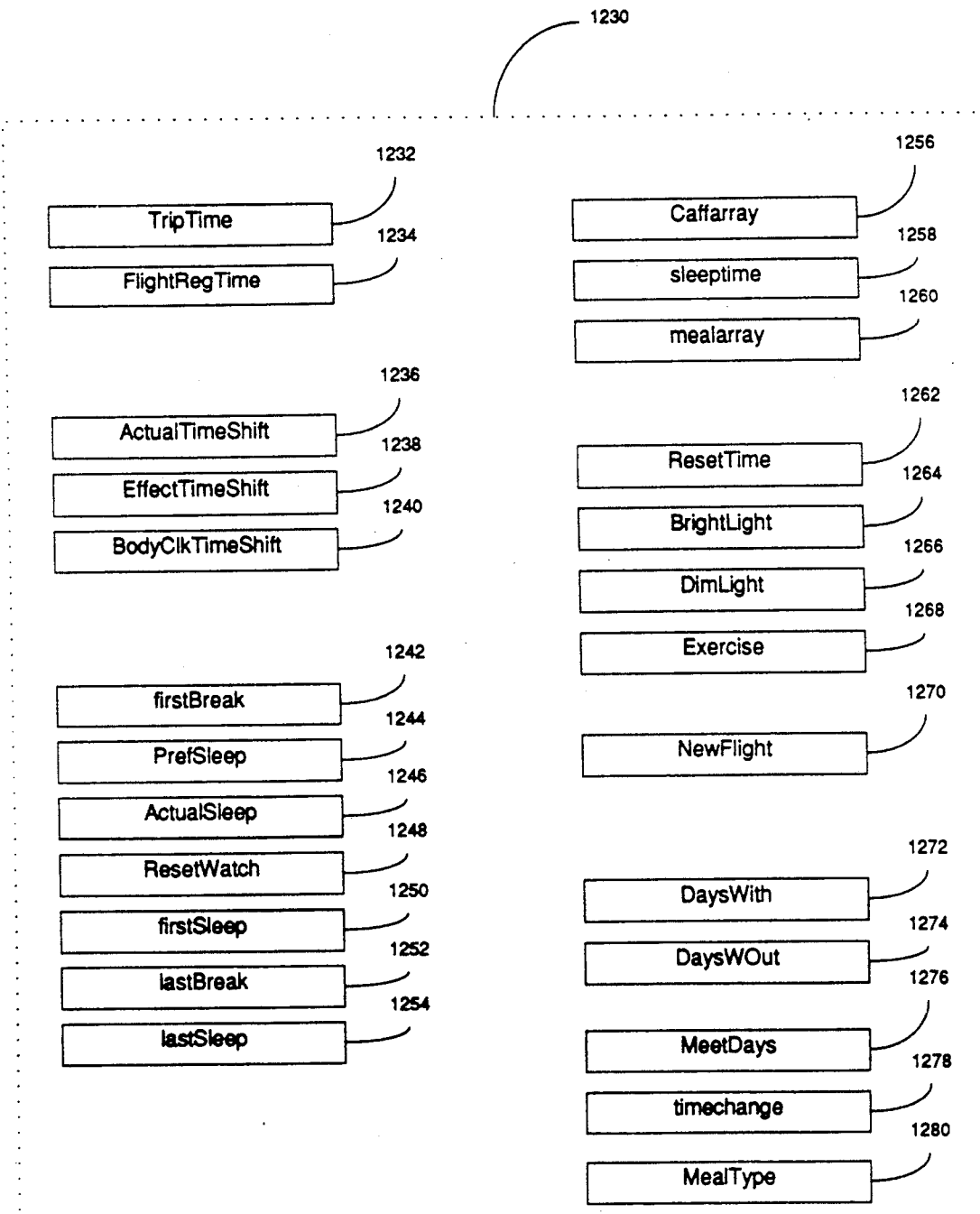

Referring to FIG. 12b, intermediate variables 1230 are shown. For each leg of the trip that will have a time shift, and consequently a daily agenda with anti-jet lag countermeasure recommendations, the variables, which include TripTime, FlightRegTime, ActualTimeShift, EffectTimeShift, BodyClkTimeShift, firstBreak, PrefSleep, ActualSleep, ResetWatch, firstSleep, lastBreak, lastSleep, Caffarray, sleeptime, mealarray, ResetTime, BrightLight, DimLight, Exercise, NewFlight, and MeetDays, are used to hold intermediate values, some of which appear in the hour-by-hour daily agendas.

TripTime : triprec;

FlightRegTime : TimeRec;

TripTime 1232 holds the final departure and arrival times in the previously described triprec format which is defined in DayTimeRec format. FlightRegTime 1234 holds the flight time between the final departure and arrival locations.

ActualTimeShift : TDFRec;

EffectTimeShift : TDFRec;

BodyClkTimeShift : TDFRec;

The ActualTimeShift 1236 is the time shift between departure and arrival locations of the given leg. For example, the time shift for a flight between New York City and Tokyo, normally +14 hours, is corrected for any changes due to Daylight Savings Time. The EffectTimeShift 1238 is the Effective Time Shift corresponding to a number equal to or between −12 and 12 hours. For example, the +14 hour Actual Time Shift is converted to a −10 Effective Time Shift. The BodyClkTimeShift 1240 is the time shift that will govern the anti-jet lag rules the traveler will follow during the time change. This is because the body can adapt more easily to large phase delays than to corresponding large phase advances. For example, a +11 hour phase advance is best accommodated by having the traveler adjust to a −13 hour phase delay.

firstBreak : Daytimerec;

PrefSleep : Daytimerec;

ActualSleep : Daytimerec;

ResetWatch : Daytimerec;

firstSleep : Daytimerec;

lastBreak : Daytimerec;

lastSleep : Daytimerec;

These variables in DayTimeRec format are important reference times in the development of the anti-jet lag regimen and its ability to adapt to various traveler time preferences. FirstBreak 1242 holds the "Break The Fast With Breakfast Destination Time" (B.T.F.W.B.D.T.) which is the time of the first breakfast on the assigned time zone of the destination, at the preferred breakfast hour. PrefSleep 1244 holds the preferred first time to go to sleep on destination time prior to the Break The Fast With Breakfast Destination Time meal. ActualSleep 1246 holds the actual first time to go to sleep on destination time prior to the B.T.F.W.B.D.T. meal. ResetWatch 1248 holds the time to reset the travelers watch to destination time. FirstSleep 1250 holds the first time to sleep after the B.T.F.W.B.D.T. meal. LastBreak 1252 holds the Last Breakfast on Departure Time prior to the B.T.F.W.B.D.T. meal. LastSleep 1254 holds the start of sleep immediately prior to the last breakfast on Departure Time prior to the B.T.F.W.B.D.T. meal.

Caffarray : ARRAY[1..NMAXDAYS] OF caffrec;
sleeptime : ARRAY[1..NMAXDAYS] OF Nsleeprec;
mealarray : ARRAY[1..NMAXDAYS] OF FFmealrec;
ResetTime : DayTimeRec;
BrightLight : Nsleeprec;
DimLight : Nsleeprec;
Exercise : Nsleeprec;
NewFlight : ARRAY[1..NMAXDAYS] OF sequenrec;

The variables Caffarray 1256, sleeptime 1258 and mealarray 1260 hold the time, duration, and special features of these zeitgebers on all the days surrounding the time change. NMAXDAYS is set to the value of 7. ResetTime 1262 holds the time to reset one's watch to the destination time zone. The variables BrightLight 1264, DimLight 1266, and Exercise 1268 hold information about these zeitgebers in the previously defined NSleeprec format. The variable NewFlight 1270 holds the times of flights on all the days surrounding the time change.

DaysWith, DaysWOut: ARRAY [0..MAX_LEGS] OF integer;

DaysWith 1272 and DaysWOut 1274 hold the number of days for each leg of the trip that are needed to alleviate the majority of jet lag symptoms, with and without the use of the recommended jet lag countermeasures, respectively.

MeetDays: ARRAY [1..totallegs] OF MeetNewRec;

MeetDays 1276 holds intermediate values derived from the meeting inputs. The values are used in calculated recommendations for multiple destination trips. Totallegs is set to the value of 9.

timechange: ARRAY [1..totallegs] OF shiftrec;

Timechange 1278 holds values consisting of the time change for each leg, the number of nights at the leg, the days into the trip this leg starts, and whether an important event is to happen on the leg.

MealType Mealrec;

MealType 1280 holds intermediate values used to recommend meal types (Feast, Fast, or Normal) for the days surrounding the time shift.

An overview of specific chronobiology rules incorporated into the system will now be given. A detailed description of the computer program incorporating these rules will then be given.

The key to the diet portion of a multiple zeitgeber plan is fasting, because it enhances sensitivity to food as a zeitgeber. In the normal circadian cycle, glycogen builds up to a fairly high level each day, at its highest point accounting for about 15% of liver weight. The glycogen level then goes down to about 2% of liver weight just before morning. Thus, in the natural glycogen cycle, breakfast acts as a signal of phase change to the body, telling it to start the glycogen storage phase. Breakfast for the fasting person is an even stronger signal of phase change. Thus, the "break the fast with breakfast destination time" is a major event in resetting a traveler's body clocks. Although it is not an exclusive effector in achieving the desired phase shift, it is the most convenient anchor/referential point for all of the other essential zeitgebers (light, drugs, oxygen, exercise, and social cues, none of which is to be neglected as subordinate to the reference point). The following rules are thus incorporated into the program in a manner which utilizes this reference point.

Rule 1. Methylxanthine drugs, including caffeine, theophylline, and theobromine contained in coffee, tea, and chocolate can be used to reset the biological clock by causing a phase shift—either a phase advance or a phase delay. The magnitude and direction of a phase shift caused by the methylxanthines depends on when the drugs are taken during the circadian cycle. Methylxanthine drugs cause little, if any, phase shift if taken between eight and one-half (8.5) and ten (10) hours after breakfast ("Normal Time"), so they should only be taken during the Normal Time in the days immediately prior to travel. On the day before the Break The Fast With Breakfast Destination Time ("B.T.F.W.B.D.T.") meal, methylxanthines facilitate a phase advance for the eastbound traveler if they are taken between eleven and one-half (11.5) and seventeen (17) hours after breakfast ("Evening"), or a phase delay for the westbound traveler if they are taken between breakfast and four and one-half (4.5) hours after breakfast departure time, ("Morning").

Accordingly, the program implements a number of rules specific to when an individual should ingest caffeine or other methylxanthine drugs. Specifically: An individual, who normally has breakfast at 7 am, should only ingest caffeine between the hours of 3:30–5 pm on the days before a flight. An individual should ingest anticipatory caffeine on the day before the B.T.F.B.W.D.T. meal between the hours of 6:30 pm–Midnight (old time) if the flight will cause a phase advance. An individual should ingest anticipatory caffeine on the last fast day before the B.T.F.B.W.D.T. meal between the hours of 7–11:30 am (old time) if the flight will cause a phase delay. Finally, the individual should not have any caffeine until one day past the break-the-fast breakfast unless otherwise specifically recommended. These times can be modified for variations in preferred breakfast time.

Rule 2. Physical and mental activity operate as important zeitgebers, and specific recommendations are made as to when a traveler should be active. Specifically, the traveler should ideally be inactive or asleep at 11 pm (or his preferred bedtime) destination time immediately prior to the B.T.F.B.W.D.T. meal.

Rule 3. The last fast day is cut short by skipping supper if the break the B.T.F.B.W.D.T. meal is within 6 hours of the old supper time. The last fast day is cut short by skipping lunch and supper if the B.T.F.B.W.D.T. meal is within 6 hours of the old lunch time.

Rule 4. Rule 4 determines whether caffeine should be consumed on the day of the B.T.F.W.B.D.T. meal. Specifically, if the recommended time for anticipatory caffeine on "old time" coincides with a phase on destination time when the traveler should be awake, then caffeine is recommended on the day of the B.T.F.W.B.D.T. meal. For example, 11 pm in San Francisco coincides with 8 am in Paris. Also if "zoneshift" is between −1 and −4 inclusively, or less than or equal to −9, then a second strong ingestion of caffeine is desirable on the day of the B.T.F.W.B.D.T. meal, at a time coinciding with the anticipatory caffeine timing (old time).

Rule 5. Rule 5 sets up the feast/fast meal days based on "zoneshift". This calculation is made for the day of the recommended time shift (MealShift), the day of arrival (MealPostShift), the day before the time shift (MealPre1), and each of the two days prior to "MealPre1" (MealPre2 and MealPre3).

Rule 6. The Phase Change Rule is implemented in Rule 6. "Phase advance" is what is experienced by crossing time zones flying from West to East. "Phase delay" is experienced by crossing time zones flying East to West. "Time Zone Difference" is the difference in the times of two locations. However, phase advance and phase delay are accommodated differently by the body and the recommended countermeasures differ. Particularly, the body has a much more difficult time adjusting to large phase advances than to equivalent phase delays. Accordingly, large phase advances (of eleven, twelve or thirteen hours) are treated as phase delays (of thirteen, twelve or eleven hours, respectively). For example, a +11 hour phase advance is treated as a −13 hour phase delay. Thus, a time zone difference of +11 hours would be treated as a phase delay in the body clock of −13 hours.

Rule 7. The traveler's watch is ideally reset at the time of sleep (destination) that immediately precedes the B.T.F.W.B.D.T. meal.

The method of the program used to generate a slide rule and/or daily agenda to recommend jet lag countermeasures is illustrated in FIGS. 13 thru 30. As will be evident from the description that follows, the program is advantageously structured to allow for changes to a subroutine without necessarily changing other parts of the program. Generally, each subroutine performs a single function and alters a limited, well-defined set of variables used by the other routines. Therefore, as new rules are added or old rules modified, the program can be easily updated.

Figure 13:
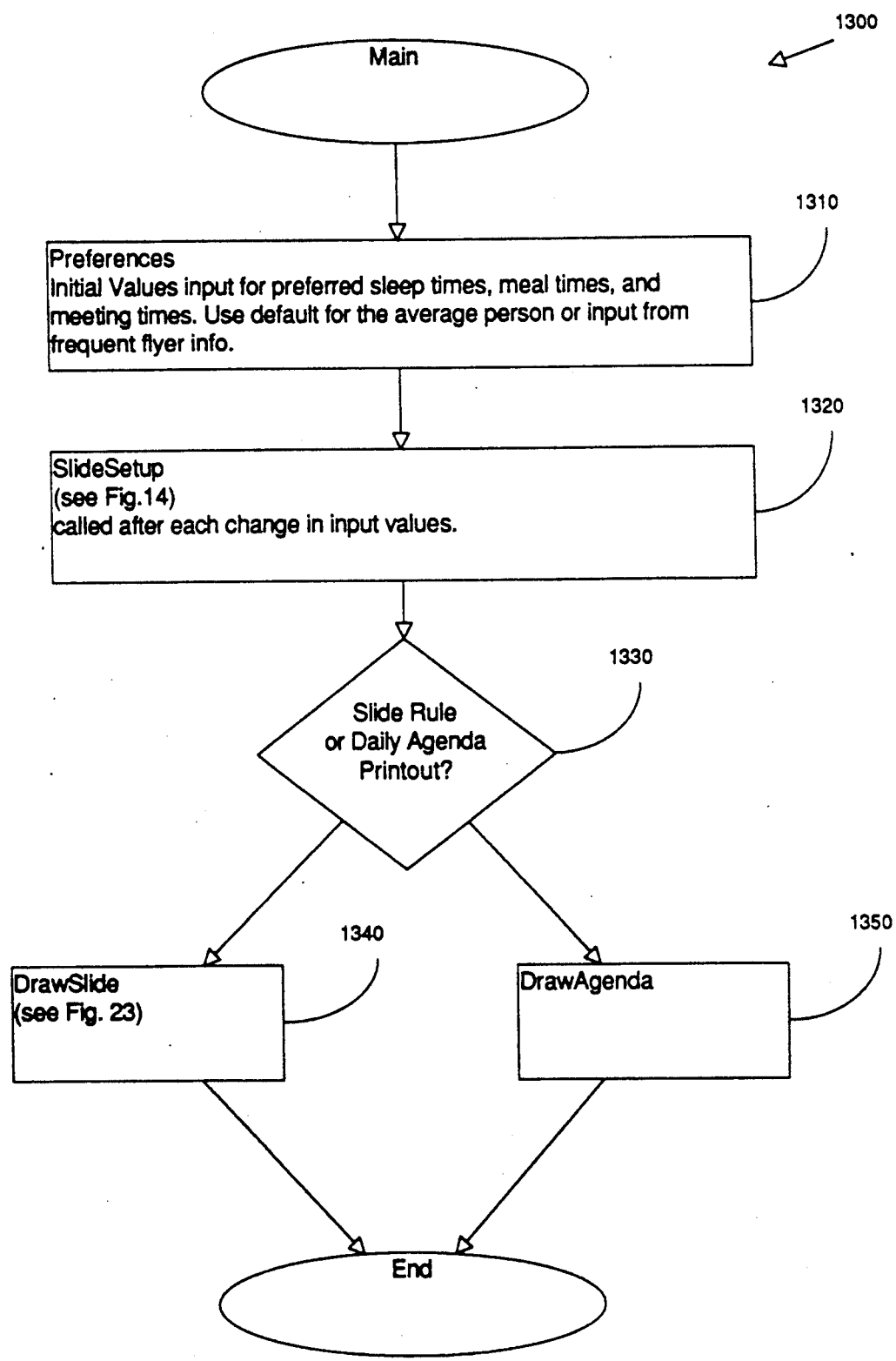
FIG. 13 is a logic flow diagram for the Main routine.

FIG. 13 shows the overall structure of the program, generally designated 1300. First at step 1310 the program calls a subroutine to get the individual traveler's preferences. This subroutine determines the initial values for preferred sleep times, meal times, and meeting times. As a starting point the schedule for an average person is used, or the schedule can be pulled from a particular traveler's profile. Execution then returns to the Main routine. Then at step 1320 the program calls the subroutine SlideSetup which determines all of the appropriate times over a continual time line for items such as times for coffee, meals, sleep, light, phase shifting, etc. Then, with all the needed times calculated and stored in appropriate data structures, the program determines in step 1330 whether a Slide Rule or a Daily Agenda is to be used to print the values in a format readable by the traveler. If a Slide Rule is chosen, DrawSlide 1340 is called, described in detail later with reference to FIG. 23. If a Daily Agenda is chosen, DrawAgenda 1350 is called. DrawAgenda puts the events and zeitgebers into the Jeventrecord format, sorts them in chronological order, and then prints them according to the time period in which they occur.

Figure 14:
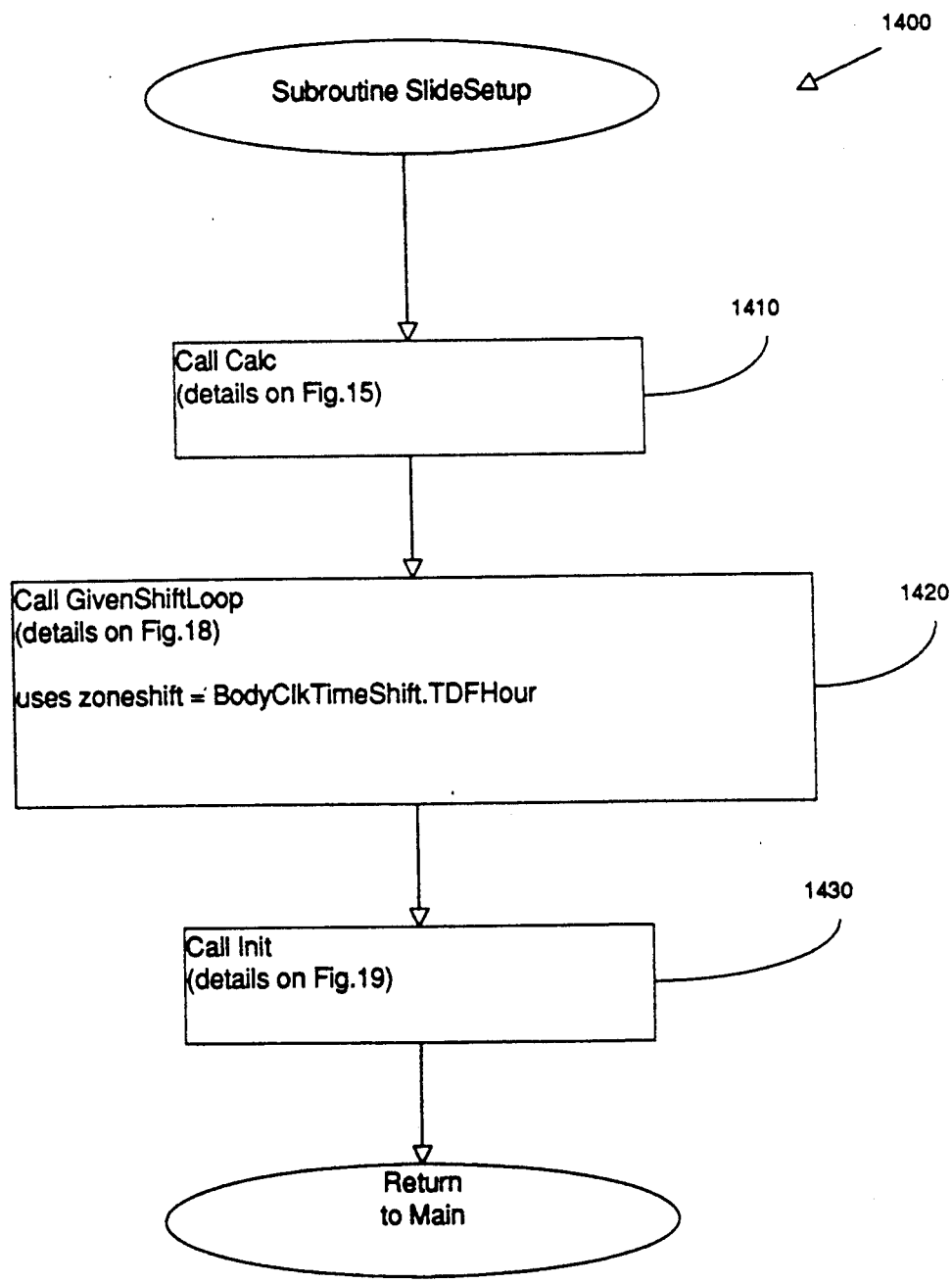
FIG. 14 is a logic flow diagram for the subroutine SlideSetup.

Referring to Fig.14 there is shown a flow chart for the subroutine SlideSetup, generally designated 1400.

This subroutine determines the values of all activities relevant to the minimization of jet lag. In the first step 1410 a subroutine Calc is called which calculates the ActualTimeShift, the EffectiveTimeShift, and the BodyClkTimeShift for the traveler between the chosen destinations. Having these values, the appropriate times and duration of activities are then calculated. The second step 1420 then sets zoneshift equal to BodyClkTimeShift and calls the subroutine GivenShiftLoop to determine which specific rules to apply to the given trip. In step 1430 the subroutine Init is called to initialize the data values for holding the timing and values of various zeitgebers. Execution then returns to the Main routine.

Figure 15:
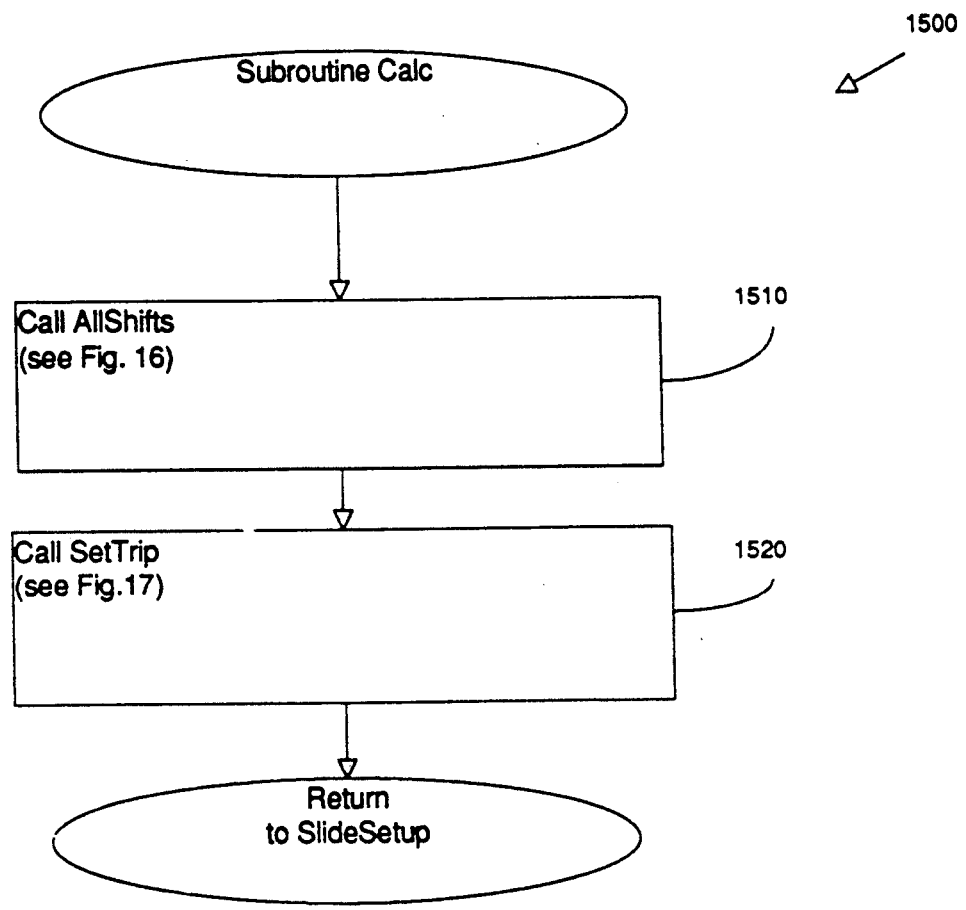
FIG. 15 is a logic flow diagram for the subroutine Calc.

Referring to FIG. 15 there is shown a flow chart for the subroutine Calc, generally designated 1500. In the first step 1510 a subroutine AllShifts is called which calculates the Actual Time Shift, the Effective Time Shift, and the BodyClkTime Shift for the traveler between the chosen destinations. Then the subroutine SetTrip 1520 is called to calculate the appropriate times and duration of activities. Execution then returns to the SlideSetup subroutine.

Figure 16:
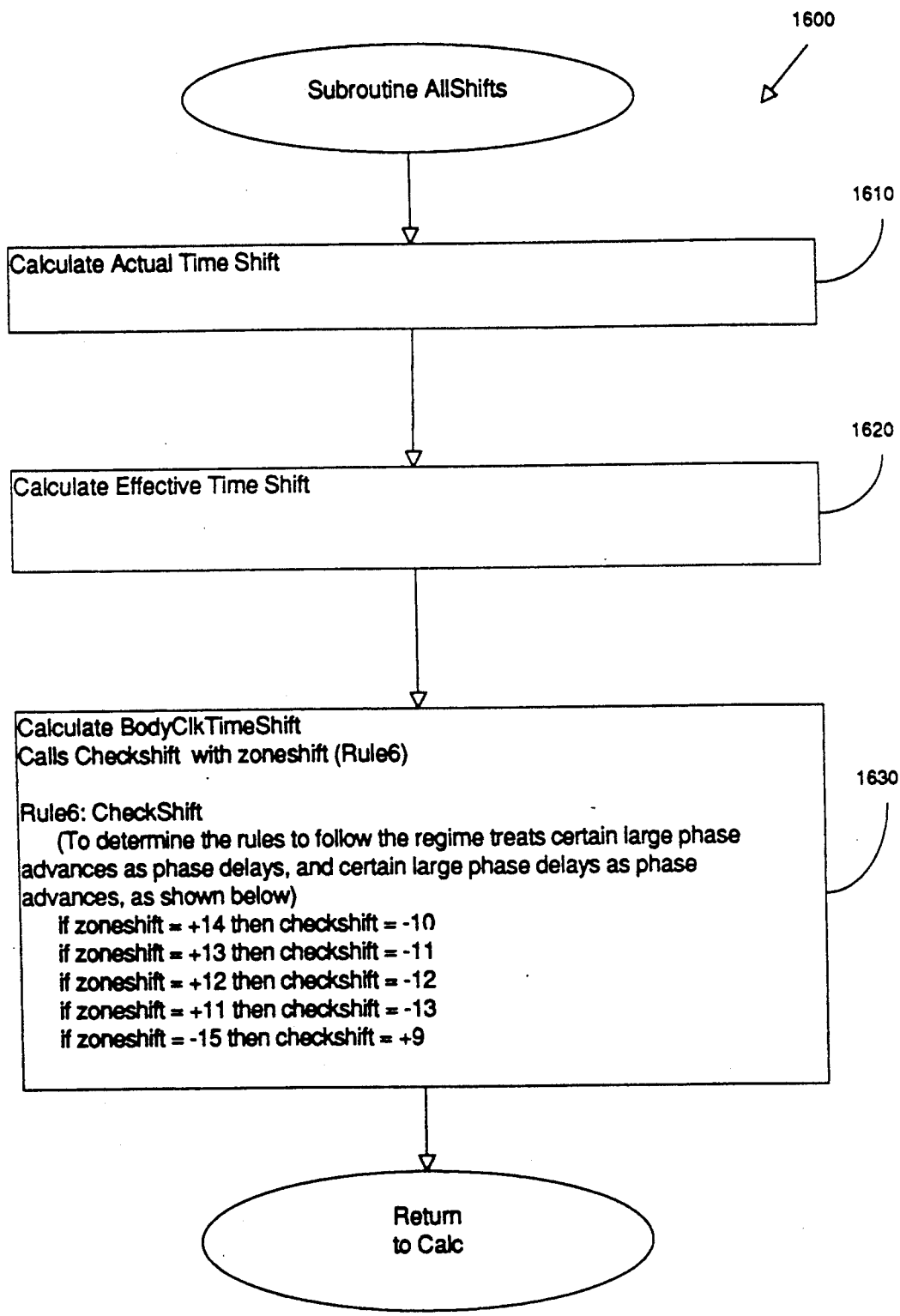
FIG. 16 is a logic flow diagram for the subroutine AllShifts.

Referring to FIG. 16 there is shown a flow chart for the subroutine AllShifts, generally designated 1600. In the first step 1610 it calculates the "Actual Time Shift" between departure and arrival locations of the given leg, corrected for any changes due to Daylight Savings Time. For example, the time shift for a flight between New York City and Tokyo is normally +14 hours. In step 1620 it calculates the "Effective Time Shift", by calling routine ShiftCheck. The Effective Time Shift is the number of hours difference between 2 locations disregarding any date difference. It always ends up between −12 and +12 hours. For example, the +14 hour Actual Time Shift is converted to a −10 Effective Time Shift. Finally, in step 1630 it calculates "BodyClkTimeShift" by calling the CheckShift routine. The CheckShift routine determines whether the phase delay or advance of the Effective Time Shift can be more effectively adapted to by the traveler by using a complementary phase change. If so, the BodyClkTimeShift is reset as is more fully described in the explanation of Rule6 provided below. BodyClkTimeShift is now used in the determination of recommended schedules and activities. Rule 6 (the Phase change rule) is implemented in the CheckShift routine. It determines the rules to follow for large phase advances and phase delays. Accordingly, large phase advances (plus ten, eleven, twelve or thirteen hours) are treated as phase delays (minus fourteen, thirteen, twelve or eleven, respectively). For example, a +11 hour phase advance is best accommodated by having the traveler adjust to a −13 hour phase delay. Thus, a time zone difference of +11 hours would be treated as a phase delay of −13 hours. Large phase delays (minus fifteen hours) are treated as phase advances (plus nine, respectively). The inclusion of time shifts greater than 12 hours allows for additive time changes sometimes found in multiple leg itineraries. Execution then returns to the Calc subroutine.

Figure 17:
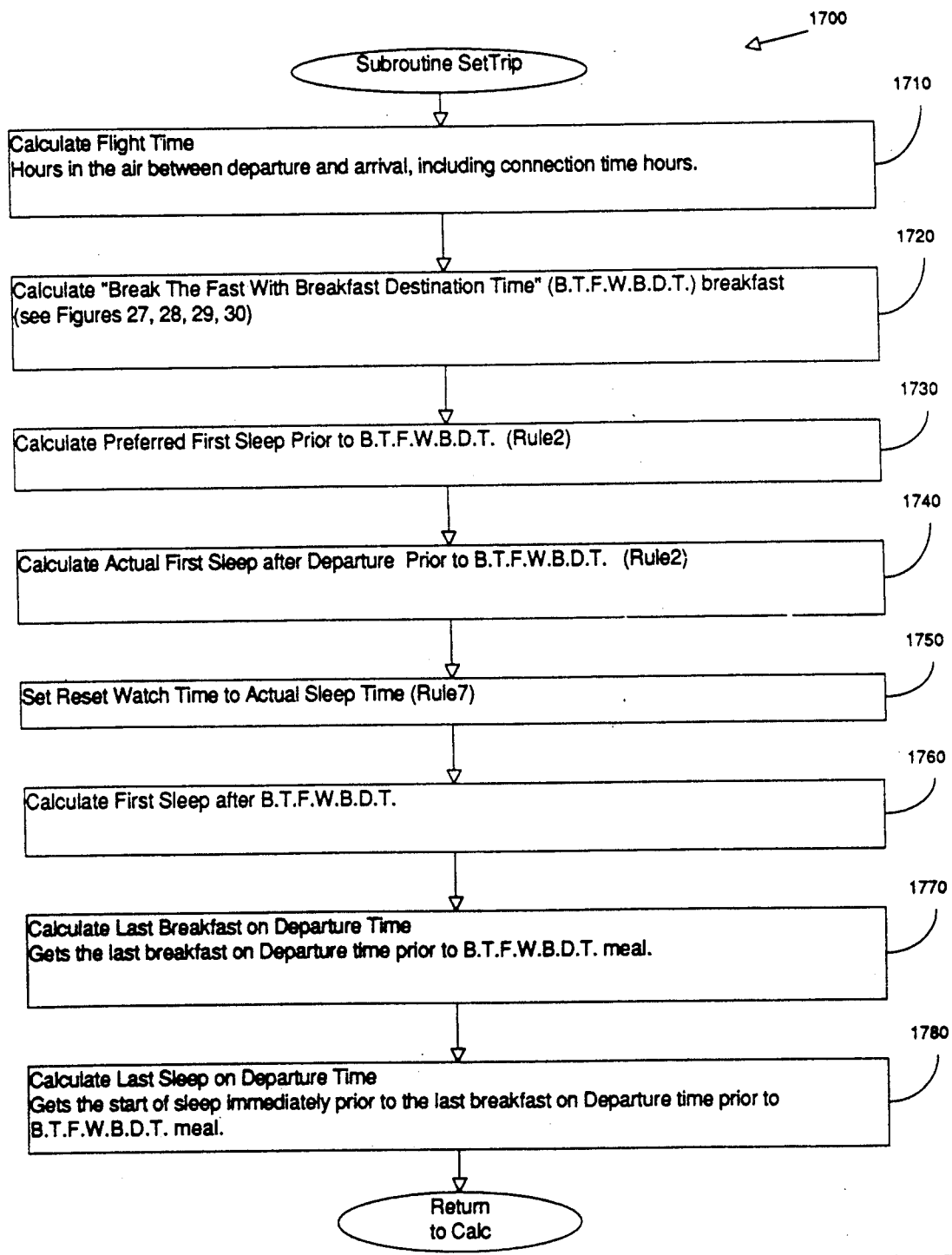
FIG. 17 is a logic flow diagram for the subroutine SetTrip.

Referring to FIG. 17 there is shown a flow chart for the subroutine SetTrip generally designated 1700. In the first step 1710, it calculates the flight time between departure and arrival for the leg. This includes the hours in the air for each of any connecting flights and connection time hours on the ground. Then in step 1720 it calculates the "Break The Fast With Breakfast Destination Time" (B.T.F.W.B.D.T.) meal which is the time of the first breakfast on the assigned time zone of the destination at the preferred breakfast hour. The method for calculating the B.T.F.W.B.D.T. meal is described in detail later with reference to FIGS. 27, 28, 29, and 30. Then in step 1730 it calculates the preferred first time to go to sleep on destination time prior to the B.T.F.W.B.D.T. meal (Rule 2). Then in step 1740 it calculates the actual first sleep on destination time prior to the B.T.F.W.B.D.T. meal (Rule 2). It starts with the preferred First Sleep Prior to B.T.F.W.B.D.T., and when appropriate if the departure comes after this time, the time to actually go to sleep is set to the departure time. Rule 2 states that physical and mental activity operate as important zeitgebers, and specific recommendations are made as to when a traveler should be active. Specifically, the traveler should ideally be inactive or asleep at 11 pm (or his preferred bedtime) destination time immediately prior to the B.T.F.W.B.D.T. meal. Then in step 1750 it sets the Reset Watch Time to the Actual Sleep Time (Rule 7). Then in step 1760 it calculates the First Sleep after B.T.F.W.B.D.T. using the arrival time TDF and Julian Date in conjunction with the personal preferred bedtime. Then in step 1770 it calculates the Last Breakfast on Departure Time prior to the B.T.F.W.B.D.T. meal. Finally in step 1780 it calculates the start of sleep immediately prior to the Last Breakfast on Departure time prior to the B.T.F.W.B.D.T. meal. These times are all important reference points for determining the timing of other activities. Execution then returns to the Calc subroutine.

Figure 18:
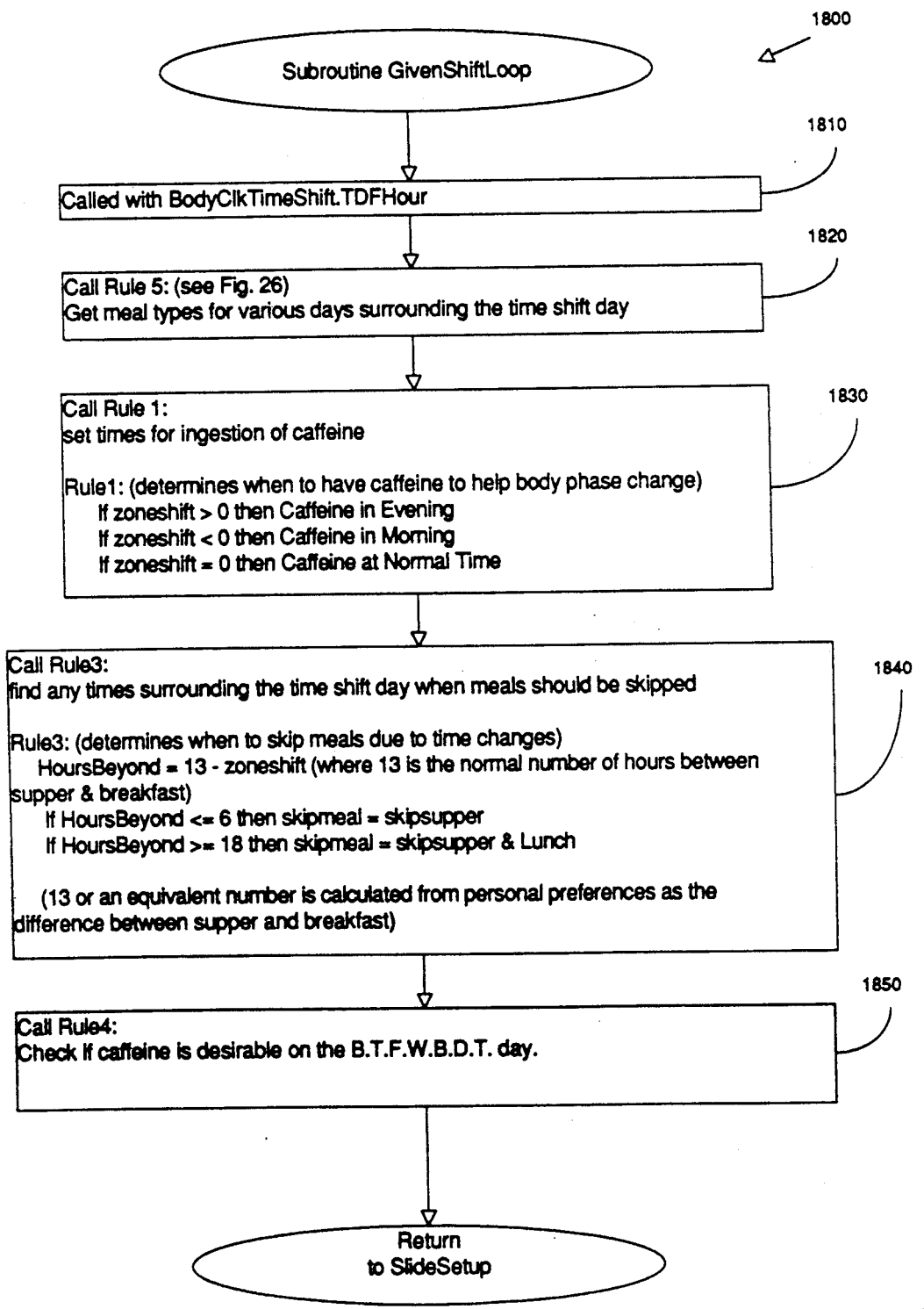
FIG. 18 is a logic flow diagram for the subroutine GivenShiftLoop.

Referring to FIG. 18 there is shown a flow chart for the subroutine GivenShiftLoop, generally designated 1800. This routine is called with a variable "zoneshift" set to BodyClkTimeShift.TDFHour 1810. In the first step 1820 it calls Rule 5 to calculate meal types (feast, fast, or normal) for each day surrounding the time shift day, as is more fully described in the explanation of Rule 5 (FIG. 26) provided below. Then in step 1830 it calls Rule1 to set the times for ingestion of caffeine. Rule1 determines when caffeine is appropriate based on whether the traveler is experiencing phase advance or phase delay. Specifically, if the zoneshift parameter is greater than zero (zoneshift>0), corresponding to a phase advance, caffeine is recommended in the Evening. If the zoneshift parameter is less than zero (zoneshift<0), corresponding to a phase delay, caffeine is recommended in the Morning. Finally, if the zoneshift parameter is equal to zero (zoneshift=0), corresponding to no phase shift, caffeine is recommended at the Normal Time. The caffeine time definitions are as follows: ("Normal Time") eight and one-half (8.5) to ten (10) hours after breakfast; ("Evening") eleven and one-half (11.5) to seventeen (17) hours after breakfast; ("Morning") breakfast to four and one-half (4.5) hours after breakfast. Then in step 1840 it calls Rule 3 to determine when certain meals on the last fast day should be skipped. Specifically, a parameter "HoursBeyond" is calculated by subtracting "zoneshift" from 13, the normal number of hours between supper and breakfast. If HoursBeyond is equal to or less than 6, the skipmeal parameter is set to "skip supper". If HoursBeyond is equal to or greater than 18, the skipmeal parameter is set to "skip supper and lunch". Then in step 1850 it calls Rule4 to determine the times for caffeine ingestion on the day/days after the time shift. Specifically, if the recommended time for anticipatory caffeine on old time coincides with a phase on destination time when the traveler should be awake, then caffeine is recommended on the day of the B.T.F.W.B.D.T. meal. For example, 11 pm in San Francisco coincides with 8 am in Paris. Also if "zoneshift" is between −1 and −4 inclusively, or less than or equal to −9, then a second strong ingestion of caffeine is desirable on the day of the B.T.F.W.B.D.T. meal, at a time coinciding with the anticipatory caffeine timing (old time). Execution then returns to the SlideSetup subroutine.

Figure 19:
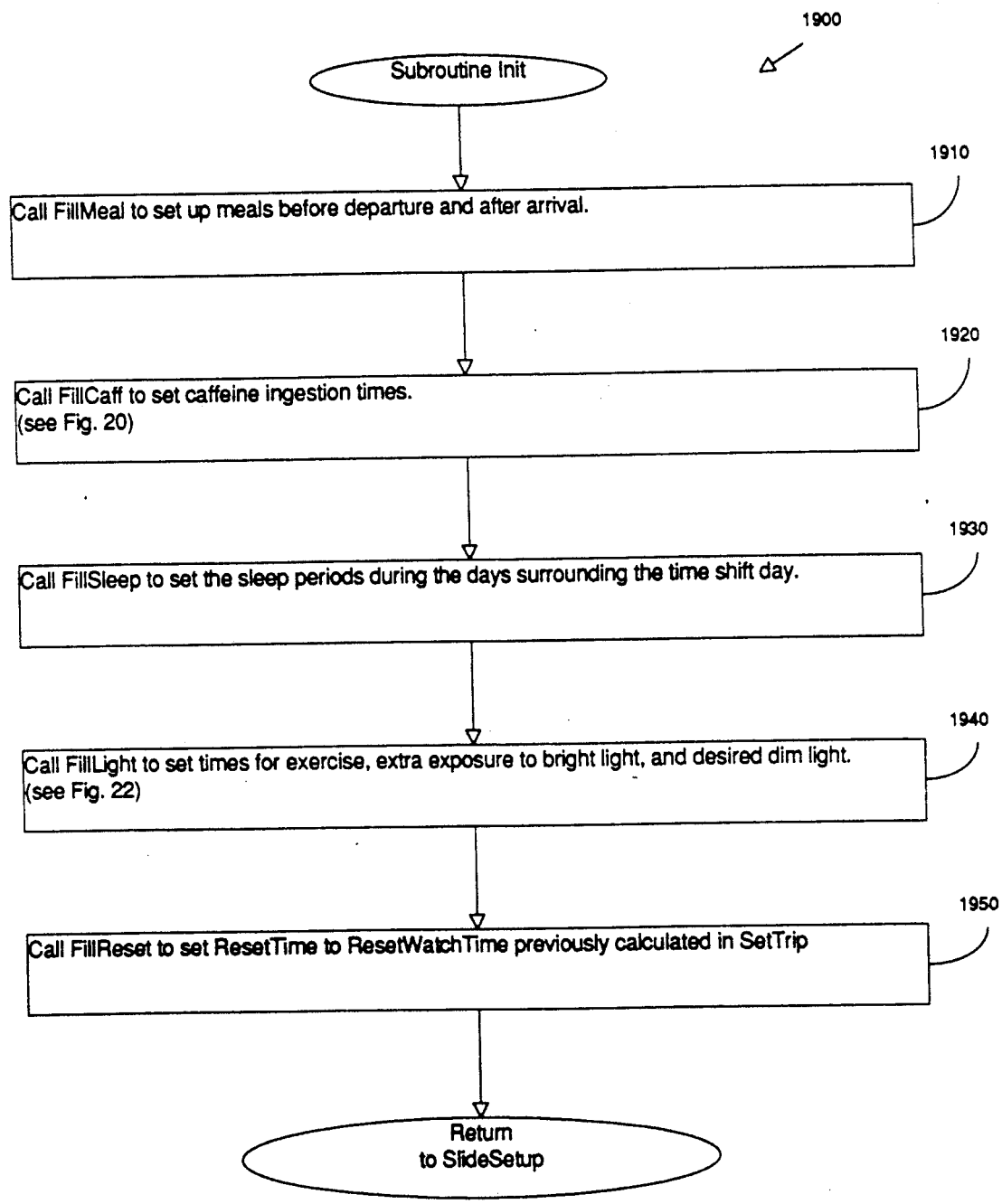
FIG. 19 is a logic flow diagram for the subroutine Init.

Referring to FIG. 19 there is shown a flow chart for the subroutine Init generally designated 1900. In the first step 1910 a subroutine FillMeal is called which first uses preferred meal times and types as well as the last breakfast on departure time to set up meals on departure time. It then uses preferred meal times, types, and first breakfast on arrival time to set up meals after the time shift to destination time. Then in step 1920 a subroutine FillCaff is called to set caffeine times using preferred meal times and the recommended times and duration of caffeine ingestion. Then in step 1930 a subroutine FillSleep is called which uses preferred sleep times and duration of sleep to set the sleep phases during the days surrounding the shift day. Then in step 1940 a subroutine FillLight is called to set the times surrounding the B.T.F.W.B.D.T. for exercise, extra exposure to bright light, and desired phases of dim light. Then in step 1950 a subroutine FillReset is called to set ResetTime to ResetWatchTime previously calculated in SetTrip. Execution then returns to the SlideSetup subroutine.

Figure 20:
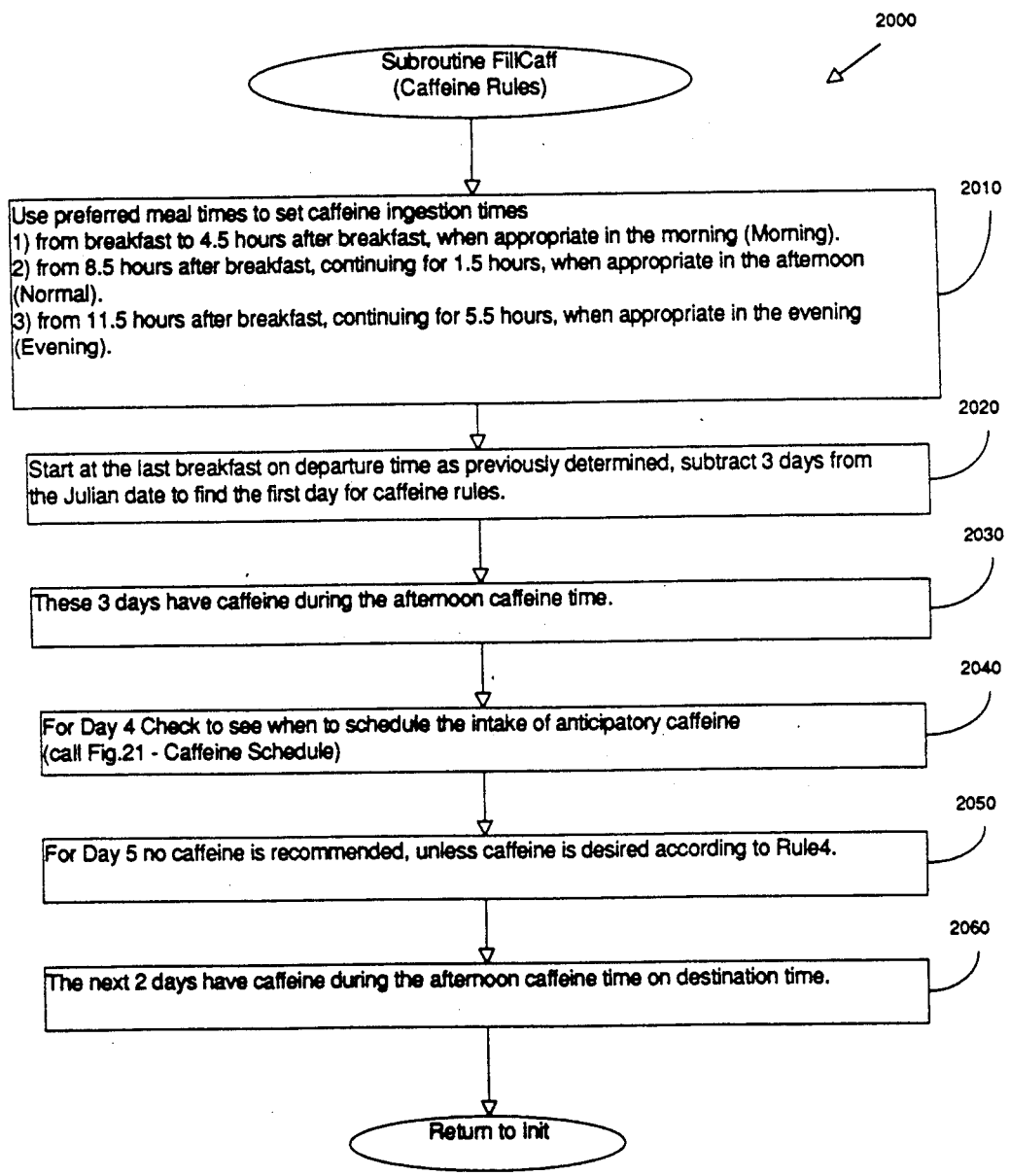
FIG. 20 is a logic flow diagram for the subroutine FillCaff Caffeine Rules.

Referring to FIG. 20 there is shown a flow chart for the subroutine FillCaff generally designated 2000. Step 2010 describes the criteria used to set caffeine times using preferred meal times and the recommended times and duration of caffeine ingestion. Briefly the caffeine ingestion criteria are (1) from breakfast to 4.5 hours after breakfast when appropriate in the morning; (2) from 8.5 hours after breakfast, continuing for 1.5 hours, when appropriate in the afternoon; and (3) from 11.5 hours after breakfast, continuing for 5.5 hours, when appropriate in the evening. Then in step 2020 the program starts at the last breakfast on departure time as previously determined and subtracts 3 days from the Julian date to find the first day for application of the caffeine rules. Then in step 2030, the next three days (Day 1, Day 2, and Day 3 inclusively) have caffeine times set to the afternoon caffeine time. Then step 2040 checks when to schedule the intake of anticipatory caffeine on Day 4. Then step 2050 sets the Caffarray variable for the B.T.F.W.B.D.T. day to no caffeine unless Rule 4 has determined that caffeine is desirable on that day. And then in step 2060 the next two days have the Caffarray variable set to afternoon caffeine time on destination time. Execution then returns to the Init subroutine.

Figure 21:
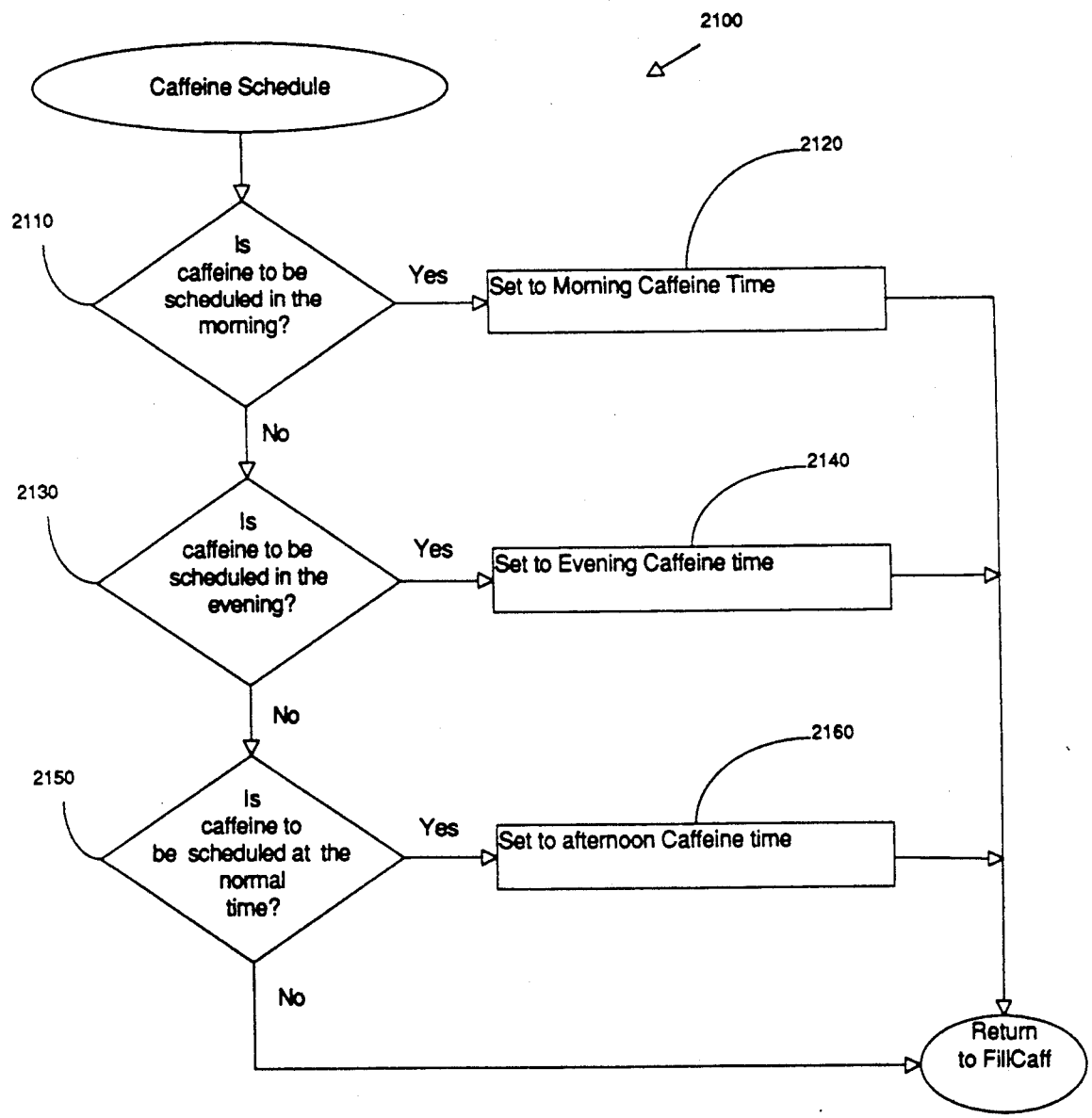
FIG. 21 is a logic flow diagram for the subroutine Caffeine Schedule.

Referring to FIG. 21 there is shown a flow chart for the subroutine Caffeine Schedule generally designated 2100. First step 2110 checks to see if caffeine is scheduled to be ingested in the morning. If the answer is "yes", then in step 2120 the Caffarray variable for the desired day is set to the morning caffeine time range and the subroutine is done. If the answer is "no", then step 2130 checks to see if caffeine is scheduled to be ingested in the evening. If the answer is "yes" then in step 2140 the Caffarray variable for the desired day is set to the evening caffeine time range and the subroutine is done. If the answer is "no", then step 2150 checks to see if caffeine is scheduled to be ingested at the normal time.

If the answer is "yes" then in step 2160 the Caffarray variable for the desired day is set to the afternoon caffeine time range and the subroutine is done. If the answer is "no", then the subroutine is done. Execution then returns to the FillCaff subroutine.

Figure 22:
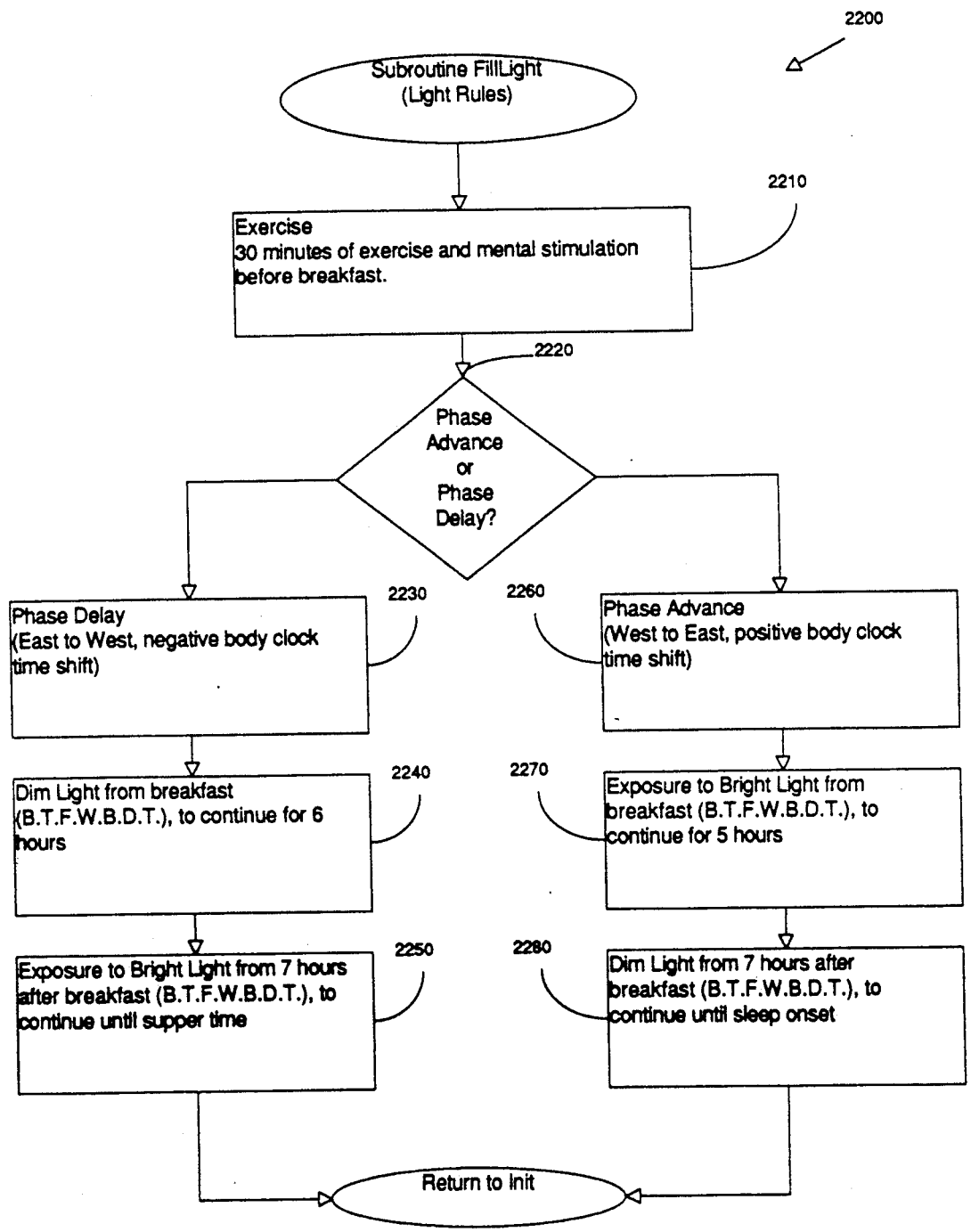
FIG. 22 is a logic flow diagram for the subroutine FillLight Light Rules.

Referring to FIG. 22 there is shown a flow chart for the subroutine FillLight, generally designated 2200. This subroutine sets the times surrounding the time shift period centering on the B.T.F.W.B.D.T. meal for exercise, extra exposure to bright light, and desired dim light. First in step 2210 the Exercise variable for the desired day is set for 30 minutes of exercise and mental stimulation immediately before the B.T.F.W.B.D.T. meal. Then in step 2220 the program determines if the trip involves phase delay (East to West travel typified by a negative body clock time shift 2230) or phase advance (West to East travel typified by a positive body clock time shift 2260). If the answer is "phase delay", then step 2240 sets the DimLight variable from the time of the B.T.F.W.B.D.T. meal to continue for 6 hours. And then in step 2250 sets the BrightLight variable from −7 hours after from the B.T.F.W.B.D.T. meal to continue until suppertime. If the answer is "phase advance", then step 2270 sets the BrightLight variable from the time of the B.T.F.W.B.D.T. meal to continue for 5 hours. And then in step 2280 sets the DimLight variable from 7 hours after the B.T.F.W.B.D.T. meal to continue until sleep onset. Execution then returns to the Init subroutine.

Figure 23:
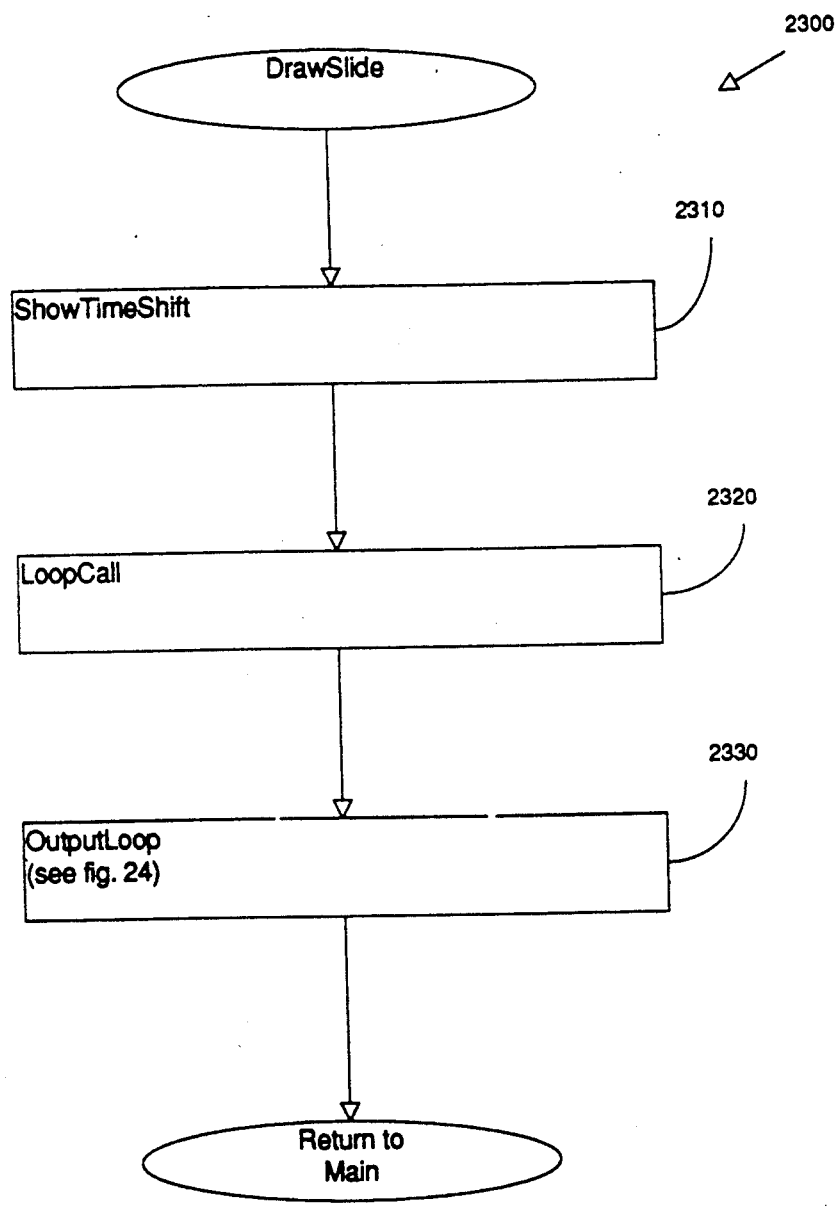
FIG. 23 is a logic flow diagram for the subroutine DrawSlide.
Figure 24:
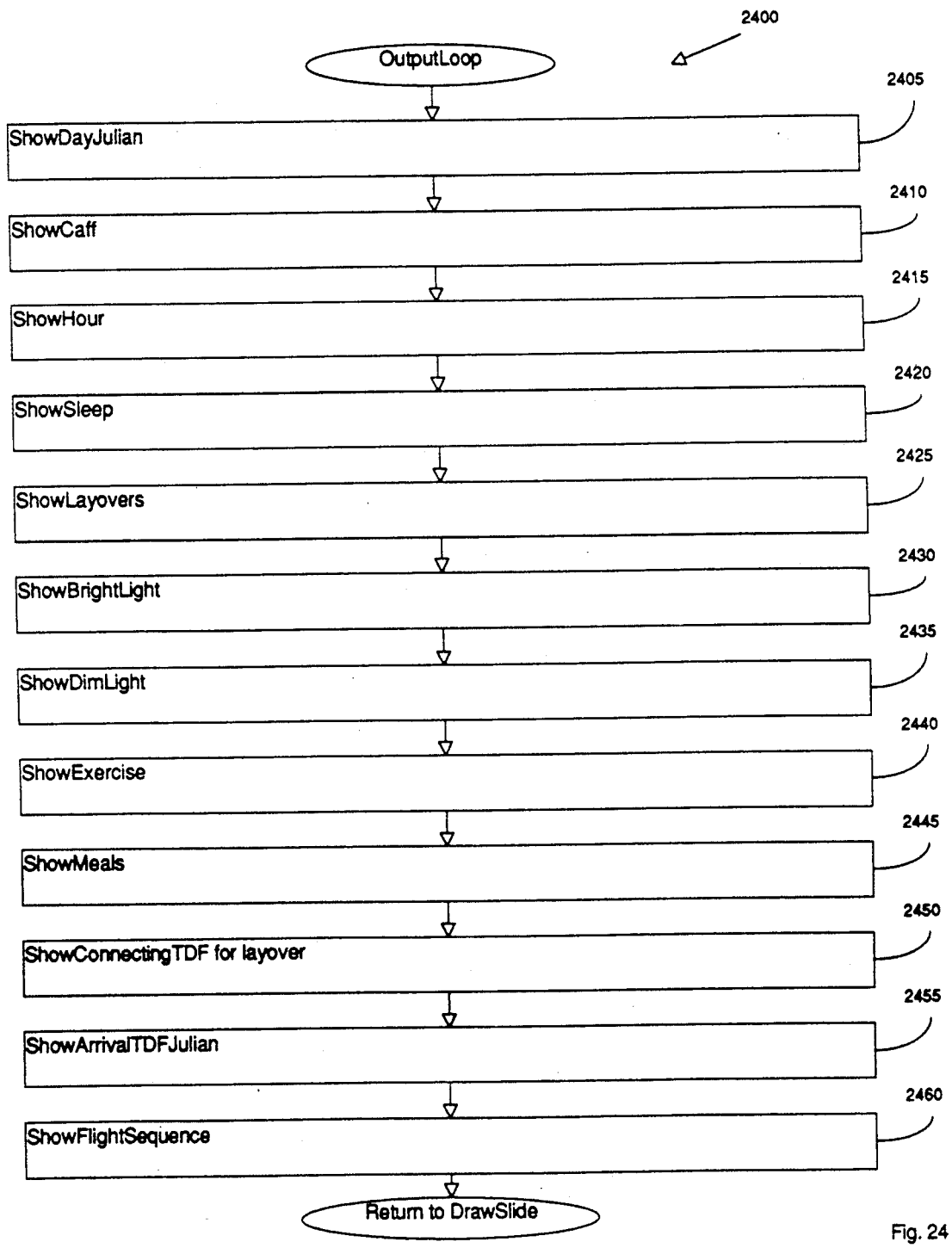
FIG. 24 is a logic flow diagram for the subroutine OutputLoop.

Referring to FIG. 23 there is shown a flow chart for the subroutine DrawSlide generally designated 2300. This subroutine outputs the anti-jet lag recommendations in a format readable by the traveler, after all the needed times have been calculated and stored in appropriate data structures. In Step 2310 the subroutine ShowTimeShift outputs the Actual Time Shift (the time shift relative to world time), the Effective Time Shift (the time shift that a person would experience in the phase shift or phase advance of the body), and the Body Clock Time Shift (the most efficient time shift that causes the least disruption in the physiology of the person). In step 2320 LoopCall sets up timearrive and timedepart with appropriate TDF's, times, JulianDates, as well as the number of days to be represented on the Slide Rule. A TDF is a "Time Differential Factor", the time difference from Greenwich Mean Time. In step 2330 the subroutine OutputLoop is called, as is more fully described in the explanation of FIG. 24 provided below. OutputLoop checks for any of the various zeitgebers which happened during a particular time period, and outputs them in a slide rule format. Execution then returns to the Main routine.

Referring to FIG. 24 there is shown a flow chart for the subroutine OutputLoop, generally designated 2400. This subroutine prints the anti-jet lag recommendations in a format readable by the traveler after all the needed times have been calculated and stored in appropriate data structures. In Step 2405 the subroutine ShowDayJulian prints the departure's Julian Day or date at the appropriate location on the slide rule. In Step 2410 the subroutine ShowCaff prints the ingestion of caffeine at the appropriate location on the slide rule. In Step 2415 the subroutine ShowHour prints the hours at the appropriate location on the slide rule. In Step 2420 the subroutine ShowSleep prints sleep patterns at the appropriate location on the slide rule. In Step 2425 the subroutine ShowLayovers prints layover times at the appropriate location on the slide rule. In Step 2430 the subroutine ShowBrightLight prints the time period for exposure to bright light at the appropriate location on the slide rule. In Step 2435 the subroutine ShowDimLight prints the time for dim light at the appropriate location on the slide rule. In Step 2440 the subroutine ShowExercise prints the time period for exercise at the appropriate location on the slide rule. In Step 2445 the subroutine ShowMeals prints the feast or fast meals at the appropriate location on the slide rule. In Step 2450 the subroutine ShowConnectingTDF for layover prints the layover times and local TDF at the appropriate location on the slide rule. In Step 2455 the subroutine ShowArrivalTDFJulian prints the Arrival location dates at the appropriate location on the slide rule. In Step 2460 the subroutine ShowFlightSequence prints the flight departures and arrivals at the appropriate location on the slide rule. Execution then returns to the DrawSlide routine.

Figure 26:
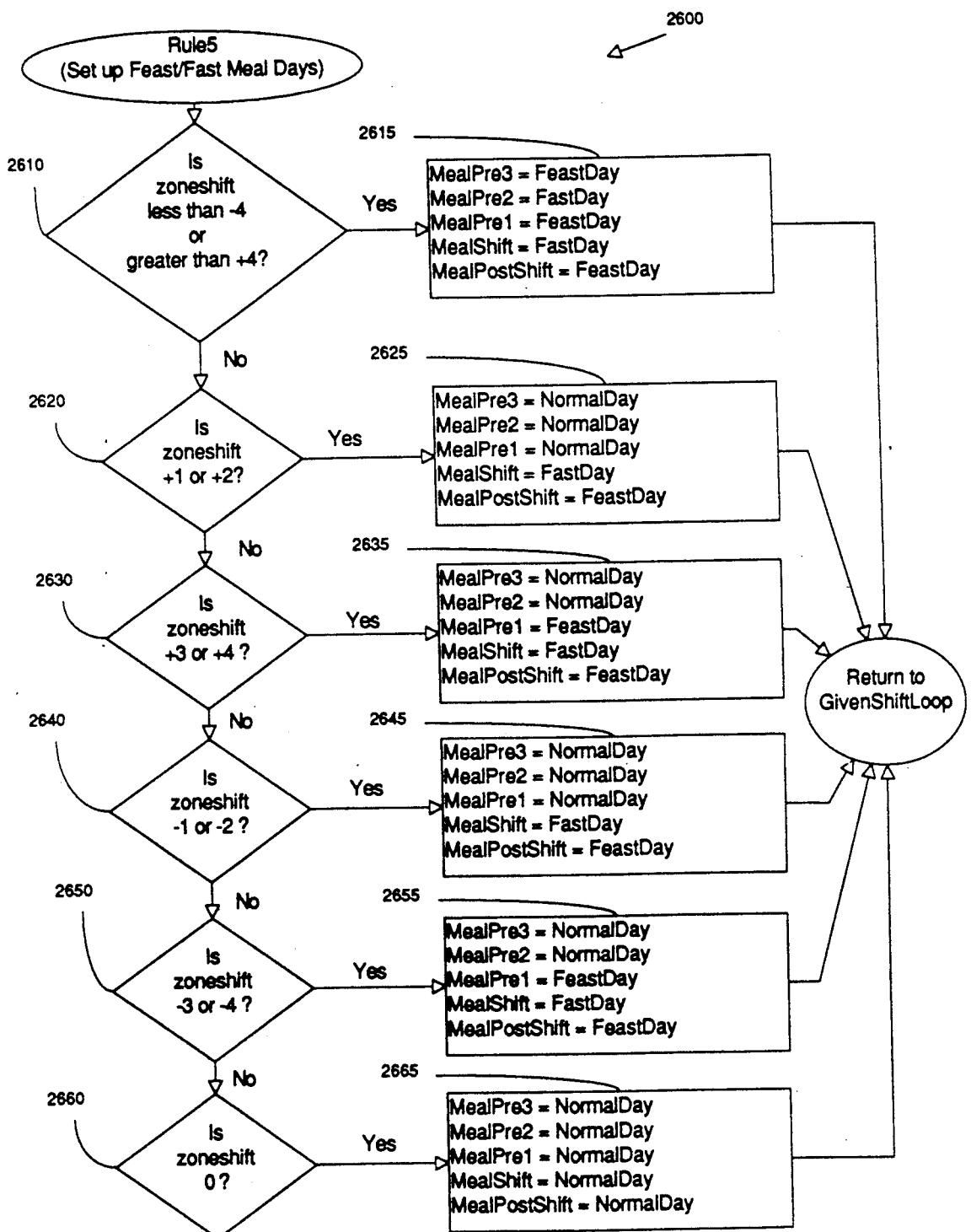
FIG. 26 is a logic flow diagram for the subroutine Rule5.

Referring to FIG. 26 there is shown a flow chart for the subroutine Rule 5, generally designated 2600, which sets up the feast/fast meal days based on zoneshift. This calculation is made for the day of the recommended time shift (MealShift), the day of arrival (MealPostShift), the day before the time shift, (MealPre1), and each of the two days prior to "MealPre1" (MealPre2 and MealPre3). In step 2610 the question "Is zoneshift less than −4 or greater than +4?" is asked. If the answer is "yes" then step 2615 sets MealPre3 to a FeastDay, MealPre2 to a FastDay, MealPre1 to a FeastDay, MealShift to a FastDay, and MealPostShift to a FeastDay. The subroutine is then done. If the answer is "no" then in step 2620 the question "Is zoneshift +1 or +2?" is asked. If the answer is "yes" then step 2625 sets MealPre3 to a NormalDay, MealPre2 to a NormalDay, MealPre1 to a NormalDay, MealShift to a FastDay, and MealPostShift to a FeastDay. The subroutine is then done. If the answer is "no" then in step 2630 the question "Is zoneshift +3 or +4?" is asked. If the answer is "yes" then step 2635 sets MealPre3 to a NormalDay, MealPre2 to a NormalDay, MealPre1 to a FeastDay, MealShift to a FastDay, and MealPostShift to a FeastDay The subroutine is then done. If the answer is "no" then in step 2640 the question "Is zoneshift −1 or −2?" is asked. If the answer is "yes" then step 2645 sets MealPre3 to a NormalDay, MealPre2 to a NormalDay, MealPre1 to a NormalDay, MealShift to a FastDay, and MealPostShift to a FeastDay. The subroutine is then done. If the answer is "no" then in step 2650 the question "Is zoneshift −3 or −4?" is asked. If the answer is "yes" then step 2655 sets MealPre3 to a NormalDay, MealPre2 to a NormalDay, MealPre1 to a FeastDay, MealShift to a FastDay, and MealPostShift to a FeastDay. The subroutine is then done. If the answer is "no" then in step 2660 the question "Is zoneshift 0?" is asked. By the process of elimination only the answer of "yes" is left and step 2655 sets MealPre3 to a NormalDay, MealPre2 to a NormalDay, MealPre1 to a NormalDay, MealShift to a NormalDay, and MealPostShift to a NormalDay. The subroutine is then done. Execution then returns to the calling routine.

Figure 27:
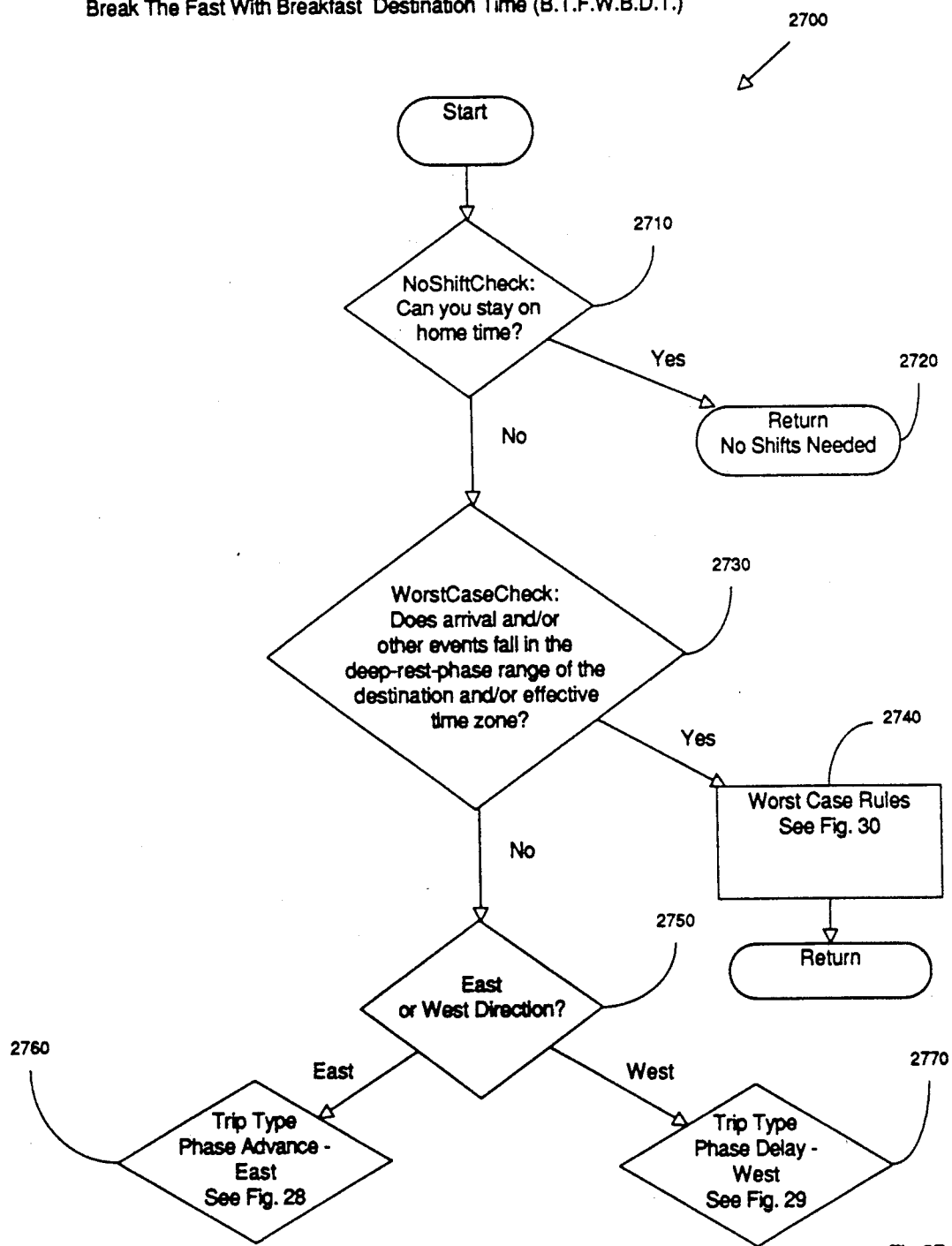
FIG. 27 illustrates the method for calculating B.T.F.W.B.D.T.

Referring to FIG. 27 there is shown a flow chart used to determine the best time for the Break the Fast with Breakfast Destination Time (B.T.F.W.B.D.T.) meal, generally designated 2700. In order to determine the best time for B.T.F.W.B.D.T., the program checks for the following conditions. First in step 2710, a subroutine NoShiftCheck determines whether it is possible to stay on home time. This is a function of: (1) How long the traveler is going to be at the destination. If the stay is greater than NitesCompare, then the traveler should shift onto the new time. NitesCompare is set to the value of 4. (2) If you can have meetings at the same time as usual in your normal-efficient-active-phase range, give or take an hour, and (3) the people you are meeting with can accommodate your schedule, then you may stay on home time. The second and third criteria often depend on the overlapping meeting times available to accomplish the tasks needed. If enough overlapping meeting time exists, the traveler can stay on home time. If the answer returned from the subroutine is "yes", then no shifts are needed and the traveler can stay on home time and the routine is done. If the answer is "no" then WorstCaseCheck 2730 next checks to see if an arrival and/or other event falls in the deep-rest-phase range of the destination and/or effective time zone. If the answer is "yes" then the program calls a subroutine which covers worst case rules described in detail later with reference to FIG. 30. The worst case rules subroutine is designed to be easily expandable as new worst case trip combinations come up without affecting the remainder of the B.T.F.W.B.D.T. module. Nevertheless, the majority of trips do not involve the previous two scenarios and the trip type (Phase Advance-East or Phase Delay-West) determines the appropriate rules to follow. Therefore in step 2750 the routine checks to see if the leg being analyzed is a Phase Advance-East or Phase Delay-West (i.e. East or West Direction). In the case of Phase Advance-East step 2760 calls the Trip Type Phase Advance-East subroutine described in detail later with reference to FIG. 28 to determine the appropriate B.T.F.W.B.D.T. meal timing. In the case of Phase Delay-West step 2770 calls the Trip Type Phase Delay-West subroutine described in detail later with reference to FIG. 29 to determine the appropriate B.T.F.W.B.D.T. meal timing. Execution then returns to the calling routine.

Figure 28:
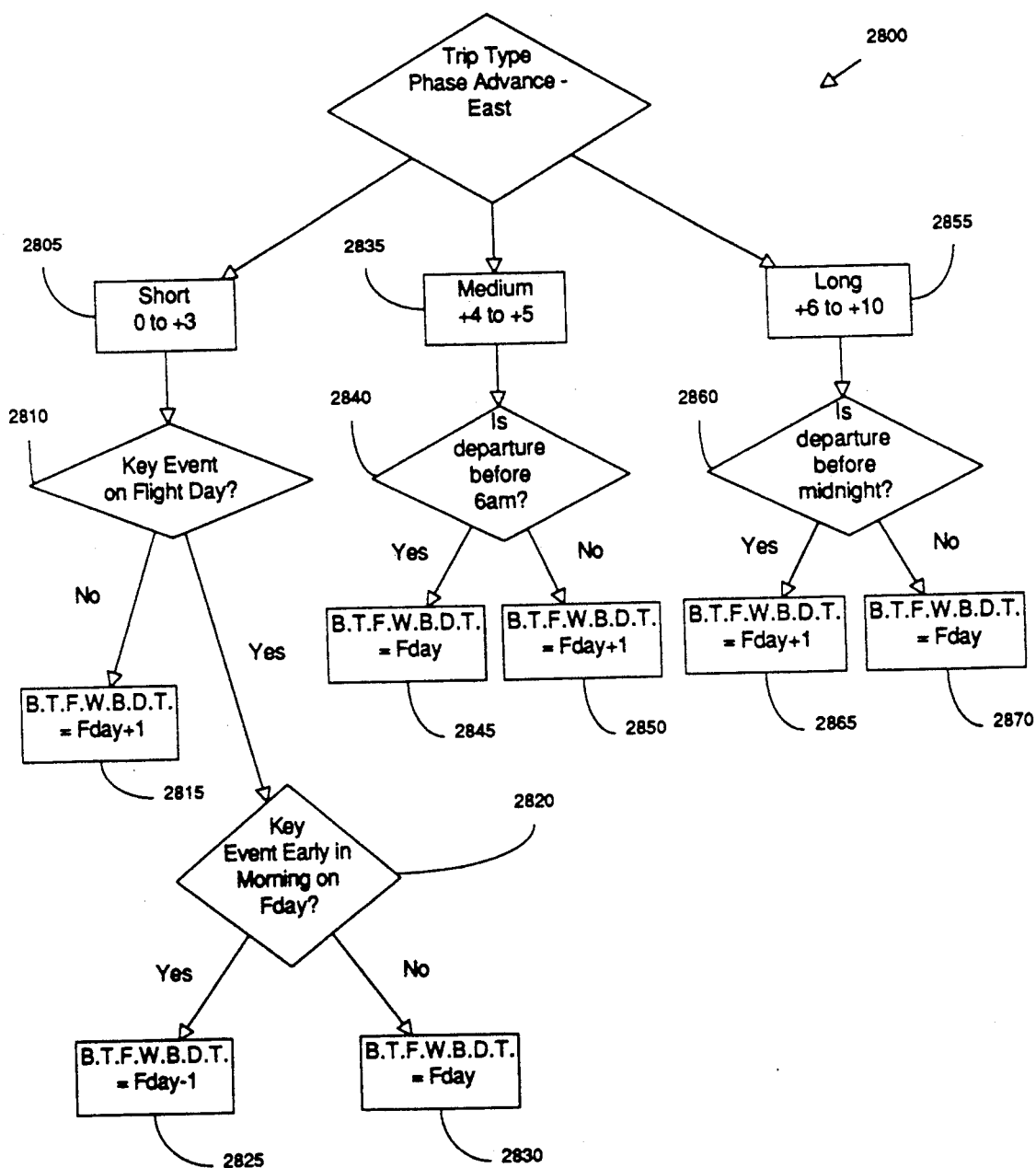
FIG. 28 is a logic flow diagram for the subroutine Trip Type - Phase Advance-East.

Referring to FIG. 28 there is shown a flow chart showing the subroutine Trip Type Phase Advance-East, generally designated 2800. First the number of time changes for the phase shift is determined; either short (0 to +3), medium (+4 to +5), or long (+6 to +10). If short 2805 then step 2810 asks the question "Is there a key event on the flight day?". If the answer is "no", then step 2815 sets the B.T.F.W.B.D.T. to Fday+1 (Fday=Flight Day). If the answer is "yes", then step 2820 ask the question "Is there is a key event early in the Morning on the flight day". If there is, then step 2825 sets B.T.F.W.B.D.T. to Fday−1, otherwise step 2830 sets B.T.F.W.B.D.T. to Fday. If medium 2835, then step 2840 asks "Is the departure before 6 am?". If the answer is "yes", then step 2845 sets B.T.F.W.B.D.T. to Fday. If the answer is "no", then step 2850 sets B.T.F.W.B.D.T. to Fday+1. If long 2855, then step 2860 asks "Is the departure before midnight?". If the answer is "yes", then step 2865 sets B.T.F.W.B.D.T. to Fday+1. If the answer is "no", then step 2870 sets B.T.F.W.B.D.T. to Fday. Execution then returns to the B.T.F.W.B.D.T. subroutine.

Figure 29:
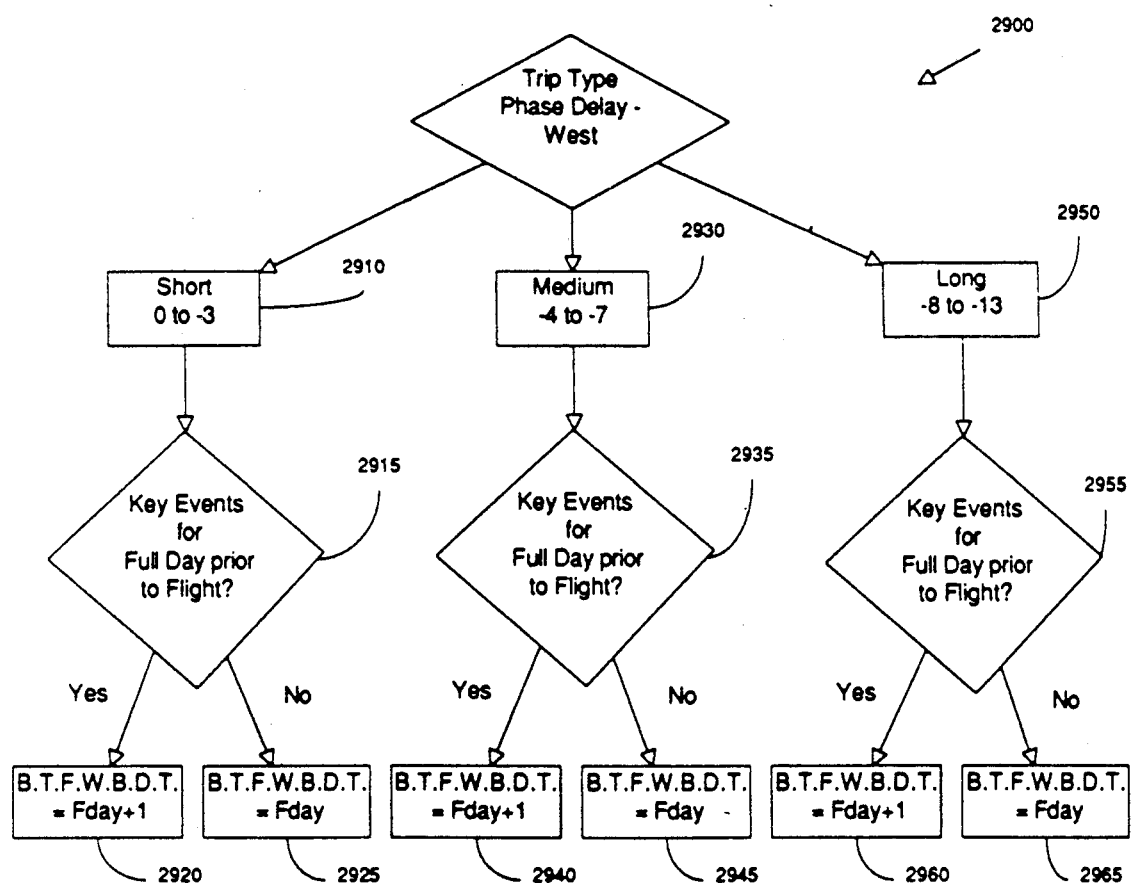
FIG. 29 is a logic flow diagram for the subroutine Trip Type - Phase Delay-West.

Referring to FIG. 29 there is shown a flow chart showing the subroutine Trip Type Phase Delay-West, generally designated 2900. First the number of time changes for the phase shift is determined; either short (0 to −3), medium (−4 to −7), or long (−8 to −13). The routine leaves these three groupings since they are influenced by the extension of the day going west. If short 2910 then step 2915 asks the question "Is there a key event for a Full Day prior to the flight?". If the answer is "yes", then step 2920 sets B.T.F.W.B.D.T. to Fday+1. If the answer is "no", then step 2925 sets B.T.F.W.B.D.T. to Fday. If medium 2930 then step 2935 asks the question "Is there a key event for a Full Day prior to the flight?". If the answer is "yes", then step 2940 sets B.T.F.W.B.D.T. to Fday+1. If the answer is "no", then step 2945 sets B.T.F.W.B.D.T. to Fday. If long 2950 then step 2955 asks the question "Is there a key event for a Full Day prior to the flight?". If the answer is "yes", then step 2960 sets B.T.F.W.B.D.T. to Fday+1. If the answer is "no", then step 2965 sets B.T.F.W.B.D.T. to Fday. Execution then returns to the B.T.F.W.B.D.T. subroutine.

Figure 30:
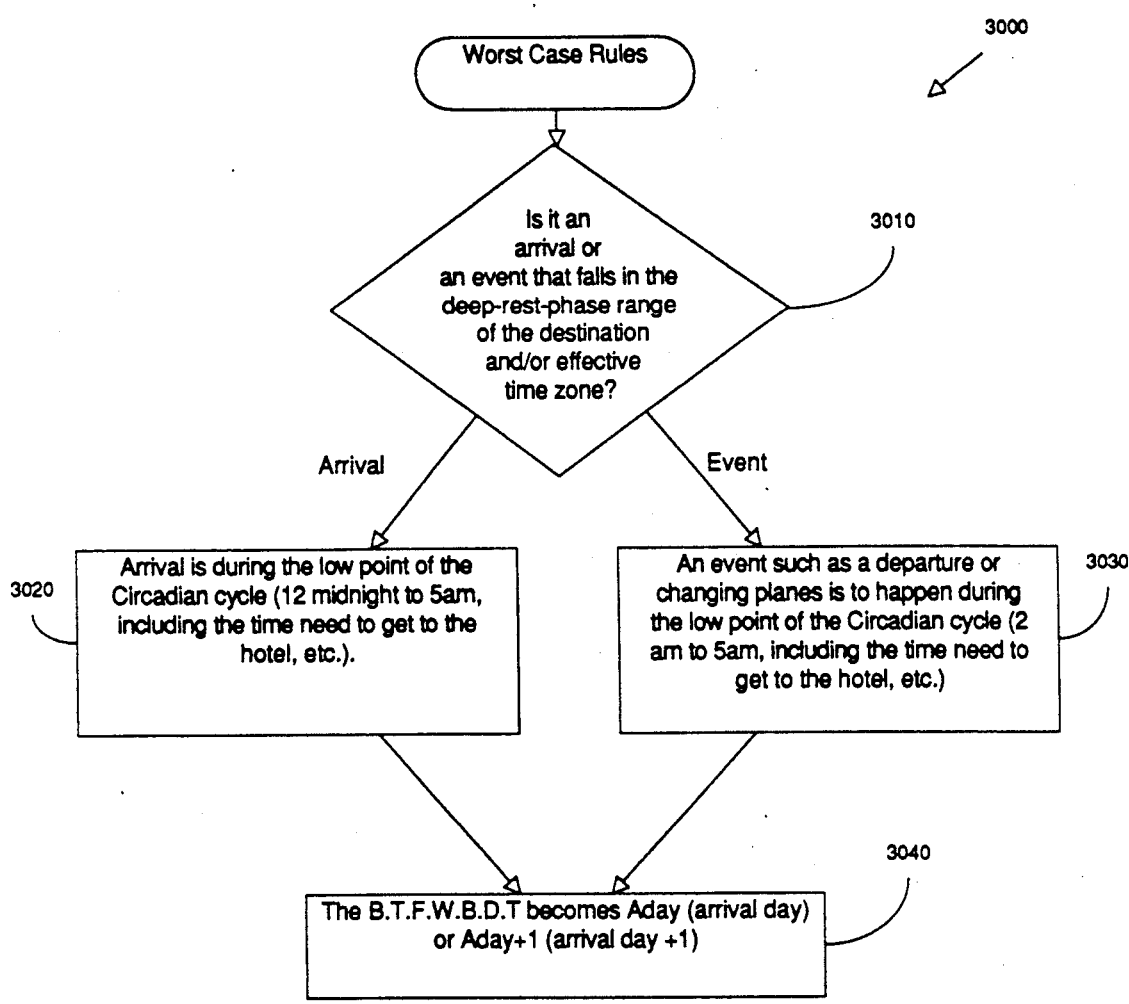
FIG. 30 is a logic flow diagram for the subroutine Worst Case Rules.

Referring to FIG. 30 there is shown a flow chart used to handle worst case rules for conditions such as arrival and/or event timing conditions, generally designated 3000. This subroutine is called if an arrival and/or other event falls in the deep-rest-phase range of the destination and/or effective time zone, but may be easily expanded to account for other worst case conditions. Step 3010 checks to see if it is an arrival or an event that falls in the deep-rest-phase range of the destination and/or effective time zone. If arrival is during the low point of the Circadian cycle (12 midnight to 5 am, including time needed to get to the hotel) and that arrival time is still during the active phase of the previous effective time zone, step 3020 then recommends staying on the previous effective time zone and shifting at the first available time after arrival. Similarly, if an event such as a departure or changing planes happens during the low point of the Circadian cycle (2 am to 5 am, including layover time) and that event is still during the active phase of the previous effective time zone, step 3030 then recommends staying on the previous effective time zone and shifting at the first available time after the event. In step 3040 the B.T.F.W.B.D.T. becomes Aday (arrival day) or sometimes Aday+1 (arrival day +1) depending on the timing of the flight. An individual has a nominal 16 hour active phase each day with a small dawn or dusk phase (of 1 or 2 hours) on each end of the active phase. It is task related and the glossary should be consulted under the discussion of the normal-efficient-active-phase range. The rule for a stopover event recommends that for a stopover overnight in a hotel to get the next connection or for a sightseeing tour during the day the traveler should stay on or phase shift to the closest effective time zone. Execution then returns to the B.T.F.W.B.D.T. subroutine.

Before a daily agenda or slide rule can be printed for a particular time shift, it is necessary to determine the appropriate dates to phase shift for a given itinerary. It is often undesirable to shift to a new time zone on every leg of a trip, even if each leg is at a new time zone. By scanning a prospective itinerary, the program can recommend the time zone a traveler should live on at each destination, the "Effective Time Zone orientation", and then print jet lag countermeasures whenever a phase shift is desired.

Figure 32:
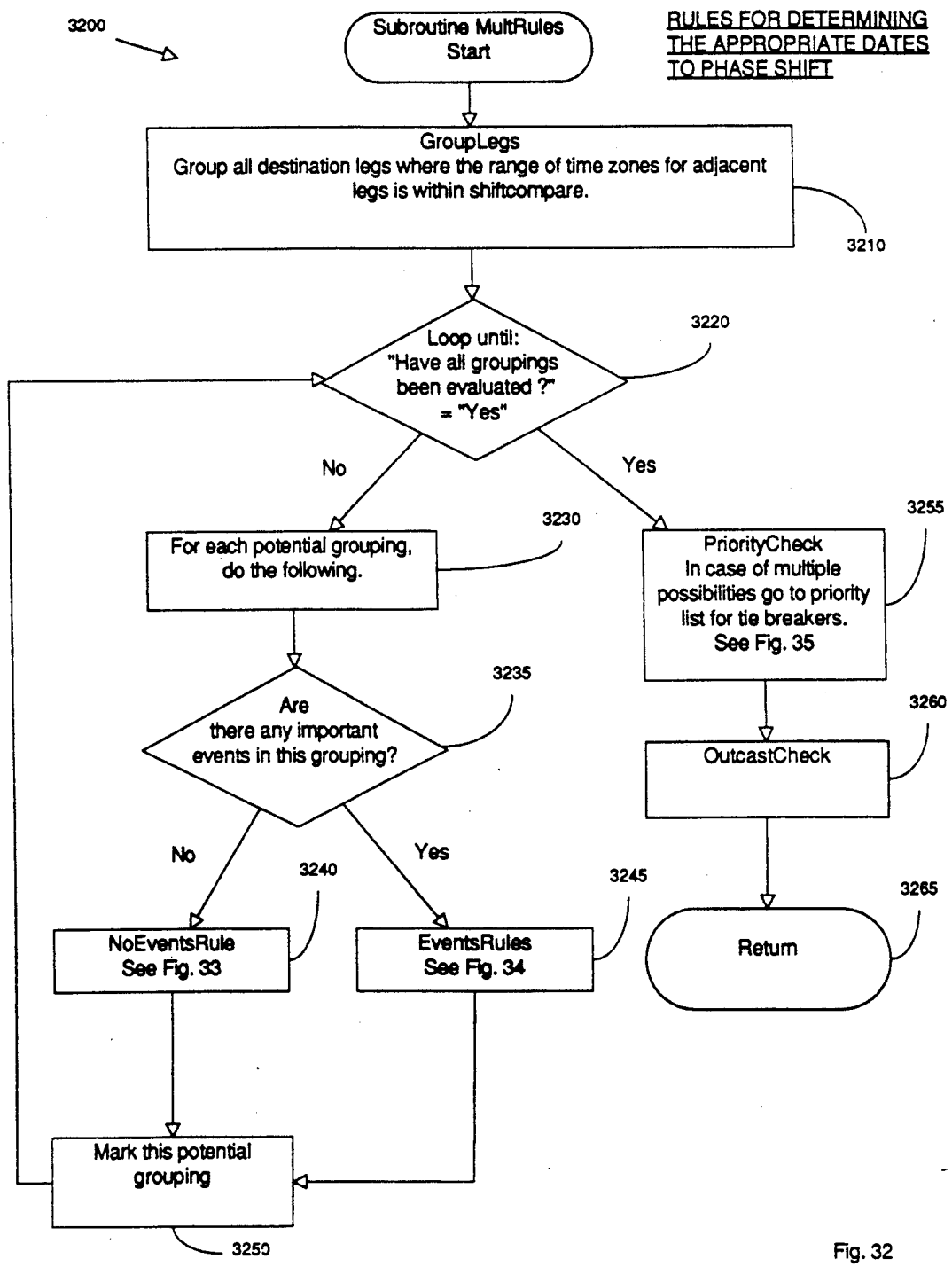
FIG. 32 illustrates the specific method for determining the appropriate date to phase shift.

Referring to FIG. 32 there is shown a flow chart for the subroutine MultRules, generally designated 3200. In this subroutine the full itinerary for a traveler is examined to determine the appropriate dates to phase shift. First in step 3210 a subroutine GroupLegs is called to group all the destination legs where the range of time zones for adjacent legs is within shiftcompare. Shiftcompare is set to the value of 3. This assumes the range of time covered by shiftcompare will allow all events to be incorporated in the overlapping time window. An extension on this uses the key events and/or meeting time needed for various stops to more explicitly define what shiftcompare is equal to. (It should be noted that there are two common cases. First, trips often reduce to the simple case of traveling to only one time zone for greater than NitesCompare nights. And second, adjacent legs often reduce to the case of including only one leg). Next in step 3220 the routine performs an evaluation loop for each of these potential groupings. Then for each of the potential groupings step 3230 asks the following question. In step 3225 the routine checks to see if there are any important events in this grouping. If there are no important events, then the NoEventsRule 3240 is called to evaluate the grouping. If there are important events, then the EventsRule 3245 is called to evaluate the grouping. Then in step 3250 this potential grouping is marked and the routine analyzes the next potential grouping in the evaluation loop. After the evaluation loop has been finished, PriorityCheck 3255 checks to see if there are multiple possible solutions covering legs found in two or more groupings. If there are, then the priority list for tie-breakers is called, described in detail later with reference to FIG. 35. Finally OutcastCheck 3260 checks for the case of an outcast leg. If one is found then the outcast leg possibilities rule is called. By definition the problem with an outcast leg is that it cannot be grouped in any set of time zones. It must therefore be on the previous effective time or on the upcoming effective time. Two levels of user interaction are possible in deciding on the solution. The program can issue a suggestion on a recommended grouping for the leg based on which of the two adjacent effective time zones has the most common active phase hours with the outcast leg. To allow more of a choice for the traveler, the program can display the hours that are appropriate for being on the active phase of the two adjacent effective time zones and give the user a suggestion on a recommended grouping for the leg; then the user can make the choice. Even if the choice is made by the user, it should be flagged as a problem. Execution then returns to the main program with a recommended solution for the given itinerary of the traveler.

Figure 33:
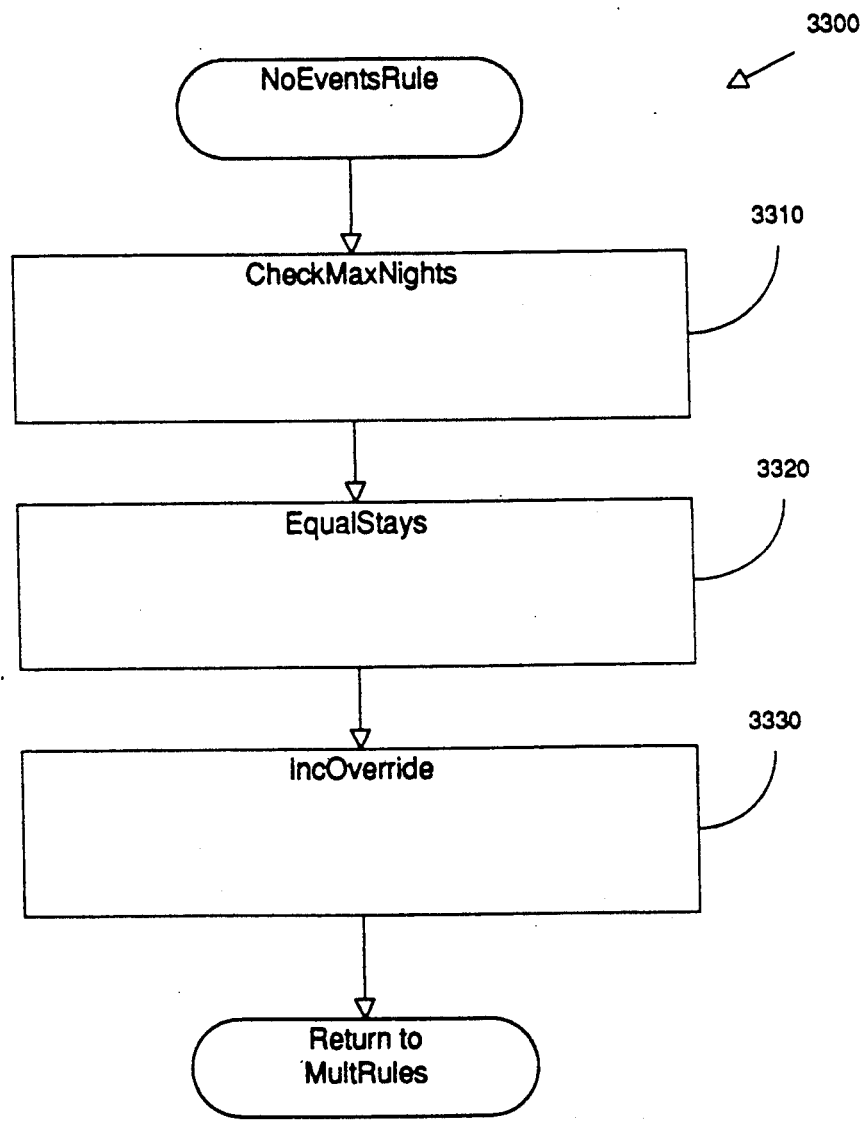
FIG. 33 is a logic flow diagram for the subroutine NoEventsRule.

Referring to FIG. 33 there is shown a flow chart for the subroutine covering the NoEventsRule, generally designated 3300. Under this rule, CheckMaxNight 3310 first chooses the destination leg with the maximum number of nights as the anchor leg of the group. Next in EqualStays 3320, if two or more legs with the maximum stays are within one night of each other, then it chooses the leg with the smallest time zone change as the anchor leg of the group. IncOverride 3330 may override the solution arrived at by the previous two steps. If an upcoming leg increases the phase shift needed, then the greater time zone shift should be taken. Increases can be in a positive or negative direction. Execution then returns to the MultRules subroutine.

Figure 34:
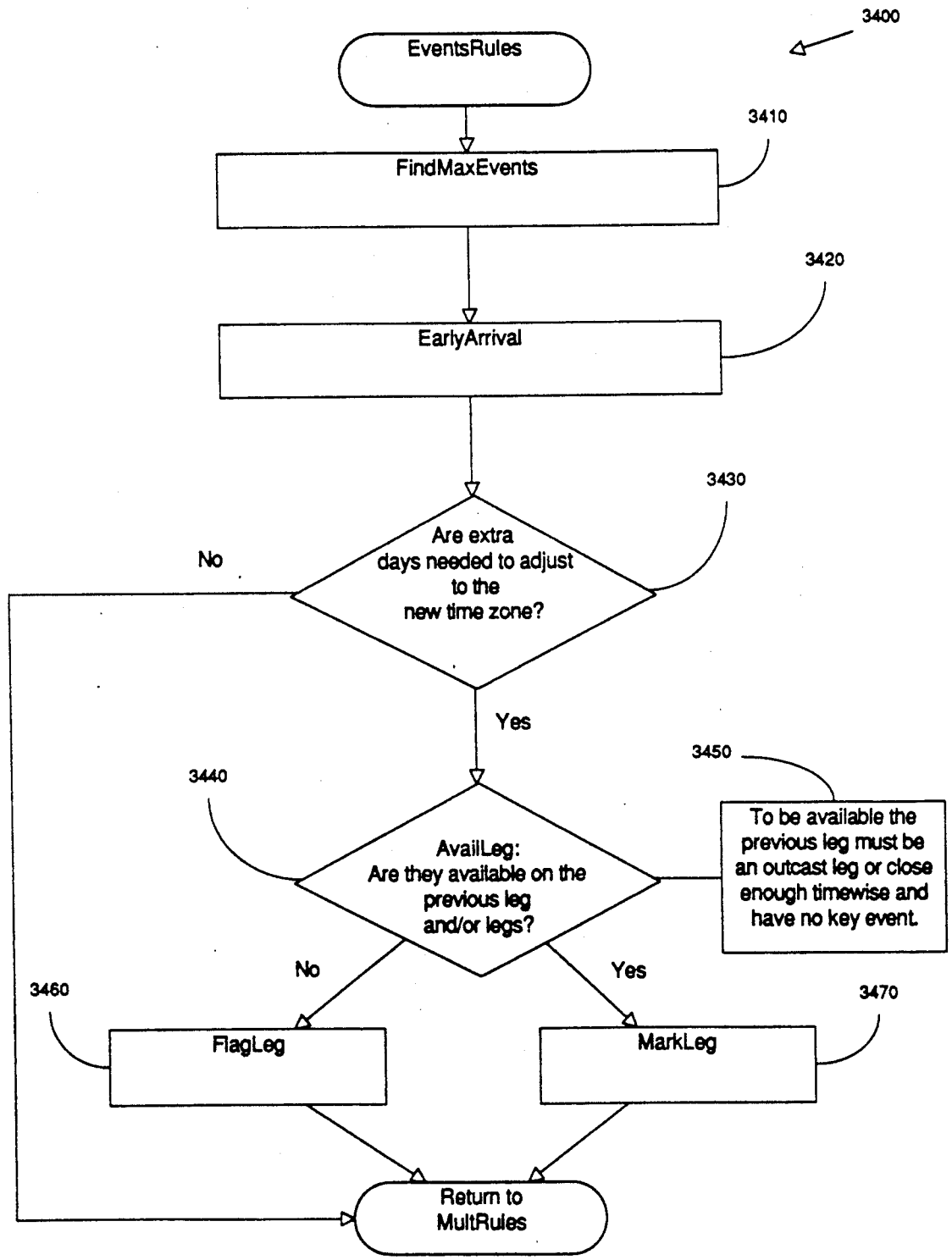
FIG. 34 is a logic flow diagram for the subroutine EventsRules.

Referring to FIG. 34 there is shown a flow chart for the subroutine covering the EventsRule, generally designated 3400. Under this rule, FindMaxEvents 3410 chooses the destination with the maximum number of days of important events as the anchor leg of the group. Then EarlyArrival 3420 uses the number of days after arrival on the new time zone that the first key event is scheduled and the preferred time zone readjustment day to check to see if enough days are allotted to fully adjust to the new time zone. In step 3430, if no extra days are needed to adjust to the new time zone, return to the evaluation loop. However, if extra days are needed, AvailLeg 3440 checks to see if extra days are available on the previous leg and/or legs. As noted in 3450, to be available the previous leg must be an outcast leg or close enough time wise and have no key event. If the answer is "no", FlagLeg 3460 then flags this section of the trip as having potential problems associated with recovering from jet-lag. If the answer is "yes", then MarkLeg 3470 marks the previous leg as available to shift to the new time zone early. Execution then returns to the MultRules subroutine.

Figure 35:
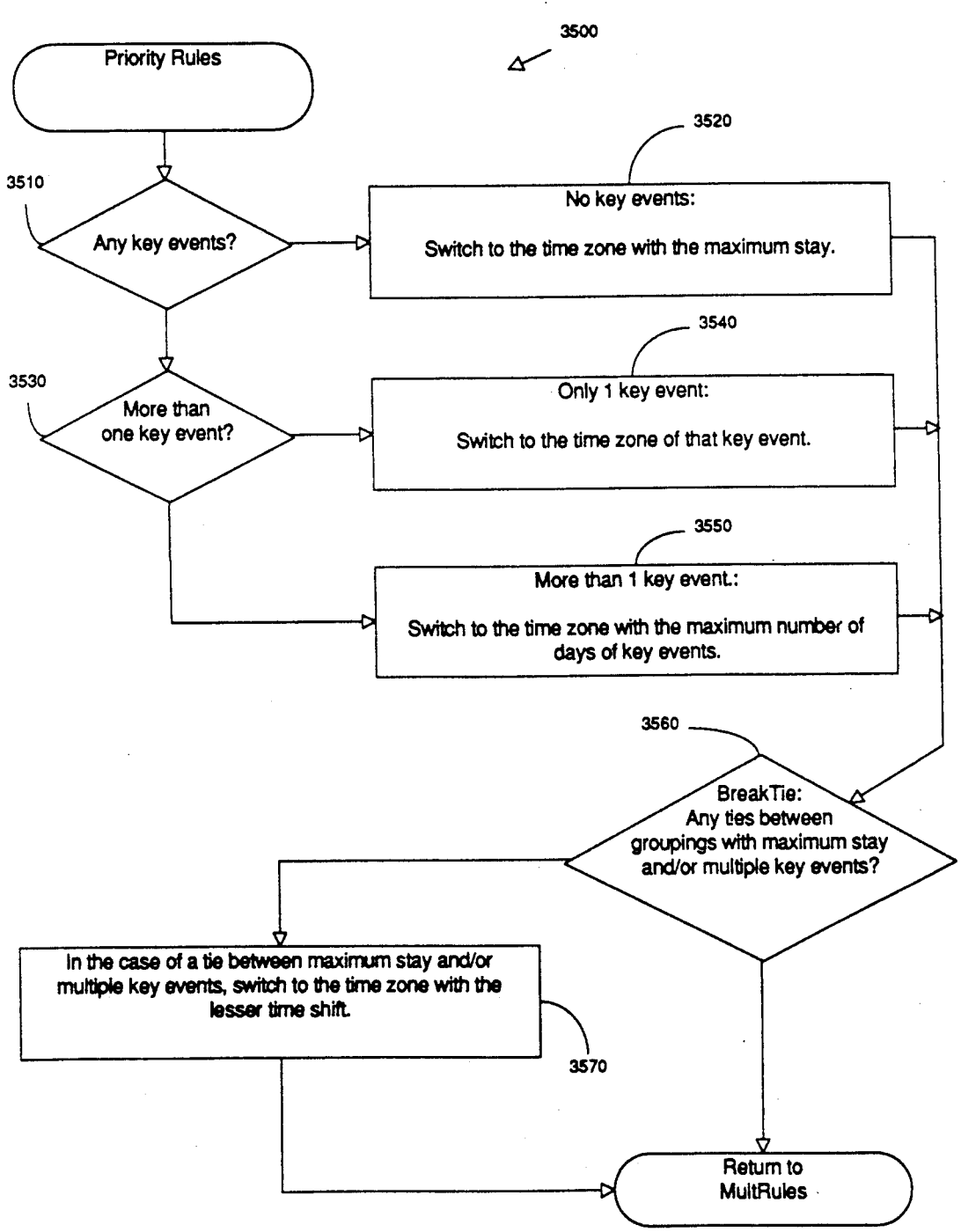
FIG. 35 is a logic flow diagram for the subroutine Priority Rules.

Referring to FIG. 35 there is shown a flow chart for the Priority Rules, generally designated 3500, which is called when there are multiple possible solutions for legs found in two or more groupings. First step 3510 checks to see if there are any key events in the groupings. If the answer is "no", step 3520 recommends the traveler switch to the time zone with the maximum stay. If the answer is "yes", step 3530 checks to if there is more than one key event. If the answer is "no", step 3540 recommends the traveler switch to the time zone of that key event. If the answer is "yes", step 3550 recommends the traveler switch to the time zone with the maximum number of days of key events. Then BreakTie 3560 checks to see if there is a tie between groupings with either maximum stays with no key events and/or multiple key events duration. If the answer is "no" the subroutine is done. If the answer is "yes", step 3570 recommends the traveler switch to the time zone with the lesser time shift. Always phase shift and/or time zone shift, as appropriate, to the new time zone as soon as possible (i.e. on the first day in that grouping unless the trip gets into some override situation). Execution then returns to the MultRules subroutine.

The following glossary is provided to enable a better understanding of the terms used in describing this embodiment.

active-phase-range

The program defaults to an active-phase-range of 16 hours, starting with breakfast at 7 am and continuing until bedtime at 11 pm. These values may be altered for the preferred life style of the individual.

Aday

Aday is the arrival day of the flight. Consequently Aday+1 is the day after arrival.

anchor leg

The anchor leg of a grouping is the destination leg which represents the effective time zone on which the traveler will be living. While at other legs which are members of this group, the traveler should schedule eating and sleeping schedules as if still in that time zone.

anchor sleep

A minimum of 7.5 to 8 hours of sleep is needed by most people in order to receive the rest benefits needed to function properly. The first 4 hours of normal sleep directly after sleep onset are called "anchor sleep" or sometimes "core sleep". Although 3:30 to 4:30 am is the low point of the circadian cycle, having 4 hours of anchor sleep usually allows the circadian acrophases to come at approximately the right time of day. Having had the 4 hours of core sleep one, of course, needs to make up the missing 3 to 4 hours sometime else in the day. For Example, in the case of an overnight trip from the eastern United States to Europe, the extra sleep needed could be picked up by not napping and then going to bed earlier than normal, sleeping 10 hours instead of a normal 8 hours.

B.T.F.W.B.D.T.

B.T.F.W.B.D.T. (Break The Fast With Breakfast Destination Time). The first breakfast on destination time follows a lowering of the glygocen level through fasting and helps adjust the body to the new time zone.

Chronobiotics

Chronobiotics are drugs that are zeitgebers.

circadian cycle

A circadian cycle exhibits about 24-hour periodicity.

circadian acrophase for peak performance

The circadian acrophase (peak in a sine curve) for peak performance is that portion of the active-phase-range statistically determined to be the phase or time of day yielding the average best performance as a function of the phase angle within the circadian cycle for any task.

deep-rest-phase range

The program defaults to a deep-rest-phase range for sleep of 8 hours, with bedtime at 11 pm. These values may be altered for the preferred life style of the individual.

Destination legs

A destination leg is a stopover with an overnight stay not associated with a connecting flight.

Dyschronogenic

Capable of producing dyschronism, i.e. induced loss of or flattening of circadian-rhythm wave forms.

Fday

Fday is the flight departure day. Consequently Fday+1 is the day after departure, and Fday−1 is the day before departure.

Full day

A full day is defined as the amount of time needed to complete any key events before they collide with the final B.T.F.W.B.D.T. phase shift protocols.

Grouping

The TDF's of potential groupings are within "shift-compare" hours or time zones of each other, without any intermediate leg jumping outside that range. An extension to this grouping rule uses calculated overlapping time windows to evaluate the groupings. If enough common hours exist in the overlapping time windows, a potential grouping may be formed. 1 hour total time changes are usually considered to be grouped together.

key event

A key event is one where the traveler desires and/or needs to perform close to the best of his ability. Usually associated with the circadian acrophase for peak performance.

low point of the circadian cycle

Between 3:30 and 4:30 am in the morning, relative to a bedtime of 11 pm and getting up at 6 or 7 in the morning.

NitesCompare

NitesCompare is a value used to look at the number of nights at a given time zone or grouping which allows enough time to adjust to that time zone and then readjust to an upcoming time zone. Uses nights, which are the rest phase of the circadian cycle.

| Phase Change | NitesCompare |
| --- | --- |
| +0 to +4 | 4 (3½) nights |
| 0 to −5 | 4 (3½) nights |
| +5 to +10 | 7 nights |
| −6 to −13 | 7 nights | normal-efficient-active phase range

Based on the input normal breakfast time as the anchor point. Breakfast time plus 1 hour, continuing for 10 hours. This includes an hour on both sides of the typical 8 hour performance window. Complements the deep-rest-phase range. See the circadian acrophase for peak performance. Daily time frame for various functions to show circadian acrophase for peak performance: Elementary cognitive functions—arithmetic, etc.—early in the morning. Slightly complex cognitive functions (including how long one remembers what was learned) and raw physical strength and body temperature peak—in the afternoon. Highly complex cognitive functions (the Eureka effect, may leave one tired the next day)—late evening phase (11 pm, midnight).

outcast leg

A stopover of 1 or possibly 2 nights that is not within "shiftcompare" of any immediately previous or following anchor leg. It does not allow enough nights to shift onto its time zone and then shift to another time zone. For example, a traveler going from New York, stopping in San Francisco for a day of meetings, and then continuing on to Tokyo, would find San Francisco to be an outcast leg.

overlapping meeting times

Similar to overlapping time windows but uses input meeting times (start hour, ending hour, and time needed) to determine the hours found in common during the normal-efficient-active phase range for the participants in the two time zones with different circadian phases.

overlapping time windows

Overlapping time windows are determined by calculating the common active phase hours of two or more locations. It uses a default of 8 hours plus 2 hours, or values entered by the user to raise or lower this window's start and stop times. For instance, the default may be 9 am to 5 pm (for the 8 hour period) extended to 8 am to 6 pm with the extra 2 hours.

override situation

An override situation happens when a priority rule forces a decision favoring one potential anchor leg over another.

phase advance

Phase advance happens when the body clock has to be reset forward, generally associated with a trip crossing time zones from west to east, such as New York City to London (normally a +5 hour time shift or phase shift).

phase angle

Phase angle is a temporal statement defining a specific sector or point within a period given either in degrees (out of 360 degrees) or in hours (out of 24 hours).

phase delay

Phase delay happens when the body clock has to be reset backwards, generally associated with a trip crossing time zones from east to west, such as London to New York City (normally a −5 hour time shift or phase shift).

phase shift

Refers to the internal human aspect of time change in degrees (out of 360 degrees) or more usually in hours (out of 24 hours).

PSI shift

When one's circadian acrophase for peak performance has changed by an advance or a delay relative to the environmental or daily phase references dictated by external zeitgebers such as meal timing, light timing, etc. For example the "favored meeting time" used to be 10 am, but now the "favored meeting time" is 3 pm.

shiftcompare

Shiftcompare is set to 3 time zones. When used, "TDF's" must be less than shiftcompare apart (e.g. 0, 1, or 2 time zones). It is used to check if enough of an active phase time range exists between two locations to allow the destination legs to be put into a grouping An extension to this uses calculated overlapping time windows to evaluate the groupings.

TDF

TDF is an abbreviation for time differential factor, measured from Greenwich Mean Time. This factor is negative going west from GMT to the International Date Line (New York City is −5 EST) and positive going east from GMT (Paris is +1 CEST).

tie-breakers

In the case of two or more potential groupings with similar legs as members, but different anchor leg solutions, a series of priority rules determines the relative strengths of each solution for a decision.

time zone change

Refers to the environmental aspect of time change. In the science, Phase Shift with capital letters refers to the environmental aspect of time change; phase shift with small letters refers to the internal human aspect of time change.

worst case

An arrival or event which forces the traveler to function during the deep-rest-phase range of his desired circadian cycle. For example, arriving at Singapore at 2 in the morning.

zeitgebers

Zeitgebgers (from the German for 'time givers') are external stimuli such as light, food, drugs, oxygen, exercise, and social or interpersonal activities which regulate or shift the phase of a circadian rhythm, thus resetting the body's clocks.

zoneshift

Zoneshift is the time change the traveler is to adjust to.

While the invention has been particularly taught and described with reference to the preferred embodiment, those of ordinary skill in the art will appreciate that minor modifications in form and details may be made without departing from the spirit and scope of the invention. For instance, although the illustrated embodiment shows the invention incorporated in a standalone processing system for recommending flight times, departure dates, and schedule, the invention could also be integrated into an airline reservation system and used to recommend specific available flights. In an alternative embodiment the present invention could be implemented into an existing reservation system and interface directly with all listed flight schedules. Ticketing agents could, simultaneous with performing reservation services, complete a comprehensive trip analysis identifying potential jet lag problems in the proposed itinerary, and offer, along with the passenger's ticker, personalized instructions capable of eliminating days of unnecessary physical and mental dysfunction during their trip. Alternatively, recommendations could be calculated from ticketing information during batch file runs at the end of a travel agent's day. Also, at present, no chronobiotics other than the methylxanthines are considered generically acceptable (i.e., without detrimental side effects, and with well-defined phase-response characteristics). However it is a distinct advantage of the system defined herein, that, as such useful chronobiotics may be proven in the future to be generically acceptable, and as they appear in the over-the-counter pharmacopoeia, then they can be readily introduced into the program to obtain the desired effect. Accordingly, all such modifications are embodied within the scope of this patent, which is particularly pointed out by the following claims.

We claim:

1. A method of operating a general purpose computer to provide information to an individual to help the individual to reduce dysfunction caused by a particular trip across a plurality of time zones, the method comprising the steps of:

receiving itinerary data, the itinerary data including a trip departure time, a trip departure location, a trip destination location and a trip arrival time;

accessing a database of time zone information to determine the time zones of a plurality of locations in response to the trip departure location and the trip destination location;

calculating a phase change between the departure and destination locations in response to the accessed time zone information;

determining a time shift day in response to the itinerary data and phase change;

determining a reference point on the time shift day;

using the reference point to generate daily recommendations of activity responsive to the itinerary data and the calculated phase change in accordance with chronobiological rules, the recommendations including a schedule for the days surrounding the time shift day indicating sleep times, meal times, meal types, caffeine times, and a watch reset time; and providing the daily recommendations of activity to the individual.

2. A method as in claim 1 wherein said step of calculating a phase change treats certain large phase advances as phase delays.

3. A method as in claim 1 further comprising the step of receiving input of key event data, the key event data including the location, date, time, and duration of key events, and wherein said step of determining a time shift day is further responsive to the key event data.

4. A method as in claim 3 further comprising the step of receiving individual preferences data and wherein said step of using the reference point to generate daily recommendations of activity is further responsive to the individual preferences data.

5. A method as in claim 4 wherein the step of receiving individual preferences data includes receiving data for preferred meeting times, preferred sleep times, and preferred meal times.

6. A method as in claim 4 wherein said step of using the reference point to generate daily recommendations of activity further comprises the step of determining a recommendation for times of activity and times of inactivity.

7. A method as in claim 1 further comprising the step of accessing a database of daylight savings time information responsive to a particular location, and wherein said step of calculating a phase change is responsive to the daylight saving information for each input location.

8. A method as in claim 1 wherein said step of using the reference point to generate daily recommendations of activity includes the step of identifying potentially dyschronogenic schedules.

9. The method of claim 1 further comprising the steps of grouping legs of a trip in response to the time zones of destinations and recommending dates for phase shifts in response to times and locations of key events, lengths of stay at each destination, and magnitudes of phase shifts between groups.

10. The method of claim 1 wherein the reference point determined is a time for a break-the-fast-breakfast meal.

11. The method of claim 1 wherein said step of using the reference point to generate daily recommendations of activity further comprises the step of determining a recommendation for times to adjust levels of light.

12. The method of claim 11 wherein the steps of providing the daily recommendations of activity to the individual comprises the step of adjusting the lights, serving meals, and serving caffeinated drinks to a passenger on a flight in accordance with the daily recommendations.

13. A method of operating a general purpose computer to provide information to an individual to help the individual to reduce dysfunction caused by a particular trip across a plurality of time zones, the method comprising the steps of:

receiving individual traveler preferences data, the preferences data including data indicating preferred meeting times, preferred sleep times, and preferred meal times;

receiving key event data, the key event data including data indicating locations, dates, times and durations of key events;

receiving itinerary data, the itinerary data including data indicating a trip departure time, a trip departure location, a trip arrival time, and a trip arrival location;

accessing a database of time zone information to obtain the time zone of each key event from the key event data and the time zones of the trip departure location and the trip arrival location;

calculating a phase change between the trip departure and destination locations using the accessed time zone information;

converting the phase change to treat phase advances of eleven hours or greater as phase delays;

determining a time shift day in response to the key event data, itinerary data, and phase change;

determining a reference point on the time shift day;

using the reference point to determine daily recommendations responsive to the individual traveler preferences data, the key event data, the itinerary data, the time zone of each key event, and the converted phase change in accordance with chronobiological rules, the recommendations including recommendations for the times of selected zeitgebers on the days surrounding the time shift day; and providing the daily recommendations to the individual.

14. A method as in claim 13 wherein the selected zeitgebers include fast/feast days, the time and date of a break-the-fast-breakfast, meal times, meal types, and caffeine times.

15. A method as in claim 14 adapted to permit the introduction of effective new zeitgebers as they are identified.

16. The method of claim 13 wherein the reference point determined is a time for a break-the-fast-breakfast meal.

17. A computer system for providing information to an individual to allow him to reduce the physical and mental dysfunction caused by a particular trip across a plurality of time zones, the system comprising:

means for receiving itinerary data including a trip departure time, a trip departure location, a trip arrival time, and a trip destination location;

means for accessing a database of time zone information to obtain the time zones of the trip departure location and the trip destination location in response to the itinerary data;

means for calculating the phase change between the departure and destination locations using the accessed time zone information;

means coupled to the data receiving means and to the phase change calculating means for determining a time shift day in response to the received itinerary data and the calculated phase change;

means for determining a reference point on the time shift day;

means for using the reference point to generate recommendations of daily activity, said recommendations responsive to the itinerary data and the calculated phase change in accordance with chronobiological rules, the recommendations including a schedule for the days surrounding the time shift day indicating sleep times, meals times, meal types, caffeine times, and a watch reset time; and output means for providing the recommendations to the individual.

18. The method of claim 17 wherein the reference point determined is a time for a break-the-fast-breakfast meal.

19. A method of operating a general purpose computer to provide information to an individual to help the individual to reduce dysfunction caused by a particular trip across a plurality of time zones, the method comprising the steps of:

receiving itinerary data, the itinerary data including a trip departure time, a trip departure location, a trip destination location and a trip arrival time;

receiving input of key event data, the key event data including the location, date, time, and duration of key events;

accessing a database of time zone information to determine the time zones of a plurality of locations, including the trip departure location and the trip destination location;

calculating a phase change between the departure and destination locations in response to the accessed time zone information;

determining a time shift day in response to the trip departure time, the trip arrival time, the phase change and the key event data;

determining a time for a break-the-fast-breakfast meal on the time shift day;

using the time for the break-the-fast-breakfast meal as a reference point to generate a schedule of daily recommendations of activity for the days surrounding the time shift day in accordance with chronobiological rules; and providing the recommendations to the individual.

20. The method of claim 19 wherein the step of using the time for the break-the-fast-breakfast meal as reference point to generate a schedule of daily recommendations activity includes generating a daily schedule indicating fast/feat days, meal times, meal types, caffeine times, and a watch reset time.

21. The method of claim 19 further comprising the steps of:

recommending changing the time for the break-the-fast-breakfast meal so that an event does not fall into a deep-rest-phase range of the destination or effective time zone; and recommending no break-the-fast-breakfast meal for short trips and trips where key events can take place during a normal-efficient-active phase range of the individual.

22. The method of claim 19 further comprising the step of receiving individual preferences data and wherein said step of using the times for the break-the-fast-breakfast meal time to generate a schedule is responsive to the individual preferences data.

23. The method of claim 19 further comprising the steps of grouping legs of a trip in response to the time zones of destinations and recommending dates for phase shifts in response to times and locations of the key events, lengths of stay at each destination, and magnitudes of phase shifts between groups.

24. The method of claim 19 wherein said step of using the time for the break-the-fast-breakfast meal to generate a schedule of daily recommendations of activity comprises the steps of:

determining a time for a first sleep prior to the time for the break-the-fast breakfast meal;

determining a reset watch time in response to the time for the first sleep prior to the time for the break-the-fast-breakfast meal;

determining a time for a first sleep after the time for the break-the-fast-breakfast meal;

determining a time for a last breakfast on departure time prior to the time for the break-the-fast-breakfast meal; and determining a time for a last sleep on departure time prior to the time for a last breakfast on departure time.

25. The method of claim 24 wherein said step of using the time for the break-the-fast-breakfast meal to generate a schedule of daily recommendations of activity further comprises the steps of:

determining meal times for the days surrounding the time shift day;

determining times for ingesting caffeine on the days surrounding the time shift day; and determining when meals should be skipped on the days surrounding the time shift day.

26. The method of claim 19 wherein said step of providing the recommendations to the individual comprises the step of adjusting lights, serving meals, and serving caffeinated drinks to a passenger on a flight in accordance with the recommendations.

* * * * *